(12) United States Patent
Patton et al.

(10) Patent No.: US 7,550,271 B2
(45) Date of Patent: Jun. 23, 2009

(54) DETECTING PHOSPHO-TRANSFER ACTIVITY

(75) Inventors: Wayne F. Patton, Newton, MA (US); Thomas Edwin Miller, Boston, MA (US)

(73) Assignee: PerkinElmer LAS, Inc., Waltham, MA (US)

( * ) Notice: Subject to any disclaimer, the term of this patent is extended or adjusted under 35 U.S.C. 154(b) by 38 days.

(21) Appl. No.: 11/742,443

(22) Filed: Apr. 30, 2007

(65) Prior Publication Data

US 2007/0287161 A1    Dec. 13, 2007

Related U.S. Application Data

(60) Provisional application No. 60/795,798, filed on Apr. 28, 2006.

(51) Int. Cl.
    C12Q 1/48        (2006.01)
(52) U.S. Cl. ............................... 435/15; 506/9; 558/158
(58) Field of Classification Search ................... 435/15; 506/9; 558/158
    See application file for complete search history.

(56) References Cited

U.S. PATENT DOCUMENTS

| | | | |
|---|---|---|---|
| 4,499,052 | A | 2/1985 | Fulwyler |
| 5,028,545 | A | 7/1991 | Soini |
| 5,871,928 | A | 2/1999 | Fodor et al. |
| 5,902,723 | A | 5/1999 | Dower et al. |
| 5,981,180 | A | 11/1999 | Chandler et al. |
| 6,197,599 | B1 | 3/2001 | Chin et al. |
| 6,916,661 | B2 | 7/2005 | Chandler et al. |
| 2004/0075907 | A1 | 4/2004 | Moon et al. |
| 2004/0125424 | A1 | 7/2004 | Moon et al. |
| 2004/0126875 | A1 | 7/2004 | Putnam et al. |
| 2004/0130761 | A1 | 7/2004 | Moon et al. |
| 2004/0130786 | A1 | 7/2004 | Putnam et al. |
| 2004/0132205 | A1 | 7/2004 | Moon et al. |
| 2004/0171034 | A1 | 9/2004 | Agnew et al. |
| 2004/0179267 | A1 | 9/2004 | Moon et al. |
| 2004/0198712 | A1 | 10/2004 | Koike et al. |
| 2005/0038258 | A1* | 2/2005 | Koike et al. ................. 546/285 |
| 2007/0251824 | A1* | 11/2007 | Patton et al. ................. 204/461 |
| 2007/0287161 | A1* | 12/2007 | Patton et al. ................. 435/7.4 |
| 2008/0064608 | A1* | 3/2008 | Inamori et al. ................. 506/9 |

FOREIGN PATENT DOCUMENTS

| | | |
|---|---|---|
| EP | 1602923 | 12/2005 |
| EP | 1614706 | 1/2006 |
| JP | 2007 228906 | * 9/2007 |
| WO | WO 2006/014424 | 2/2006 |
| WO | WO 2007/131191 | 11/2007 |

OTHER PUBLICATIONS

Bakre et al. (2000) "Expression and Regulation of the cGMP-Binding, cGMP-Specific Phosphodiesterase (PDE5) in Human Colonic Epithelial Cells: Role . . . Peptide" J. Cell Biochem. 77(1):159-167.

Brunet et al. (1999) "Akt Promotes Cell Survival by Phosphorylating and Inhibiting a Forkhead Transcription Factor" Cell 96:857-868.

Burton and Harding, (1998) "Hydrophobic charge induction chromatography: salt independent protein adsorption and facile elution with aqueous buffers" J. Chromatogr. A 814:71-81.

Chester and Marshak (1993) "Dimethyl Sulfoxide-Mediated Primer Tm Reduction: A Method for Analyzing the Role of Renaturation Temperature in the PCR" Anal. Biochem., 209: 284-2900.

Davis, R. J. (1993) "The Mitogen-activated Protein Kinase Signal Transduction Pathway" J. Biol. Chem. 268: 14553-14556.

Fiol, C. J. et al. (1990) "Ordered Multisite Protein Phosphorylation" J. Biol. Chem. 265(11): 6061-6065.

Flotow, H. et al. (1990) "Phosphate Groups as Substrate Determinants for Casein Kinase I Action" J. Biol. Chem. 265: 14264-14269.

Geahlen, R. L. and Harrison, M. L. (1990). In B. E. Kemp (Ed.), Peptides and Protein Phosphorylation, (pp. 239-253).

Grankowski, et al. (1991) "Isolation and characterization of recombinant human casein kinase II subunits alpha and beta from bacteria" Eur. J. Biochem., 198, 25-30.

Hartmann et al. (2002) "Selective DNA attachment of micro- and nanoscale particles to substrates" J. Mater. Res. 17(2):473-478.

Hathaway and Traugh (1979) Cyclic Nucleotide-independent Protein Kinase from Rabbit Reticulocytes J. Biol. Chem., 254, 762-768.

Hudson et al. (1999) "High avidity scFv multimers; diabodies and triabodies" J. Immunol. Methods 231:177-189.

Huston et al. (2001) "Engineered antibodies take center stage" Hum. Antibodies 10:127-142.

Hutti, J.E. et al., (2004) "A rapid method for determining protein kinase phosphorylation specificity" Nature Methods 1(1): 27-29.

Janssens and Goris (2001) "Protein phosphatase 2A: a highly regulated family of serine/threonine phosphatases implicated in cell growth and signaling" Biochem. J. 353: 417-439.

Kennelly, P. J., and Krebs, E. G. (1991) "Consensus Sequences as Substrate Specificity Determinants for Protein Kinases and Protein Phosphatases" J. Biol. Chem. 266: 15555-15558.

Kim et al. (1999) "Substrate Specificities and Identification of Putative Substrates of ATM Kinase Family Members" J. Biol. Chem. 274(53):37538-37543.

Li et al. (2002) "AKT/PKB Phosphorylation of p21 $^{Cip/WAF1}$ Enhances Protein Stability of p21 $^{Cip/WAF1}$ and Promotes Cell Survival" J. Biol. Chem. 277:11352-11361.

Martin et al., (2003) "Quantitative analysis of protein phosphorylation status and protein kinase activity on microarrays using a novel fluorescent phosphorylation sensor dye". Proteomics. 3:1244-1255.

(Continued)

Primary Examiner—Ralph Gitomer
(74) Attorney, Agent, or Firm—Fish & Richardson P.C.

(57) ABSTRACT

Disclosed are methods and reagents for detecting the presence of and/or activity of one or more phospho-transfer activities such as kinase, phosphatase, nucleotide cyclase, or phosphodiesterase activities.

20 Claims, 28 Drawing Sheets

OTHER PUBLICATIONS

Martin, et al., (2003) "Strategies and Solid Phase Formats for the Analysis of Protein and Peptide Phosphorylation Employing a Novel Fluorescent Phosphorylation Sensor Dye". Combinatorial Chem. & High Throughput Screening 6:331-339.

Milward et al. (1999) "Regulation of protein kinase cascades by protein phosphatase 2A" Trends Biochem. Sci. 24: 186-191.

Pearson, R. B., and Kemp, B. E. (1991). In T. Hunter and B. M. Sefton (Eds.), Methods in Enzymology vol. 200, (pp. 62-81). San Diego: Academic Press.

Poljak (1994) "Production and structure of diabodies" Structure 2: 1121-1123.

Roach, P. J. (1991) "Multisite and Hierarchal Protein Phosphorylation" J. Biol. Chem. 266(22): 14139-14142.

Russo, G. L. et al. (1992) "Casein Kinase II Phosphorylates p34$^{cdc2}$ Kinase in G1 Phase of the HeLa Cell Division Cycle" J. Biol. Chem. 267(28): 20317-20325.

Schulenberg et al., (2003)"Analysis of steady-state protein phosphorylation in mitochondria using a novel fluorescent phosphosensor dye". J. Biol Chem. 278(29):27251-27255.

Schulenberg et al., (2004) "Characterization of dynamic and steady-state protein phosphorylation using a fluorescent phosphoprotein gel stain and mass spectrometry". Electrophoresis. 25:2526-2532.

Songyang, Z. et al. (1995) "Catalytic specificity of protein-tyrosine kinases is critical for selective signaling" Nature 373: 536-539.

Steinberg et al., (2003) "Global quantitative phosphoprotein analysis using Multiplexed Proteomics technology". *Proteomics* .3:1128-44.

Stevenson, L.M. et al. (2003) "Substrate Specificity of CDK2-Cyclin A" J. Biol. Chem. 278(52): 50956-50960.

Stocks (2004) "Intrabodies: Production and Promise" Drug Discov. Today 9(22): 960-966.

Wheeler et al. (2003) "Intrabody and Intrakine Strategies for Molecular Therapy" Mol. Ther. 8(3):355-366.

Yamaguchi et al. (2001) "Hydrolysis of phophodiester with hydroxo- or carboxylate-bridged dinuclear Ni(II) and Cu (ii) complexes" Chem. Commun. pp. 375-376.

Yang and Huang (1994) "Identification of -R-X-(X)-S/T-$X_3$-S/T- as Consensus Sequence Motif for Autophosphorylation-dependent Protein Kinase" J. Biol. Chem. 269(47):29855-29859.

Yang et al. (2007)"Ligand Binding to the Androgen Receptor Induces Conformational Changes That Regulate Phosphatase Interactions" Mol. Cell. Biol. 27(9):3390-3404.

Yashiro et al. (1995) "Preparation and Study of Dinuclear Zinc (II) Complex for the Efficient Hydrolysis of the Phosphodiester Linkage in a Diribonucleotide" J. Chem. Soc. Commun. 17: 1793-1794.

Zabrocki et al. (2002) "Protein phosphatase 2A on track for nutrient-induced signaling in yeast" Mol. Microbiol. 43(4): 835-842.

* cited by examiner

UV/Vis spectra of $[Zn_2(phos\text{-}tag)]^{3+}$ – pyrocatechol violet mixture (50μM in HEPES buffer: 10mM, pH 7.0)) in the presence of different anions (250 μM)

UV/Vis spectra of $[Zn_2\text{(phos-tag)}]^{3+}$ - pyrocatechol violet mixture (50μM in HEPES buffer: 10mM, pH 7.0)) in the presence of *different phosphopeptides* (pS, pT, and pY, 200 μM) and *non-phosphopeptide* (P2, 200μM)

Relative binding affinity of different phosphopeptides (pThr, pSer, and pTyr) and non-phosphopeptide (P2) to the $[Zn_2 \text{ (phos-tag)}]^{3+}$ $A_b$: Absorbance of background (no peptides)
$A_s$: Absorbance of peptides at different concentrations UV/Vis spectra obtained by additions of *peptides with phosphorylated Threonine* (pT) to the HEPES buffer (10mM, pH 7.0) containing [$Zn_2$ (phos-tag)]$^{3+}$ complexed with pyrocatechol violet (50μM) with final concentrations: 0, 10, 50, 100, and 200 μM.

Peptide sequence: Arg-Arg-Arg-Glu-Glu-Glu-pThr-Glu-Glu-Glu-Ala-Ala

UV/Vis spectra obtained by additions of *peptides with phosphorylated Serine (pS)* to the HEPES buffer (10mM, pH 7.0) containing [Zn$_2$(phos-tag)]$^{3+}$ complexed with pyrocatechol violet (50μM) with final concentrations: 0, 10, 25, 50, 100, and 200 μM.

Peptide sequence: Arg-Arg-Arg-Glu-Glu-Glu-pSer-Glu-Glu-Ala-Ala

UV/Vis spectra of $[Zn_2(phos\text{-}tag)]^{3+}$ – pyrocatechol violet mixture (50μM in HEPES buffer: 10mM, pH 7.0)) in the presence of *different proteins* (3mg/ml)

Visualizing binding

The color of the mixtures in the absence and presence of different analytes

From left to right: HEPES buffer (10mM, pH 7) containing *pyrocatechol violet* (50 µM), *[Zn₂ (phos-tag)]³⁺ - pyrocatechol violet* (50 µM), *[Zn₂ (phos-tag)]³⁺ - pyrocatechol violet* (50 µM) with addition of *phosphopeptide* (100 µM), *non-phosphopeptide* (100 µM), *phosphoprotein* (Ovalbumin, 1.5mg/ml), and *non-phosphoprotein* (BSA, 1.5mg/ml)

Fig. 28

DETECTING PHOSPHO-TRANSFER ACTIVITY

CROSS-REFERENCE TO RELATED APPLICATIONS

This application claims priority to U.S. application Ser. No. 60/795,798, filed on Apr. 28, 2006, the contents of which is hereby incorporated by reference in its entirety.

BACKGROUND

The addition or removal of phosphate groups to or from target proteins are two of the most important signaling events in the cell and, as a result, regulate many diverse cellular processes. Thus, methods that detect the addition of a phosphate group (i.e., phosphorylation) or the removal of a phosphate group (i.e., dephosphorylation) of a target protein are highly useful. Phosphate groups are also transferred in other reactions of biological importance.

SUMMARY

Disclosed herein are rapid methods to evaluate phospho-transfer events (e.g., phosphorylation or dephosphorylation events) on target molecules. These methods allow, for example, the rapid analysis of specificities of enzymes having phospho-transfer activity such as an activity of a kinase, phosphatase, nucleotide cyclase, or phosphodiesterase. Thus, the methods and reagents described herein are useful for detecting molecules that play important roles in signal transduction events.

In one aspect, the disclosure provides a method for detecting the presence of a phospho-transfer activity in a sample. The method includes the steps of: contacting a particle (e.g., an encoded particle) that has an attached phospho-transfer substrate with a sample; contacting the particle with a detectable phosphomonoester-selective binding agent; and detecting binding of the detectable phosphomonoester-selective binding agent to the particle. The particle can be identifiable by a particle code. The particles can be magnetic or glass.

The method can further include, after contacting the particle to the sample, separating the at least one encoded particle from the sample. The method can further include the step of separating the at least one encoded particle from the unbound detectable phosphomonoester-selective binding agent. The method can also include immobilizing the phospho-transfer substrate on at least one of the encoded particles. The method can also include matching at least one particle code with an attached phospho-transfer substrate. In some cases, contacting at least one encoded particle with a sample and contacting the at least one encoded particle with a detectable phosphomonoester-selective binding agent can occur at the same time. Detecting can include flow cytometry and can include detecting a particle code.

In some embodiments the detecting comprises detecting the presence or amount of the binding of the detectable phosphomonoester-selective binding agent to at least one encoded particle contacted with the sample as compared to the presence or amount of binding of the detectable phosphomonoester-selective binding agent to the at least one encoded particle not contacted with the sample.

The phospho-transfer activity can be a kinase activity, a phosphatase activity, a nucleotide cyclase activity, or a phosphodiesterase activity. The kinase can be, e.g., a tyrosine kinase, a threonine/serine kinase, a saccharide kinase, or a lipid kinase. The kinase can be $Ca^{2+}$/Calmodulin Dependent Protein Kinase II. The phosphatase can be, e.g., a tyrosine-specific phosphatase, a threonine/serine specific phosphatase, a dual-specificity phosphatase, a saccharide phosphatase, a histidine-specific phosphatase, or a lipid phosphatase. The phosphatase can be PP2A.

In some embodiments, the phosphomonoester-selective binding agent can have the Formula I:

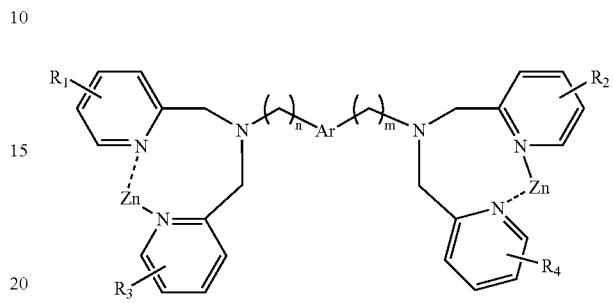

wherein each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group, each n and m are independently 0 or 1; and Ar aryl. Each n and m can be 0. Each n and m can be 1. Each of $R_1$, $R_2$, $R_3$, and $R_4$ are H. The Ar can be anthracene or

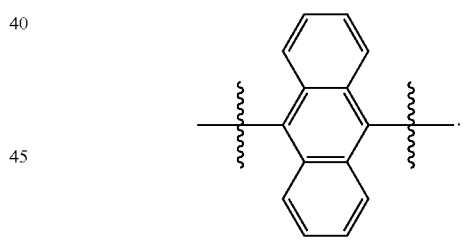

Each of $R_1$, $R_2$, $R_3$, and $R_4$ can be H; n and m can each be 1; and Ar can be

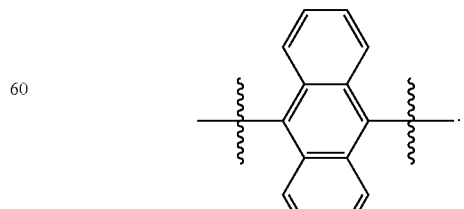

In some embodiments, the phosphomonoester-selective binding agent has the Formula II:

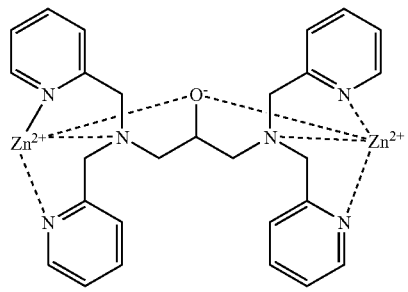

The sample can be a biological sample, e.g., urine, blood, plasma, serum, saliva, semen, sputum, cerebral spinal fluid, tears, mucus, sweat, milk, or semen. The sample can contain a phospho-transfer activity or more than one phospho-transfer activity. A sample can contain one or more different phospho-transfer activities.

In some embodiments, the phospho-transfer substrate can comprise, or be, a polypeptide, a nucleic acid, a nucleotide triphosphate (e.g., ATP or GTP), a nucleotide monophosphate (e.g., a cyclic nucleotide monophosphate such as cAMP or cGMP), a lipid, or one or more saccharide residues. The phospho-transfer substrate can be a phosphorylated form of a substrate (e.g., a phosphorylated form of any of the substrates described herein).

In some embodiments, an increase in the amount of the detectable phosphomonoester-selective binding agent bound to the phospho-transfer substrate contacted with the sample as compared to the amount bound to the phospho-transfer substrate not contacted with the sample indicates the presence of a phospho-transfer activity in the sample. In some embodiments, a decrease in the amount of the detectable phosphomonoester-selective binding agent bound to the phospho-transfer substrate contacted with the sample as compared to the amount bound to the phospho-transfer substrate not contacted with the sample indicates the presence of a phospho-transfer activity in the sample.

In some embodiments, the detecting is performed at a pH of at least greater than 5.0. The detecting can also be performed at a pH of at least greater than 6.0.

In some embodiments, at least one encoded particle can be contacted with more than one sample in parallel.

In some embodiments, the particle code is a fluorescent dye or a holographic bar code. The particle code can be a nucleic acid. For example, the particle code can be a nucleic acid and the phospho-transfer substrate can contain a nucleic acid which is complementary to the nucleic acid particle code.

In another aspect, the disclosure provides a method for detecting the presence of a phospho-transfer activity in a sample, which method includes the steps of contacting at least one encoded particle with a sample; contacting the at least one encoded particle with a detectable phosphomonoester-selective binding agent has the structure of Formula I:

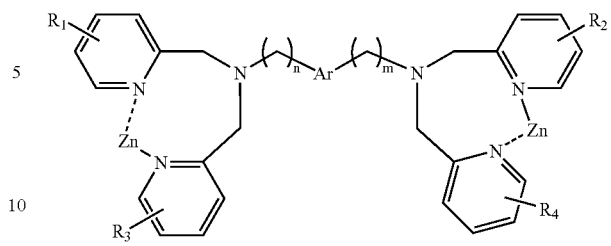

wherein each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group, each n and m are independently 0 or 1; and Ar aryl; and detecting binding of the detectable phosphomonoester-selective binding agent to at least one encoded particle. The at least one encoded particle has an attached phospho-transfer substrate and the phospho-transfer substrate is identifiable by a particle code.

In some embodiments, n and m are both 0 or 1. Each of $R_1$, $R_2$, $R_3$, and $R_4$ can be H. Ar can be anthracene or

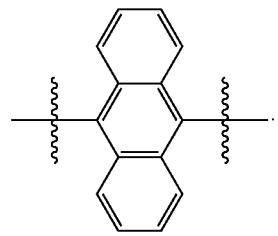

Each of $R_1$, $R_2$, $R_3$, and $R_4$ can be H; n and m can each be 1; and Ar can be

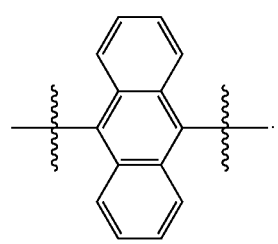

In some embodiments, the detectable phosphomonoester-selective binding agent has the Formula II:

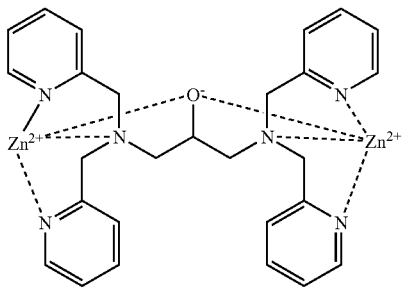

In yet another aspect, the disclosure features a method for detecting the presence of a phospho-transfer activity in a sample. The method includes the steps of: contacting at least one encoded particle with a sample, wherein the at least one encoded particle has an attached phospho-transfer substrate, the phospho-transfer substrate being identifiable by a particle code; contacting the at least one encoded particle with a detectable phosphomonoester-selective binding agent; and detecting binding of the detectable phosphomonoester-selective binding agent to at least one encoded particle, wherein the detection is performed at an operating pH of at least greater than 5.0. The detection can be performed at an operating pH of at least greater than 6.0.

In yet another aspect, the disclosure features a method for detecting the presence of a phospho-transfer activity in a sample, the method comprising: contacting at least one encoded particle with a sample, wherein the at least one encoded particle has an attached phospho-transfer substrate, the phospho-transfer substrate being identifiable by a particle code; contacting the at least one encoded particle with a detectable phosphomonoester-selective binding agent has the structure of Formula I:

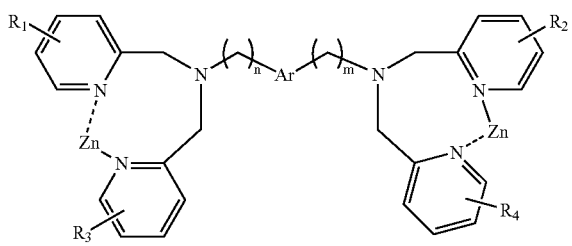

wherein each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group, each n and m are independently 0 or 1; and Ar aryl; and detecting binding of the detectable phosphomonoester-selective binding agent to at least one encoded particle, wherein the detection is performed at an operating pH of at least greater than 5.0. The detection can be performed at an operating pH of at least greater than 6.0.

In some embodiments, n and m are both 0 or 1. Each of $R_1$, $R_2$, $R_3$, and $R_4$ can be H. Ar can be anthracene or

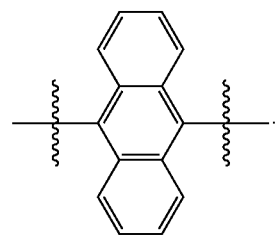

Each of $R_1$, $R_2$, $R_3$, and $R_4$ can be H; n and m can each be 1; and Ar can be

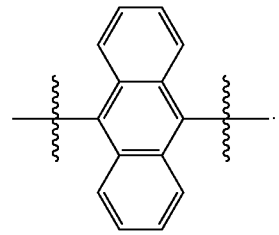

In some embodiments, the detectable phosphomonoester-selective binding agent has the Formula II:

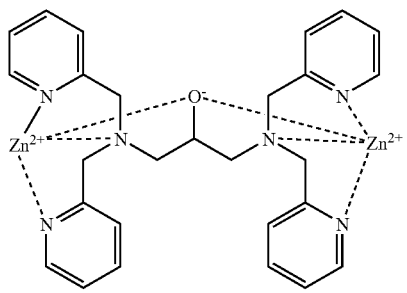

In another aspect, the disclosure features a method for detecting the presence of one or more phospho-transfer activities in a sample. The method includes the steps of: contacting a mixture of encoded particles with a sample, wherein the mixture of encoded particles comprises one or more pluralities of encoded particles, each plurality of particles having a different attached phospho-transfer substrate, the phospho-transfer substrate being identifiable by a particle code; contacting the mixture of encoded particles with a detectable phosphomonoester-selective binding agent; and detecting binding of the detectable phosphomonoester-selective binding agent to at least one of the encoded particles. The detecting can include detecting the presence or amount of the binding of the detectable phosphomonoester-selective binding agent to at least one encoded particle contacted with the sample as compared to the presence or amount of binding of the detectable phosphomonoester-selective binding agent to the at least one encoded particle not contacted with the sample. The method can further include the step of immobilizing the phospho-transfer substrate on the encoded particles. The method can further include the step of after contacting the mixture of encoded particles with the sample, separating the mixture of encoded particles from sample. The method can also include the step of after contacting the mixture of encoded particles with the phosphomonoester-selective binding agent, separating the encoded particles from the unbound detectable phosphomonoester-selective binding agent. The method can also include the step of measuring the amount of binding of the detectable phosphomonoester-selective binding agent to at least one of the phospho-transfer substrates attached to the encoded particles. The method can also include the step of matching at least one particle code with the attached phospho-transfer substrate. The encoded particles can be magnetic. The detecting can include flow cytometry.

In some embodiments, the phosphomonoester-selective binding agent can have the Formula I:

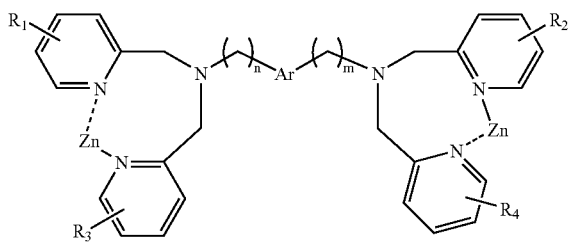

wherein each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group, each n and m are independently 0 or 1; and Ar aryl. Each n and m can be 0. Each n and m can be 1. Each of $R_1$, $R_2$, $R_3$, and $R_4$ are H. The Ar can be anthracene or

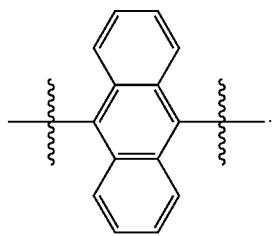

Each of $R_1$, $R_2$, $R_3$, and $R_4$ can be H; n and m can each be 1; and Ar can be

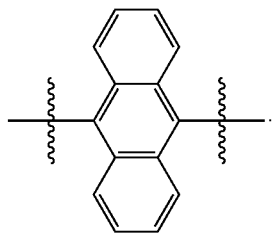

In some embodiments, the phosphomonoester-selective binding agent has the Formula II:

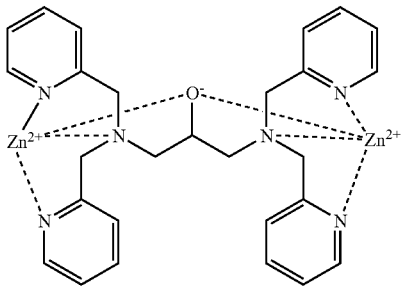

The sample can be a biological sample, e.g., urine, blood, plasma, serum, saliva, semen, sputum, cerebral spinal fluid, tears, mucus, sweat, milk, or semen. The sample can contain a phospho-transfer activity or more than one phospho-transfer activity. A sample can contain one or more different phospho-transfer activities.

In some embodiments, the phospho-transfer substrate can comprise, or be, a polypeptide, a nucleic acid, a nucleotide triphosphate (e.g., ATP or GTP), a nucleotide monophosphate (e.g., a cyclic nucleotide monophosphate such as cAMP or cGMP), a lipid, or one or more saccharide residues. The phosphor-transfer substrate can be a phosphorylated form of a substrate (e.g., a phosphorylated form of any of the substrates described herein).

The sample can contain one phospho-transfer activity or more than one phospho-transfer activity. The sample can contain one or more different phospho-transfer activities.

In some embodiments, an increase in the amount of the detectable phosphomonoester-selective binding agent bound to the phospho-transfer substrate contacted with the sample as compared to the amount bound to the phospho-transfer substrate not contacted with the sample indicates the presence of a phospho-transfer activity in the sample. In some embodiments, a decrease in the amount of the detectable phosphomonoester-selective binding agent bound to the phospho-transfer substrate contacted with the sample as compared to the amount bound to the phospho-transfer substrate not contacted with the sample indicates the presence of a phospho-transfer activity in the sample.

In some embodiments, the particle code is a fluorescent dye or a holographic bar code. The particle code can be a nucleic acid. For example, the particle code can be a nucleic acid and the phospho-transfer substrate can contain a nucleic acid which is complementary to the nucleic acid particle code.

In some embodiments, the mixture of encoded particles can contain more than one plurality of particles. At least two pluralities of particles can include different phospho-transfer substrates, each substrate comprising a variant recognition site specific to one phospho-transfer activity. At least two pluralities of particles can contain different phospho-transfer substrates, each substrate comprising a recognition site for a different phospho-transfer activity.

In some embodiments, the mixture of encoded particles can be contacted with more than one sample in parallel.

In some embodiments, the detecting can be performed at an operating pH of at least about 5.0, 5.5, 6.0, or 6.5, for example, between 6.5 and 8.5 or 6.5 and 8.0.

In yet another aspect, the disclosure provides a method for detecting the presence of one or more phospho-transfer activities in a sample, the method comprising: contacting a mixture of encoded particles with a sample, wherein the mixture of encoded particles comprises one or more pluralities of encoded particles, each plurality of particles having a different attached phospho-transfer substrate, the phospho-transfer substrate being identifiable by a particle code; contacting the at least one encoded particle with a detectable phosphomonoester-selective binding agent has the structure of Formula I:

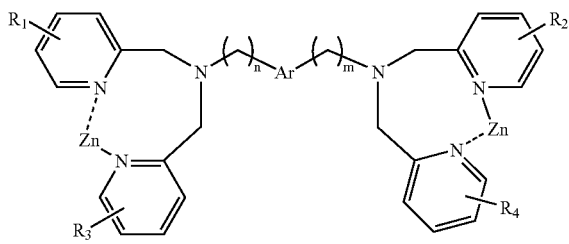

wherein each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group, each n and m are independently 0 or 1; and Ar aryl; and detecting a difference in the binding of the detectable phosphomonoester-selective binding agent to at least one of the phospho-transfer substrates attached to the encoded particles. The detection can be performed at an operating pH of greater than about 5.0 or greater than about 6.0.

In yet another aspect, the disclosure features a kit, which contains mixture of encoded particles, the mixture comprising one or more pluralities of encoded particles, each plurality of particles having a different attached phospho-transfer substrate, the phospho-transfer substrate being identifiable by a particle code; and a detectable phosphomonoester-selective binding agent. The kit can optionally include instructions for detecting a phospho-transfer substrate.

In some embodiments, at least some of the encoded particles can be magnetic.

In some embodiments, the kit can contain more than one plurality of encoded particles. For example, the kit can contain at least two pluralities of encoded particles, each containing different nucleic acid particle codes.

In some aspects, the disclosure provides methods for detecting the presence of (or the activity of) one or more enzymatic activities in a sample. The methods include contacting a sample suspected of containing the activity with a substrate in a under suitable conditions. For example, the substrate contains a phospho-acceptor site specific to the kinase(s) of interest. The substrate can be immobilized on a solid phase before or after contact with the sample. The methods can further include separating the solid phase and contacting the solid phase with a phosphomonoester-selective binding agent and determining if the substrate has been modified based on ability of the phosphomonoester-binding agent to interact with the substrate.

In some aspects, the disclosure provides methods for detecting the presence of (or the activity of) one or more protein or lipid kinases in a sample. The methods include contacting a sample suspected of containing the kinase with a peptide in a phosphorylation reaction mixture under phosphorylation conditions, wherein the peptide comprises a phospho-acceptor site specific to the kinase(s) of interest. In some embodiments, the peptide is immobilized on a solid phase prior to contact with the sample. In some embodiments, the peptide is immobilized on a solid phase surface after contact with the sample. The methods further include separating the solid phase from the phosphorylation reaction mixture and contacting the solid phase with a detectable phosphomonoester-selective binding agent under conditions whereby the detectable phosphomonoester-selective binding agent will bind to the solid phase if the immobilized peptide is phosphorylated. The methods further include separating the solid phase from the unbound detectable phosphomonoester-selective binding agent and detecting the detectable phosphomonoester-selective binding agent bound to the solid phase wherein the presence of the detectable phosphomonoester-selective binding agent bound to the solid phase indicates the presence of the kinase(s) in the sample.

In some aspects, the disclosure provides methods for detecting the presence of (or the activity of) one or more protein phosphatase in a sample. The methods include contacting the sample suspected of containing the phosphatase with a phosphorylated peptide in a phosphatase reaction mixture under dephosphorylation conditions, wherein the peptide comprises a phosphatase recognition site specific to the phosphatase. In some embodiments, the peptide is immobilized on a solid phase prior to contact with the sample. In some embodiments, the peptide is immobilized on a solid phase surface after contact with the sample. The methods further include separating the solid phase from the phosphatase reaction mixture and contacting the solid phase with a detectable phosphomonoester-selective binding agent under conditions whereby the detectable phosphomonoester-selective binding agent will bind to the solid phase if the immobilized peptide is phosphorylated. The methods further include separating the solid phase from the unbound detectable phosphomonoester-selective binding agent and detecting the detectable phosphomonoester-selective binding agent bound to the solid phase wherein the decrease of the detectable phosphomonoester-selective binding agent bound to the solid phase indicates the presence of the phosphatase in the sample.

In some aspects, the disclosure provides methods for detecting the presence of (or the activity of) a phosphodiesterase in a sample. The methods include contacting the sample suspected of containing the phosphodiesterase with cyclic nucleotide (e.g., a cAMP or a cGMP) molecules immobilized on a solid phase in a phosphodiesterase reaction mixture under conditions that allow phosphodiesterase activity. The methods further include separating the solid phase from the phosphorylation reaction mixture and contacting the solid phase with a detectable phosphomonoester-selective binding agent under conditions whereby the detectable phosphomonoester-selective binding agent will bind to the solid phase if the cyclic nucleotide is cleaved by the phosphodiesterase. The methods further include separating the solid phase from the unbound detectable phosphomonoester-selective binding agent and detecting the detectable phosphomonoester-selective binding agent bound to the solid phase wherein the presence of the detectable phosphomonoester-selective binding agent bound to the solid phase indicates the presence of the phosphodiesterase in the sample.

In further aspects, the disclosure provides methods for detecting the presence of (or the activity of) a nucleotide cyclase in a sample. These methods include contacting the sample suspected of containing the nucleotide cyclase with a nucleotide triphosphate, such as an ATP or GTP molecule immobilized on a solid phase in a cyclase reaction mixture under cyclase reaction conditions. The solid phase is next separated from the cyclase reaction mixture, and then contacted with a detectable phosphomonoester-selective binding agent under conditions whereby the detectable phosphomonoester-binding agent will bind to the immobilized nucleotide triphosphate if the immobilized nucleotide triphosphate is not cyclized by a nucleotide cyclase. After separating the solid phase from the unbound detectable phosphomonoester-selective binding agent, the detectable phosphomonoester-selective binding agent bound to the solid phase is detected. A decrease in the detectable phosphomonoester-selective binding agent bound to the solid phase indicates the presence of the nucleotide cyclase in the sample.

In some aspects, the disclosure provides methods for detecting the presence of (or the activity of) one or more kinases in a sample. The methods include contacting a sample suspected of containing one or more protein kinases with a plurality of peptides immobilized on a solid phase in a phosphorylation reaction mixture under phosphorylation conditions, wherein each peptide comprising a phosphoacceptor site specific to at least one of the kinases is immobilized on a separate and distinguishable solid phase. In some embodiments, the plurality of peptides is immobilized on separate and distinguishable solid phases prior to contact with the sample. In some embodiments, the plurality of peptides is immobilized on separate and distinguishable solid phases after contact with the sample. The methods further include separating the solid phases from the phosphorylation reaction mixture and contacting the solid phases with a detectable phosphomonoester-selective binding agent under conditions whereby the detectable phosphomonoester-selective binding agent will bind to the solid phases if the immobilized peptides are phosphorylated. The methods further include separating the solid phases from the unbound detectable phosphomonoester-selective binding agent, and detecting and distinguishing solid phase to which the detectable phosphomonoester-selective binding agent is bound, wherein the binding of the detectable phosphomonoester-selective binding agent to a particular solid phase indicates the presence in the sample of a protein kinase that recognizes the phosphoacceptor site in the peptide immobilized on that solid phase.

In some aspects, the disclosure provides methods for detecting the presence of (or the activity of) one or more phosphatases in a sample. The methods include contacting a sample suspected of containing one or more phosphatases with a plurality of peptides immobilized on a solid phase in a phosphatase reaction mixture under dephosphorylation conditions, wherein the each peptide comprising a phosphatase recognition site specific to at least one of the phosphatases is immobilized on a separate and distinguishable solid phase. In some embodiments, the plurality of peptides is immobilized on separate and distinguishable solid phases prior to contact with the sample. In some embodiments, the plurality of peptide is immobilized on separate and distinguishable solid phases after contact with the sample. The methods further include separating the solid phases from the phosphatase reaction mixture and contacting the solid phases with a detectable phosphomonoester-selective binding agent under conditions whereby the detectable phosphomonoester-selective binding agent will bind to the solid phases if the immobilized peptides are phosphorylated. The methods further include separating the solid phases from the unbound detectable phosphomonoester-selective binding agent, and detecting and distinguishing solid phase to which the detectable phosphomonoester-selective binding agent is bound, wherein the reduction or decrease of binding of the detectable phosphomonoester-selective binding agent to a particular solid phase indicates the presence in the sample of a phosphatase that recognizes the phosphatase recognition site in the peptide immobilized on that solid phase.

In various embodiments of all of the aspects of the disclosure, the solid phase is a bead, such as a magnetic bead. In various embodiments, the detecting step or the detecting and distinguishing step is performed with a flow cytometer or similar device.

In further embodiments, the separate and distinguishable solid phase comprises a tag that is specific for a complementary tag present on the peptide immobilized on the separate and distinguishable solid phase. In particular embodiments, the tag and the complementary tags are each single stranded nucleic acid molecules that are complementary to one another.

In further aspects, the disclosure provides kits for detecting the presence of (or the activity of) one or more kinase, phosphatase, phosphodiesterase, and/or nucleotide cyclase in a sample, comprising at least one set of solid phases, wherein each particle in the set comprises an identical nucleic acid tag, and a detectable phosphomonoester-selective binding agent. In some embodiments, the solid phase is a bead, such as a magnetic bead. In some embodiments, the kit includes more than one set of solid phases, where solid phases in different sets comprise different nucleic acid tags and wherein the sets of solid phases are separate and distinguishable from one another.

All publications, patent applications (including U.S. Ser. No. 60/822,824; and U.S. Ser. No. 60/897,733), patents, and other references mentioned herein are incorporated by reference in their entirety.

BRIEF DESCRIPTION OF THE DRAWINGS

FIG. 28 is a photograph showing the visible color of tubes containing, from left to right, 50 μM pyrocatechol violet alone; 50 μM pyrocatechol-Zn Phos-tag complex; 100 μM phosphopeptide plus 50 μM pyrocatechol-Zn Phos-tag complex; 100 μM unphosphorylated peptide plus 50 μM pyrocatechol-Zn Phos-tag complex; 1.5 mg/ml ovalbumin (a phosphoprotein) plus 50 μM pyrocatechol-Zn Phos-tag complex; and 1.5 mg/ml bovine serum albumin (an unphosphorylated protein) plus 50 μM pyrocatechol-Zn Phos-tag complex.

DETAILED DESCRIPTION

Figure 1:
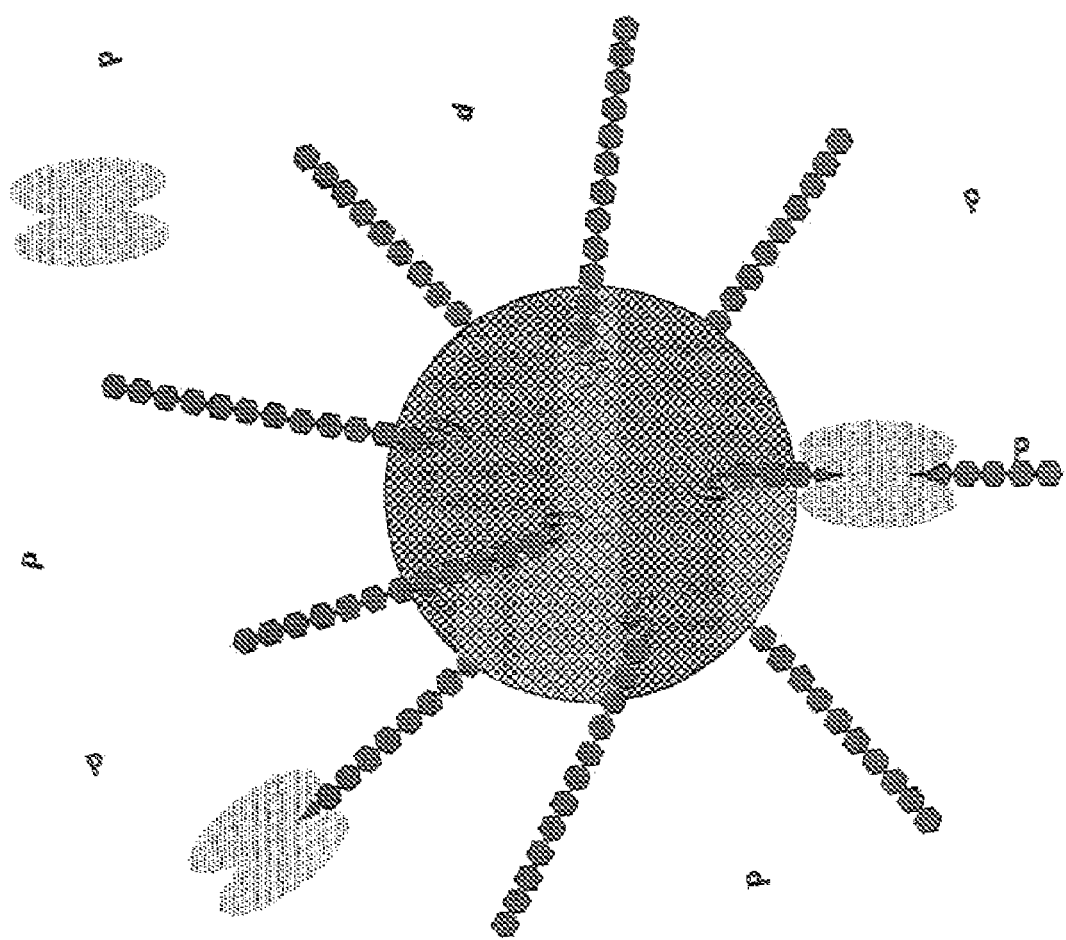
FIG. 1 is a schematic diagram showing a number of peptide or nucleic acid substrates attached to a single bead, where each substrate attached to the same bead has the identical amino acid or nucleic acid sequence. In this non-limiting example, peptide substrates are attached to the bead prior to incubation with a kinase (shown as widened figure eight structures) in a phosphorylation reaction mixture containing free phosphate (e.g., ATP; free phosphate shown as "P").

The disclosure features methods and compositions useful for, inter alia, the detection of phospho-transfer activity in a sample. Thus, the methods and reagents described herein are useful, e.g., for evaluating molecules that participate in signal transduction events.

A phosphomonoester-selective binding agent can be used to determine if a substrate has been modified. For example, the substrate can be immobilized on a solid support such as a particle, e.g., an encoded particle. Increased binding of the phosphomonoester-selective binding agent can indicate an enzymatic activity that catalyzes transfer of phosphates onto a substrate, e.g., a kinase activity. Decreased binding of the phosphomonoester-selective binding agent can indicate an enzymatic activity that catalyzes transfer of phosphates from a substrate, e.g., a phosphatase activity.

In some embodiments, particles are used, for example, to rapidly analyze multiple substrates or multiple samples. In one implementation, a collection of particles is provided. The collection can include individual particles associated with different substrates, e.g., at least 10, 20, 50, or 100 different substrates. For example, an individual particle can include one particular substrate. The collection can include numerous such particles to provide a wide range of different substrates. The collection can be contacted with a sample (e.g., a sample containing an enzymatic activity). Then, the particles can be evaluated for binding of the phosphomonoester-selective binding agent to determine which substrates have been modified by the sample.

In another implementation, encoded particles are used to evaluate multiple samples. The code on the particles can be used to indicate the sample and the substrate being tested. After contacting different particles to samples in parallel (e.g., in different wells of a microtitre plate), the particles can be pooled and analyzed. The coding of the particle can be used to determine if a particular sample caused the modification of a particular substrate.

Phospho-Transfer Activities and Phospho-Transfer Substrates

The methods described herein can be used to evaluate a variety of different phospho transfer activities. Examples of phospho-transfer activities capable of adding a phosphate moiety to a substrate include, e.g., kinase activity such tyrosine kinase, threonine/serine kinase, saccharide kinase, or lipid kinase activity. Exemplary kinases are set forth in the following Examples and include $Ca^{2+}$/Calmodulin Dependent Protein Kinase II.

Phospho-transfer activity capable of removing a phosphate moiety from a substrate can be, e.g., a phosphatase activity. Phosphatase activity can include, e.g., tyrosine-specific phosphatase, threonine/serine phosphatase, dual-specificity phosphatase, saccharide phosphatase, histidine-specific phosphatase, or lipid phosphatase activity. An exemplary phosphatase for use in the methods described herein is Protein Phosphatase 2A (PP2A). Phospho-transfer activities capable of modifying (e.g., cyclizing or decyclizing) a phosphate moiety on a substrate include, e.g., phosphodiesterase (PDE) and nucleotide cyclase activity. PDE's comprise a large group of enzymes organized into 11 distinct families based on biochemical and molecular properties. For example, PDEs include human Phosphodiesterase 3B, human Phosphodiesterase 11A1, human Phosphodiesterase 4A4, human Phosphodiesterase 4D3, and calf spleen Phosphodiesterase (Type II).

Phospho-transfer substrates can be used that are recognized with high affinity and specificity. For example, the substrate can be the cognate substrate of the enzyme, e.g., in vivo. Peptide substrates can be short peptides, e.g., less than 15 or 10 amino acids, or can be contained in a larger protein, e.g., a full length protein or full length domain from a protein (such as a naturally occurring protein). Artificial substrates and mimetics of the cognate substrate can also be used.

Examples of substrates include the following: Forkhead transcription factors or p21$^{WAF}$ (for the kinase Akt); Androgen Receptor (for the phosphatase PP2A); AMP for the nucleotide cyclase adenylate cyclase); and cyclic GMP (cGMP; for the phosphodiesterase cGMP specific phosphodiesterase type 5)(see, e.g., Brunet et al. (1999) Cell 96:857-868; Li et al. (2002) J. Biol. Chem. 277:11352-11361; Yang et al. (2007) Mol. Cell. Biol. 27(9):3390-3404; and Bakre et al. (2000) J. Cell Biochem. 77(1):159-167). Exemplary substrates include polypeptides (e.g., short peptide sequences, large macromolecules, or complexes of one or more polypeptides), nucleic acids (e.g., polymeric or monomeric DNA, RNA, or modified DNA or RNA), lipids, saccharides (e.g., mannose or glucose), small molecule compounds (e.g., steroids, vitamins), or phosphorylated forms of any of the aforementioned (e.g., phosphorylated polypeptides, nucleic acids, saccharides, lipids or small molecules). The phosphorylated forms of the substrates can be cyclic phospho-forms such as cyclic nucleotide monophosphates (e.g., cAMP or cGMP).

In some embodiments, the substrate is attached to a solid support via a heterologous moiety, such as a linker. The heterologous moiety can be one that does not affect interaction between the substrate and the enzyme.

Generally linker moieties can be used to attach any intact substrate to a support. The linker portion, or substrate, can contain a reactive group to facilitate chemical linkage to a support (see below). Alternatively or additionally, the linker portion, or substrate, can contain a moiety recognized by a binding partner (e.g., a first member of a binding pair) that is attached to, or is attachable to, a support. Suitable binding partners are described below.

In the case of a phospho-transfer enzyme capable of adding a phosphate moiety to a substrate, the recognition site is a "phosphoacceptor site," often, this is referred to as the phosphorylation consensus sequence. Biological targets (e.g., proteins and glycoproteins) are typically phosphorylated on tyrosine residues, serine residues, and/or threonine residues. A phosphoacceptor site for a kinase of biological targets thus typically includes a tyrosine, serine, or threonine residue surrounded by additional amino acid residues which help the kinase recognize its site. Many phosphoacceptor sites are known (see, e.g., Kennelly, P. J., and Krebs, E. G. (1991) *J. Biol. Chem.* 266: 15555-15558; Pearson, R. B., and Kemp, B. E. (1991). In T. Hunter and B. M. Sefton (Eds.), *Methods in Enzymology* Vol. 200, (pp. 62-81). San Diego: Academic Press; Roach, P. J. (1991) *J. Biol. Chem.* 266: 14139-14142; Flotow, H. et al. (1990) *J. Biol. Chem.* 265: 14264-14269; Russo, G. L. et al. (1992) *J. Biol. Chem.* 267: 20317-20325; Fiol, C. J. et al. (1990) *J. Biol. Chem.* 265: 6061-6065; Davis, R. J. (1993) *J. Biol. Chem.* 268: 14553-14556; Songyang, Z. et al. (1995) *Nature* 373: 536-539; Geahlen, R. L. and Harrison, M. L. (1990). In B. E. Kemp (Ed.), *Peptides and Protein Phosphorylation*, (pp. 239-253). Boca Raton: CRC Press; and Stevenson, L. M. et al. (2003) *J. Biol. Chem.* 278: 50956-50960. Table I lists some exemplary phosphoacceptor sites (with the phosphorylated amino acid underlined).

TABLE I

| Kinase | Consensus phosphoacceptor site | Specific Phosphoacceptor Sites | Target Protein Containing Specific Phosphoacceptor Site |
|---|---|---|---|
| cAMP-dependent Protein Kinase (PKA, cAPK) | R-X-S/T | YLRRAS̲LAQLT<br>FRRLS̲IST | pyruvate kinase<br>phosphorylase kinase, α chain |
|  | R-R/K-X-S/T | AGARRKAS̲GPP | histone H1, bovine |
| Casein Kinase I (CKI, CK-1) | S(P)-X-X-S/T | RTLS(P)VSS̲LPGL<br>DIGS(P)ES(P)T̲EDQ | glycogen synthase, rabbit muscle<br>$α_{s1}$-casein |
| Casein Kinase II (CKII, CK-2) | S/T-X-X-E | ADS̲ESEDEED<br>LES̲EEEGVPST<br>EDN̲SEDEISNL | PKA regulatory subunit, $R_{II}$<br>p34$^{cdc2}$, human<br>acetyl-CoA carboxylase |
| Glycogen Synthase Kinase 3 (GSK-3) | S̲-X-X-X-S(P) | SVPPS̲PSLS(P)<br>S̲VPPS(P)PSLS(P) | glycogen synthase, human (site 3b)<br>glycogen synthase, human (site 3a) |
| Cdc2 Protein Kinase; CDK2-cyclin A | S/T-P-X-R/K$^c$ | PAKT̲PVK<br>HST̲PPKKKRK | histone H1, calf thymus<br>large T antigen |
| Calmodulin-dependent Protein Kinase II (CaMK II) | R-X-X-S/T<br>R-X-X-S/T-V | NYLRRRLS̲DSN<br>KMARVFS̲VLR | synapsin (site 1)<br>calcineurin |
| Mitogen- activated Protein Kinase (Extracellular Signal-regulated Kinase) (MAPK, Erk) | P-X-S/T-P<br>X-X-S/T-P | PLS̲P<br>PSS̲P<br>VLS̲P | c-Jun<br>cyclin B<br>Elk-1 |

Note:
the S(P) symbol indicate that the serine residues is already phosphorylated.

In the case of a phospho-transfer enzyme capable of recognizing and removing (dephosphorylating) a phosphate moiety on a substrate (e.g., a phosphatase), the recognition site is referred to as the phosphorylation consensus sequence. Of course, a phosphatase recognition site includes a phosphorylated site, such as a phosphorylated serine, phosphorylated threonine, or phosphorylated tyrosine residue. Some non-limiting examples of phosphatase recognition sites include Nterm-RRA(pT)VA-Cterm (where the "pT" is a phosphorylated threonine residue), which is recognized by several serine/threonine phosphatases such as the Protein Phosphatases 2A, 2B and 2C, and N-term-END(pY)INASL-Cterm and Nterm-DADE(pY)LIPQQG-Cterm (where the "pY" are a phosphorylated tyrosine residues) which is recognized by many protein tyrosine phosphatases.

Solid Supports

A phospho-transfer substrate useful in a method described herein can be attached to a solid support, e.g., a porous or non-porous material that is insoluble. The substrate can be associated with the support in variety of ways, e.g., covalently or non-covalently bound. The substrate is generally attached such that it is accessible to the phospho-transfer activities in solution.

A support can be composed of a natural or synthetic material, an organic or inorganic material, such as a polymer, resin, metal or glass, and combinations thereof. Many suitable supports are known in the art and illustratively include, e.g., particles, such as Luminex®-type encoded particles, magnetic particles, and glass particles.

A support useful in a method described herein can have a variety of physical formats, which can include for example, a membrane, column, a hollow, solid, semi-solid, pore or cavity containing particle such as a bead, a gel, a fiber, including a fiber optic material, a sheet, a matrix and sample receptacle. Examples of sample receptacles include sample wells, tubes, capillaries, vials and any other vessel, groove or indentation capable of holding a sample, including those containing membranes, filters, matrices and the like.

A sample receptacle also can be contained on a multi-sample platform, such as a microplate, slide, microfluidics device, array substrate, mass spectrometry sample plate, and the like. Exemplary particles that can be used can have a variety of sizes and physical properties. Particles can be selected to have a variety of properties useful for particular experimental formats. For example, particles can be selected that remain suspended in a solution of desired viscosity or to readily precipitate in a solution of desired viscosity. Particles can be selected for ease of separation from sample constituents, for example, by including purification tags for separation with a suitable tag-binding material, paramagnetic properties for magnetic separation, and the like.

In some embodiments, encoded particles are used. Each particle includes a unique code (such as a bar code, luminescence code, fluorescence code, a nucleic acid code, and the like). Encoding can be used to provide particles for evaluating different enzymatic activities in a single sample. Such methods can include contacting a sample to a mixture of encoded particles, and then contacting the encoded particles to detectably labeled tags for evaluating the enzymatic reacting. For example, the detectable tags can be used to detect the presence or amount of modified substrates (e.g., support-bound products, or free products). The code is embedded (for example, within the interior of the particle) or otherwise attached to the particle in a manner that is stable through hybridization and analysis. The code can be provided by any detectable means, such as by holographic encoding, by a fluorescence property, color, shape, size, weight, light emission, quantum dot emission and the like to identify particle and thus the capture probes immobilized thereto. Encoding can also be the ratio of two or more dyes in one particle that is different than the ratio present in another particle. For example, the particles may be encoded using optical, chemical, physical, or electronic tags. Examples of such coding technologies are optical bar codes fluorescent dyes, or other means.

In some embodiments, the particle code is a nucleic acid, e.g., a single stranded nucleic acid. For example, a solid support such as a particle can be attached to a single- or double-stranded nucleic acid, each strand being about 10 nucleotides (e.g., about 15 nucleotides, about 20 nucleotides, about 25 nucleotides, about 30 nucleotides, about 35 nucleotides, about 40 nucleotides, about 50 nucleotides, about 75 nucleotides, about 100 nucleotides, or about 150 or more nucleotides) in length.

Different encoded particles can be used to evaluate a number of different enzymatic activities in parallel, so long as the encoding can be used to identify the intact substrate on a particular particle, and hence the activity being evaluated. A sample can be contacted with a plurality of such coded particles. When the particles are evaluated, e.g., using a fluorescent scanner, the particle code is read as is the fluorescence associated with the particle from any probe used to evaluate modification of the intact substrate associated with the particles.

One exemplary platform utilizes mixtures of fluorescent dyes impregnated into polymer particles as the means to identify each member of a particle set to which a specific capture probe has been immobilized. Another exemplary platform uses holographic barcodes to identify cylindrical glass particles. For example, Chandler et al. (U.S. Pat. No. 5,981,180) describes a particle-based system in which different particle types are encoded by mixtures of various proportions of two or more fluorescent dyes impregnated into polymer particles. Soini (U.S. Pat. No. 5,028,545) describes a particle-based multiplexed assay system that employs time-resolved fluorescence for particle identification. Fulwyler (U.S. Pat. No. 4,499,052) describes an exemplary method for using particle distinguished by color and/or size. U.S. Publication Nos. 2004-0179267, 2004-0132205, 2004-0130786, 2004-0130761, 2004-0126875, 2004-0125424, and 2004-0075907 describe exemplary particles encoded by holographic barcodes.

U.S. Pat. No. 6,916,661 describes polymeric microparticles that are associated with nanoparticles that have dyes that provide a code for the particles. The polymeric microparticles can have a diameter of less than one millimeter, e.g., a size ranging from about 0.1 to about 1,000 micrometers in diameter, e.g., 3-25 µm or about 6-12 µm. The nanoparticles can have, e.g., a diameter from about 1 nanometer (nm) to about 100,000 nm in diameter, e.g., about 10-1,000 nm or 200-500 nm.

Other suitable solid-supports include, e.g., substrate arrays such as nucleic acid or peptide arrays. Like encoded particles, an important characteristic of an array is that all substrates (of a plurality of substrates) can be immobilized at predetermined positions such that each substrate can be identified by its position. Exemplary arrays for use in detection methods described herein include, e.g., protein and nucleic acid arrays (see, e.g., U.S. Pat. Nos. 6,197,599; 5,902,723; and 5,871,928; the disclosures of each of which are incorporated herein by reference in their entirety).

A phospho-transfer substrate can be covalently or non-covalently bound to a support. A variety of chemical reactions useful for covalently attaching a substrate to a support are well known to those skilled in the art (see, for example, Hartmann et al. (2002) J. Mater. Res. 17(2):473-478). Illustrative examples of functional groups useful for covalent attachment of substrates to a support include alkyl, Si—OH, carboxy, carbonyl, hydroxyl, amide, amine, amino, ether, ester, epoxides, cyanate, isocyanate, thiocyanate, sulflhydryl, disulfide, oxide, diazo, iodine, sulfonic or similar groups having chemical or potential chemical reactivity. Illustrative examples of binding partners useful for non-covalent attachment of substrates to a support include antibodies, antibody-like materials, and agents, e.g., that are capable of binding to antibodies such as, but not limited to, staphylococcal protein A or protein G. In some embodiments, e.g., where the particle code is a nucleic acid, the phospho-transfer substrate can contain, or be, a nucleic acid that is complementary to the particle code nucleic acid. For example, a peptide substrate can be joined to a nucleic acid, which nucleic acid is complementary to a nucleic acid bound to a particle, such that the nucleic acids bind and tether the substrate to the particle.

Phosphomonoester-Selective Binding Agents

Phosphomonoester-selective binding agents are compounds that selectively binds to phosphate monoesters, e.g., phosphorylated amino acid residues. Examples of phosphomonoester-selective binding agents include small-molecule phosphomonoester-selective binding agents with a molecular weight of 1-2,500 daltons. Phosphomonoester-selective binding agents can also be macromolecules such as antibodies or antibody fragments (e.g., antigen-binding fragments) that selectively bind to a phosphate monoester.

Small molecule phosphomonoester-selective binding agents, in some embodiments, can have, or contain, the structure as depicted in Formula I:

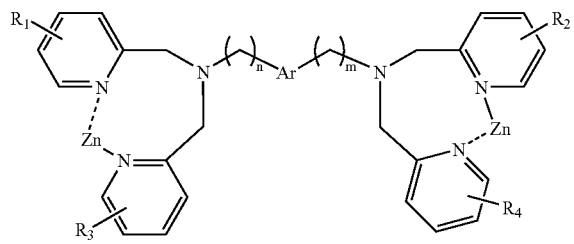

wherein each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group, each n and m are independently 0 or 1; and Ar aryl.

In some embodiments, each n and m can be 0 or each n and m can be 1. In some embodiments, each of $R_1$, $R_2$, $R_3$, and $R_4$ are H. In some embodiments, Ar is anthracene. In some embodiments, Ar is:

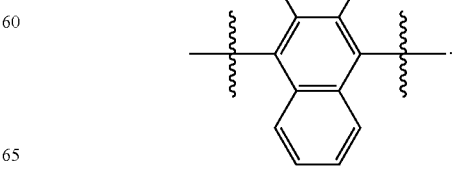

In some embodiments, each of R1, R2, R3, and R4 are H; n and m are each 1; and Ar is:

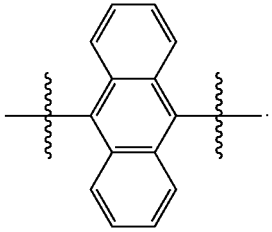

The term "halo" or "halogen" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). The terms "arylalkyl" or "aralkyl" refer to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The terms "aminocarbonyl," alkoxycarbonyl," hydrazinocarbonyl, and hydroxyaminocarbonyl refer to the radicals —C(O)NH$_2$, —C(O)O(alkyl), —C(O)NH$_2$NH$_2$, and —C(O)NH$_2$NH$_2$, respectively.

As used herein, "haloalkyl" refers to an alkyl group in which one or more of the hydrogen atoms are replaced by halogen. Such groups include, but are not limited to, chloromethyl, trifluoromethyl and 1-chloro-2-fluoroethyl.

As used herein, "carboxy" refers to a divalent radical, —C(O)O—.

As used herein, "carbomoyl" refers to —C(O)NH$_2$.

Additional phosphomonoester-selective binding agents and methods (e.g., synthetic methods) for preparing such agents are described in, e.g., Koike et al., U.S. Patent Publication No. 2005-0038258 published Feb. 17, 2005; Koike et al., U.S. Patent Publication No. 2004-0198712 published Oct. 7, 2004; Koike et al., European Patent Publication No. 1614706 published Jan. 11, 2006; Koiket al., European Patent Publication No. 1602923 published Dec. 7, 2005; Yashiro et al. (1995) J. Chem. Soc. Commun. 17: 1793-1794; Yamaguchi et al. (2001) Chem. Commun. 4: 375-376; U.S. Ser. No. 60/822,824; and U.S. Ser. No. 60/897,733; the disclosures of each of which are incorporated herein in their entirety.

In some embodiments, the phosphomonoester-selective binding agent has the Formula II:

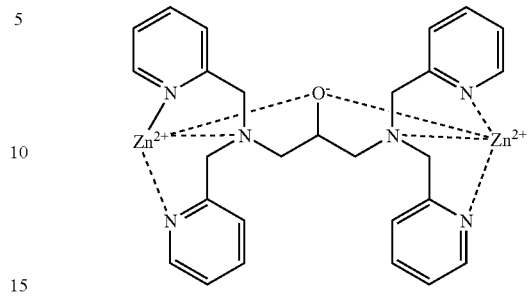

Exemplary small molecule phosphomonoester-selective binding agents include the Phos-Tag™ reagent (Perkin Elmer, Boston, Mass.) or the PhosphoQUANTI reagent (Wako Pure Chemical Industries, Ltd., Richmond, Va.).

Figure 3:
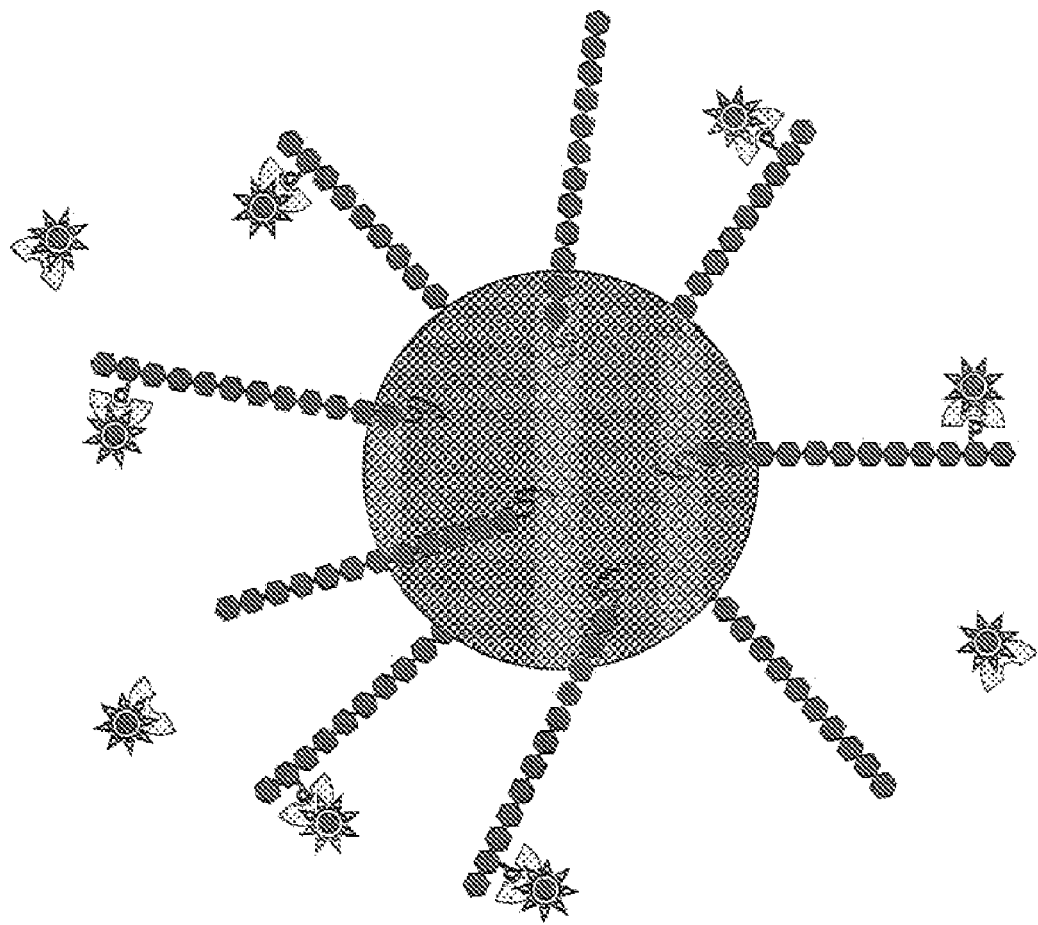
FIG. 3 is a schematic diagram showing the bead-immobilized substrates bound to a detectable phosphomonoester-selective binding agent of the disclosure.

The particles (upon which can be immobilized phosphotransfer substrates) can be exposed to a detectable phosphomonoester-selective binding agent (see FIG. 3) in a binding reaction mixture having a pH value of greater than about 5. The particles can be exposed to a detectable phosphomonoester-selective binding agent (see FIG. 3) in a binding reaction mixture having a pH value of greater than about 6. Thus, detection of a phosphate moiety (e.g., a phosphorylated substrate) can be performed at a pH range of about 6.0 to 8.0 (e.g., about between pH 6.0 and pH 6.5, about between pH 6.0 and pH 7.0, about between pH 6.5 and pH 7.0, about between pH 6.5 and pH 7.5, about between pH 6.8 and pH 7.5; about between pH 6.9 and pH 7.2; about between pH 7.0 and pH 7.5; about between pH 7.0 and pH 8.0; or about between pH 7.5 and pH 8.0).

In some embodiments, the phosphomonoester-selective binding agent is not a large molecule phosphomonoester-selective binding agent such as an antibody (e.g., a monoclonal antibody, polyclonal antibody, or an antibody fragment (e.g., antigen-binding fragments of antibodies)). As used herein, the term "antibody fragment" refers to an antigen-binding fragment, e.g., Fab, F(ab')2, Fv, and single chain Fv (scFv) fragments. An scFv fragment is a single polypeptide chain that includes both the heavy and light chain variable regions of the antibody from which the scFv is derived. In addition, diabodies [Poljak (1994) Structure 2(12):1121-1123; Hudson et al. (1999) J. Immunol. Methods 23(1-2): 177-189, the disclosures of both of which are incorporated herein by reference in their entirety] and intrabodies [Huston et al. (2001) Hum. Antibodies 10(3-4):127-142; Wheeler et al. (2003) Mol. Ther. 8(3):355-366; Stocks (2004) Drug Discov. Today 9(22): 960-966, the disclosures of all of which are incorporated herein by reference in their entirety] can be used in the methods described herein.

In some embodiments, the phosphomonoester-selective binding agent is not a calcium ion indicator dye (e.g., induced to bind trivalent cations). Calcium ion indicator dyes bind trivalent cations, such as $Fe^{3+}$ or $Ga^{3+}$, and are described in, e.g., Agnew et al., published U.S. Patent Application No. 20040171034 Compositions and methods for detection and isolation of phosphorylated molecules; Schulenberg B, Aggeler R, Beechem J M, Capaldi R A, Patton W F. Analysis of steady-state protein phosphorylation in mitochondria using a novel fluorescent phosphosensor dye. *J Biol Chem.* 2003 Jul. 18; 278(29):27251-5; Martin K, Steinberg T H, Goodman T, Schulenberg B, Kilgore J A, Gee K R, Beechem J M, Patton W F. Strategies and solid-phase formats for the analysis of protein and peptide phosphorylation employing a novel fluorescent phosphorylation sensor dye. *Comb Chem High Throughput Screen.* 2003 June; 6(4):331-9; Steinberg T H, Agnew B J, Gee K R, Leung W Y, Goodman T, Schulenberg B, Hendrickson J, Beechem J M, Haugland R P, Patton W F. Global quantitative phosphoprotein analysis using Multiplexed Proteomics technology. *Proteomics.* 2003 July; 3(7):1128-44; Martin K, Steinberg T H, Cooley L A, Gee K R, Beechem J M, Patton W F. Quantitative analysis of protein phosphorylation status and protein kinase activity on microarrays using a novel fluorescent phosphorylation sensor dye. *Proteomics.* 2003 July; 3(7):1244-55; and Schulenberg B, Goodman T N, Aggeler R, Capaldi R A, Patton W F. Characterization of dynamic and steady-state protein phosphorylation using a fluorescent phosphoprotein gel stain and mass spectrometry. *Electrophoresis.* 2004 August; 25(15):2526-32; the disclosures of each of which are incorporated herein by reference in their entirety.

By "detectable" is meant that a phosphomonoester-selective binding agent is able to be detected. In some embodiments, the phosphomonoester-selective binding agent is made detectable by being attached (via a covalent or non-covalent chemical bond) with a detectable label, such as a fluorochrome, a colored dye, or a detectable isotope (e.g., non-radioactive or radioactive). Fluorochromes accept light energy at a given wavelength and re-emit it at a different (typically higher) wavelength and include, without limitation, fluorescein, rhodamine, phycoerythrin, Cyanine-5, and Allophycocyanin. Non-limiting colored dyes include thiazin dyes, oxazin dyes, phthalocyanine dyes, and safranin dyes. Non-limiting detectable isotopes include deuterium (a 'heavy' form of hydrogen), $^{13}$C, $^{15}$N, or the radioactive isotopes of atoms, such as $^{3}$H, $^{14}$C or $^{35}$S. In some embodiments, a phosphomonoester-selective binding agent described herein is made detectable by being attached (via a covalent or non-covalent bond) to a molecule which can be readily detected. Non-limiting examples of such molecules include haptens and antigens (which can be detected by detectable antibodies that specifically recognize the hapten or antigen), avidin (or streptavidin) or biotin, which can be detected by detectable (e.g., phycoerythrin-labeled) biotin or avidin (or streptavidin), respectively.

Samples

A sample can be any composition. The content of the sample can be known or unknown. In many cases, a sample contains or is suspected of containing one or more enzymes. For example, a sample can be derived from an organism or man-made source of enzyme. A sample can be, e.g., one containing one or more enzymes in a known quantity or with a known activity.

A sample can be, for example, a specimen obtained from an individual or can be derived from such a specimen. For example, a sample can be a tissue section obtained by biopsy, or cells that are placed in or adapted to tissue culture. A sample can also be, or contain, a biological fluid specimen such as urine, blood, plasma, serum, saliva, semen, sputum, cerebral spinal fluid, tears, mucus, sweat, milk, semen, and the like. Biological samples can also be, or contain, fluid from ulcers or other surface eruptions such as blisters and abscesses or can be extracts of tissues from biopsies of normal, malignant, or suspect tissues. A sample can be further fractionated, if desired, to a fraction containing particular components or cell types. For example, a blood sample can be fractionated into serum or into fractions containing particular types of blood cells such as red blood cells or white blood cells (leukocytes). If desired, a sample can be a combination (pool) of samples from an individual such as a combination of a tissue and fluid sample, and the like.

A sample can be processed to facilitate detection of enzymes. For example, if the sample includes cells or other biological structures, the sample can be treated with freeze/thaw treatment, drying and rehydrating, a dounce, detergent or other methods. Releasing or solubilizing enzymes can also be used provided they do not interfere with the assay, e.g., by interfering with the activity of a phospho-transfer enzyme of interest.

For diagnostic purposes, the sample can be obtained from body fluids and tissues in which particular enzymes being tested are typically expressed.

Samples can be treated with customary care to preserve enzymatic activity. Suitable methods for obtaining samples that preserve the activity or integrity of enzymes in the sample are well known to those skilled in the art. Such methods include the use of appropriate buffers and/or inhibitors, including nuclease, protease and phosphatase inhibitors that preserve or minimize changes in enzymes in the sample. Such inhibitors include, for example, chelators such as ethylenediamne tetraacetic acid (EDTA), ethylene glycol bis(P-aminoethyl ether) N,N,N1,N1-tetraacetic acid (EGTA), protease inhibitors such as phenylmethylsulfonyl fluoride (PMSF), aprotinin, leupeptin, antipain and the like, and phosphatase inhibitors such as phosphate, sodium fluoride, vanadate and the like. Inhibitors can be chosen such that they do not interfere with or only minimally adversely affect the enzymatic activity of interest. For example, if the enzymatic activity to be detected is a protease, methods for obtaining samples that preserve the activity or integrity of the enzyme would not include protease inhibitors that adversely affect the particular protease activity. Appropriate buffers and conditions for enzyme-containing samples are well known (see, for example, Ausubel et al. Current Protocols in Molecular Biology (Supplement 47), John Wiley & Sons, New York (1999); Harlow and Lane, Antibodies: A Laboratory Manual (Cold Spring Harbor Laboratory Press (1988); Harlow and Lane, Using Antibodies: A Laboratory Manual, Cold Spring Harbor Press (1999); Tietz Textbook of Clinical Chemistry, 3rd ed. Burtis and Ashwood, eds. W.B. Saunders, Philadelphia, (1999)).

A sample can be processed to eliminate or minimize the presence of interfering substances, as appropriate. If desired, a sample can be fractionated by a variety of methods well known to those skilled in the art, including subcellular fractionation, and chromatographic techniques such as ion exchange, hydrophobic and reverse phase, size exclusion, affinity, hydrophobic charge-induction chromatography, and the like (Ausubel et al. supra, 1999; Scopes, Protein Purification: Principles and Practice, third edition, Springer-Verlag, New York (1993); Burton and Harding, J. Chromatogr. A 814:71-81 (1998)).

For use in a method described herein, a sample can be in a variety of physical states. For example, a sample can be a liquid or solid, can be dissolved or suspended in a liquid, can be in an emulsion or gel, and can be absorbed onto a material. As a non-limited example, a sample can be a liquid blood sample, liquid serum sample, liquid white blood cell sample, dried blood, serum, or white cell sample, or such a sample absorbed onto a paper or polymer substrate.

The methods described herein are carried out under conditions that allow an enzyme to act on a substrate. Conditions under which proteins retain activity are well known to those skilled in the art and generally include roughly physiologically salt levels, a buffering agent, and a temperature in the range of 4-37° C. For a chosen enzyme, a sample can be adjusted or placed into a solution or environment to have a specified characteristic such as a specified pH (e.g., a pH of about 7.0), salt concentration, surfactant property, viscosity and the like. The ability of an enzyme to act on a substrate can be improved, enhanced and/or stabilized in the presence of sample ingredients such as inorganic salts, alcohols, detergents and surfactants, if desired.

Methods of Detecting Phospho-Transfer Activities

Described herein are methods and compositions useful for detecting one or more phospho-transfer activities in a sample. The methods generally include the steps of contacting a sample with a phospho-transfer substrate attached to a solid-phase (e.g., an encoded particle), wherein the phospho-transfer substrate comprises a recognition site specific to the phospho-transfer activity (e.g., the activity possessed by a phospho-transfer enzyme). The methods can be used to, e.g., determine the substrate specificity of one or more enzymatic activities; (ii) to identify compounds capable of modifying one or more phospho-transfer activities; (iii) optimize reaction conditions for one or more phospho-transfer activities, or (iv) identify one or more phospho-transfer activities (e.g., identify an unknown kinase activity in a sample). In some embodiments, a method described herein can be used to detect the presence, or absence, of a phospho-transfer activity associated with disease. For example, the presence of a kinase associated with cancer (e.g., Aurora kinase, Akt, BCR-Abl, or RET/PTC) in a biological sample can be detected using any of the methods described herein.

In some embodiments, suitable conditions (e.g., phosphorylation, dephosphorylation, phosphodiesterase, or nucleotide cyclase conditions) under which a phospho-transfer reaction can occur include pH ranges of greater than 5, or greater than 6. Thus, the reactions can be performed at a pH range of about 6.0 to 8.0 (e.g., about between pH 6.0 and pH 6.5, about between pH 6.0 and pH 7.0, about between pH 6.5 and pH 7.0, about between pH 6.5 and pH 7.5, about between pH 6.8 and pH 7.5; about between pH 6.9 and pH 7.2; about between pH 7.0 and pH 7.5; about between pH 7.0 and pH 8.0; or about between pH 7.5 and pH 8.0).

Examples of specific phospho-transfer activities and methods for detecting their activity are reviewed in the following sections.

Kinase Activity. The disclosure provides a method for detecting the presence of a kinase in a sample, the activity of that kinase, and/or the incubation conditions appropriate for kinase activity.

One non-limiting example is as follows. A solid phase (such the bottom of a well or tube, the surface of a slide or a Petri dish, or a bead or a particle such as an encoded particle) is contacted with a substrate, wherein the substrate is subsequently immobilized on the solid phase. For example, as shown in FIG. 1, numerous identical peptide substrates having a phosphoacceptor site recognized by a specific kinase are immobilized on an encoded particle.

After the substrate is immobilized on the particle, the particle (one or more particles, which may be in approximately known numbers) can then be exposed to a sample (e.g., a sample containing a kinase activity that recognizes the recognition site (e.g., phosphoacceptor site) contained in the substrate) under phosphorylation conditions. As used herein, by "phosphorylation reaction mixture" is meant that a reaction mixture contains components in which a kinase activity, if present in the reaction mixture, is able to phosphorylate a substrate (i.e., containing a recognition site, in this case, a phosphoacceptor site for the kinase activity) present in the reaction mixture. Such a phosphorylation reaction mixture contains components including, without limitations, ATP, divalent cation such as magnesium or manganese and suitable aqueous buffer. Exemplary phosphorylation conditions are also detailed in the accompanying Examples.

Figure 2:
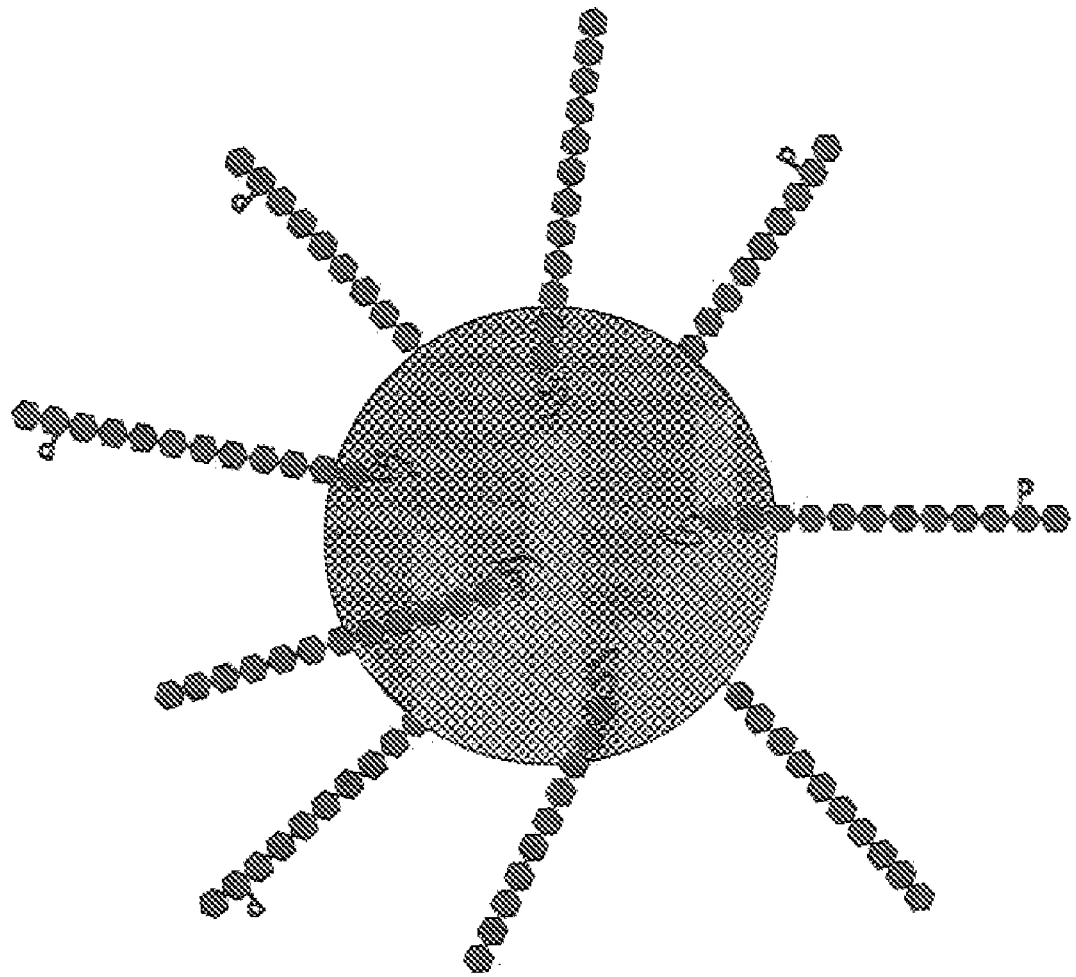
FIG. 2 is a schematic diagram showing the bead-immobilized substrates following removal of the kinase and unbound phosphate.

As FIG. 2 shows, if the sample contains a kinase activity that recognizes the phosphoacceptor site in the substrate, then some or all of the substrates bound to the beads will become phosphorylated. For example, under appropriate incubation conditions, the number of phosphorylated peptides will be approximately proportional to the concentration of the specific kinase. The particles are then washed to remove the free kinase and any other components of the phosphorylation reaction mixture (e.g., free ATP).

Following washing, the particles are then exposed to a detectable phosphomonoester-selective binding agent (see FIG. 3) under conditions whereby the detectable phosphomonoester-binding agent will bind to the particles if peptides immobilized on the particles are phosphorylated. The phospho-monoester binding agent can be any of those described herein.

After contacting the particle-immobilized peptide substrates with the detectable phosphomonoester-selective binding agent and allowing the agent to bind the phosphorylated peptide substrates (if present), the excess detectable phosphomonoester-selective binding agent is washed away, and a signal indicative of the number of phosphorylated peptides is read, for example on a flow cytometric instrument such as a Luminex xMAP 200 instrument (commercially available from the Luminex Corp., Austin, Tex.). In some embodiments, the phosphomonoester-selective binding agent is labeled with phycoerythrin, which is easily read by the Luminex xMAP 200 instrument.

Generally, an increase in the amount of the detectable phosphomonoester-selective binding agent bound to the phospho-transfer substrate contacted with the sample as compared to the amount bound to the phospho-transfer substrate not contacted with the sample indicates the presence of a kinase activity in the sample. Thus, the method includes contacting a sample containing the kinase (or suspected of containing a kinase) with a substrate (e.g., a peptide substrate) in a phosphorylation reaction mixture, wherein the substrate comprises a phosphoacceptor site specific to the kinase. In some embodiments, the substrate is immobilized on a solid phase surface prior to contact with the sample in a phosphorylation reaction mixture.

In some embodiments, the substrate can immobilized on a solid phase surface after contacting the substrate with the sample in a phosphorylation reaction mixture. The substrate immobilized on the solid phase is separated from the sample, and then contacted with a detectable phosphomonoester-selective binding agent. In some embodiments, the substrate is contacted with the detectable phosphomonoester-selective binding agent prior to immobilizing the peptide on a solid phase. The presence of the detectable phosphomonoester-selective binding agent bound to the peptide indicates the presence of the kinase in the sample.

As described above, where the kinase can autophosphorylate, the substrate can be the kinase itself.

Phosphatase Activity. The methods described herein also relate to the detection and/or identification of a phosphatase. The methods can include contacting a sample with a phosphorylated substrate under dephosphorylation conditions, wherein the phosphorylated substrate comprises a recognition site specific to the phosphatase. As above, substrate can be immobilized on a solid phase prior to contact with the sample or immobilized on a solid phase surface after contact with the sample.

The methods further includes separating the solid phase from the phosphatase reaction mixture and contacting the solid phase with a detectable phosphomonoester-selective binding agent under conditions whereby the detectable phosphomonoester-binding agent will bind to the solid phase if the immobilized peptide is phosphorylated. After separating the immobilized peptide from the unbound detectable phosphomonoester-selective binding agent the detectable phosphomonoester-selective binding agent bound to the immobilized peptide is detected. A decrease in the detectable phosphomonoester-selective binding agent bound to the immobilized peptide indicates the presence of the phosphatase in the sample.

Exemplary dephosphorylation conditions are set forth in the accompanying Examples.

Phosphodiesterase Activity. Also provided are methods for detecting the presence of a phosphodiesterase in a sample. By "phosphodiesterase" is meant an enzyme that catalyzes the hydrolysis of phosphodiester bonds. For example, a phosphodiesterase can cleave a cAMP into AMP.

The methods for detecting a phosphodiesterase include, e.g., contacting the sample suspected of containing the phosphodiesterase with a cyclic nucleotide, such as a cAMP or a cGMP molecule immobilized on a solid phase in a phosphodiesterase reaction mixture under conditions that allow phosphodiesterase activity. The methods further include separating the solid phase from the phosphorylation reaction mixture and contacting the solid phase with a detectable phosphomonoester-selective binding agent under conditions whereby the detectable phosphomonoester-binding agent will bind to the solid phase if the cyclic nucleotide is cleaved by the phosphodiesterase. The methods can further include separating the solid phase from the unbound detectable phosphomonoester-selective binding agent and detecting the detectable phosphomonoester-selective binding agent bound to the solid phase wherein the presence of the detectable phosphomonoester-selective binding agent bound to the solid phase indicates the presence of the phosphodiesterase in the sample.

Numerous purified phosphodiesterases are commercially available. For example, recombinant human Phosphodiesterase 3B, recombinant human Phosphodiesterase 11A1, recombinant human Phosphodiesterase 4A4, recombinant human Phosphodiesterase 4D3, and calf spleen Phosphodiesterase (Type II) are commercially available from the Calbiochem branch of EMD Biosciences, San Diego, Calif. Such enzymes can be used in the methods described herein as, e.g., positive controls.

Nucleotide Cyclase Activity. Nucleotide cyclases are enzymes that catalyze the formation of a cyclic nucleotide from a non-cyclic nucleotide. For example, adenylate cyclase catalyzes the formation of cyclic AMP (cAMP) from ATP. The methods described herein can be employed to detect the presence or the activity of a nucleotide cyclase.

Accordingly, the invention provides methods for detecting the presence of a nucleotide cyclase in a sample. These methods include contacting the sample suspected of containing the nucleotide cyclase with nucleotide triphosphate, such as an ATP or GTP molecule, immobilized on a solid phase in a cyclase reaction mixture under cyclase reaction conditions. Cyclase reaction mixtures can contain components including, without limitations, free phosphate (e.g., ATP, GTP, or ADP). Non-limiting cyclase reaction conditions include a pH which allows the activity of the nucleotide cyclase and a temperature which allows the activity of the nucleotide cyclase. In some embodiments, cyclase reaction conditions include having a pH of about 7.0 and a temperature of between about 25° C. and about 40° C.

The solid phase can be separated from the cyclase reaction mixture, and then contacted with a detectable phosphomonoester-selective binding agent under conditions whereby the detectable phosphomonoester-selective binding agent will bind to the immobilized ATP if the immobilized nucleotide triphosphate is not cyclized by a nucleotide cyclase. After separating the solid phase from the unbound detectable phosphomonoester-selective binding agent, the detectable phosphomonoester-selective binding agent bound to the solid phase is detected. A decrease in the detectable phosphomonoester-selective binding agent bound to the solid phase indicates the presence of the nucleotide cyclase in the sample.

Multiplex Assays

Figure 4:
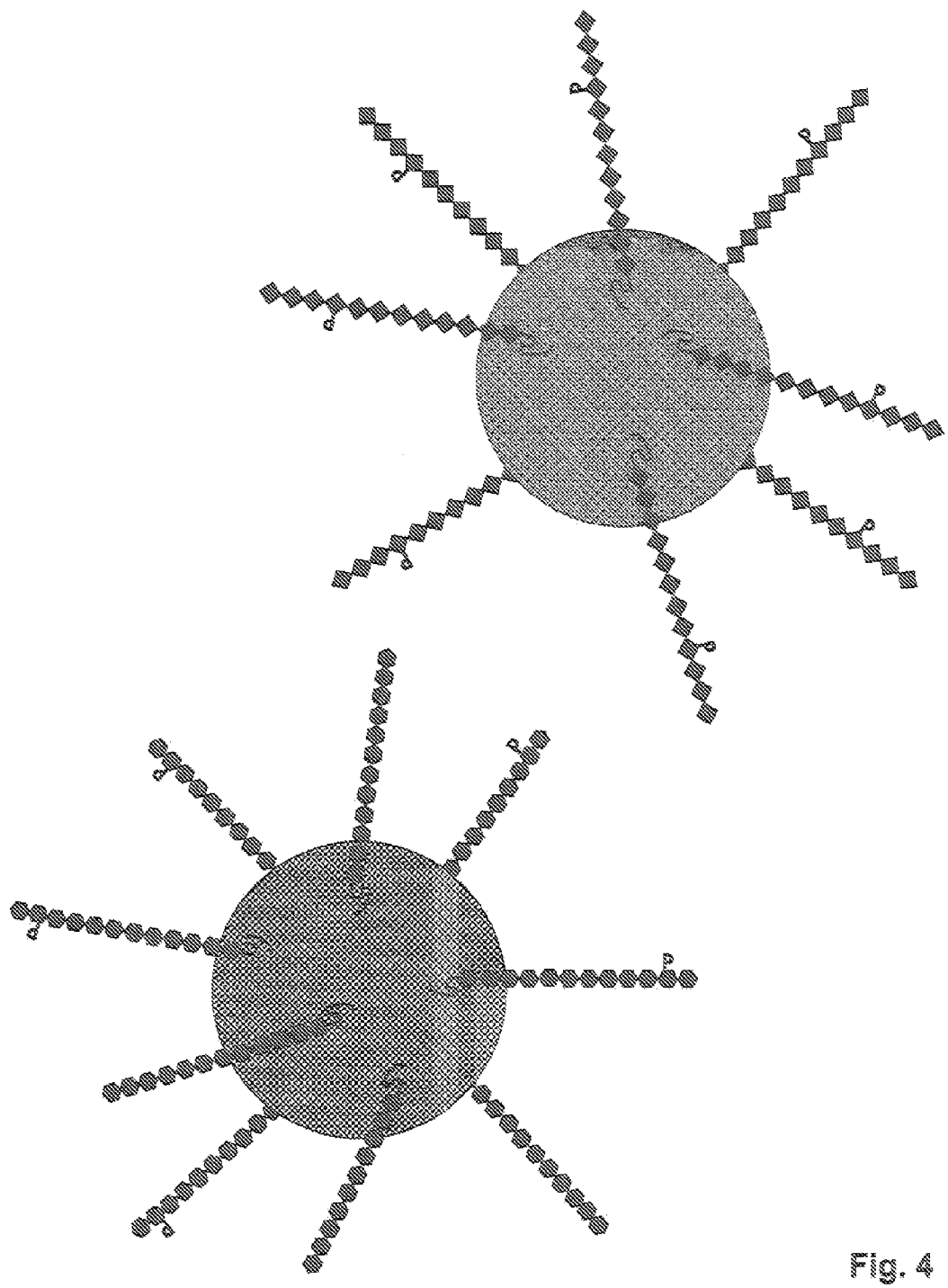
FIG. 4 is a schematic diagram showing two different beads, where the substrates bound to one bead have a different sequence than the substrates bound to a second bead. In this exemplary figure, the first substrate is depicted with diamonds, and the second substrate is depicted with hexagons.

Also featured are multiplex assay methods to detect more than one phospho-transfer activities (e.g., more than one kinase, phosphatase, nucleotide cyclase, or phosphodiesterase activity) simultaneously or, e.g., to determine the substrate specificity of a phospho-transfer activity. For example, as shown in FIG. 4, a set of encoded particles is used. Subsets of particles, where each subset member is encoded with the same particle identification (ID) code (such as a bar code), each have different kinase substrates (in this case peptide substrate) immobilized on them. These particles can be prepared using standard methods such as those described herein. As the target kinases are each specific to the phosphoacceptor site contained in only one of the peptide substrates, the plurality of assays can be carried out simultaneously. For example, a sample containing two kinase activities (A and B) can be contacted with a mixture of encoded particles. The mixture of encoded particles comprises one or more pluralities of encoded particles, each plurality of particles having a different attached kinase substrate, the kinase substrate being identifiable by a particle code, and each different kinase substrate containing a phosphoacceptor site for kinase A or kinase B.

Figure 5:
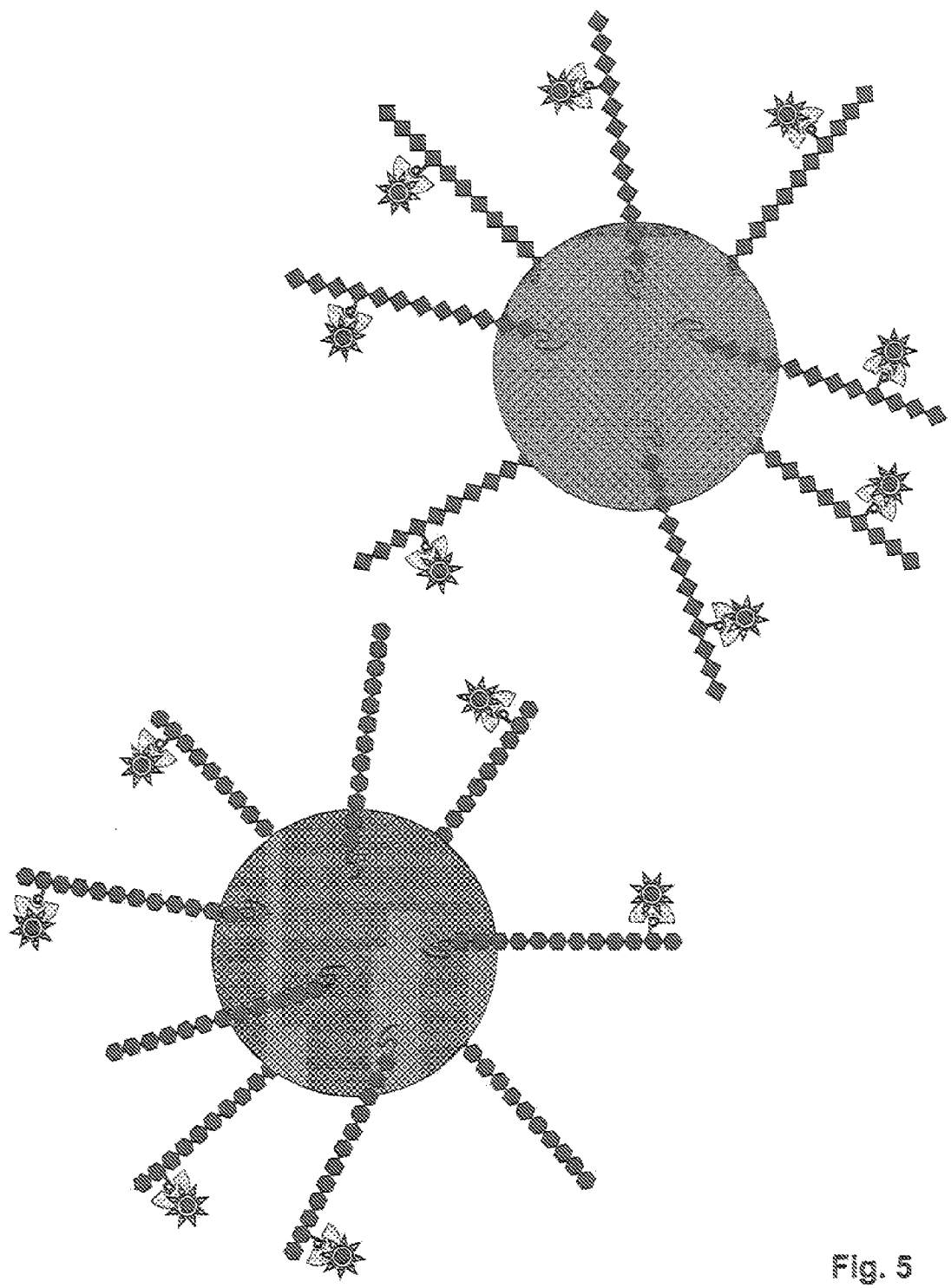
FIG. 5 is a schematic diagram showing the recognition of the phosphorylated residues on the substrates attached to both beads by the detectable phosphomonoester-selective binding agent of the disclosure.

As FIG. 5 shows, as described above where just one type of bead is employed, the multiplex bead set is washed after incubation with the sample and then labeled with a detectable phosphomonoester-selective binding agent. After a final wash, the particles are read in a detection instrument that both detects the encoded identification of the particle and also quantifies the signal from the detectable binding agent. An exemplary instrument is the Luminex xMAP 200™ (Luminex Corporation, Austin, Tex.).

In some embodiments, the substrates are immobilized on a plurality of solid phases prior to contact with the sample in a phosphorylation reaction mixture, wherein substrates having different sequences are immobilized on different solid phases and wherein the substrates immobilized on the same solid phase have the same sequence. Further, in some embodiments, the substrates are immobilized on solid phases after contacting the substrates with the sample in a phosphorylation reaction mixture. The substrates immobilized on the solid phases are separated from the sample, and then contacted with a detectable phosphomonoester-selective binding agent. In some embodiments, the substrates are contacted with the detectable phosphomonoester-selective binding agent prior to immobilizing the on a solid phase. The presence of the detectable phosphomonoester-selective binding agent bound to a particular solid phase indicates the presence in the sample of a kinase that recognizes a phosphoacceptor site present in the substrates immobilized on that particular solid phase.

Figure 6:
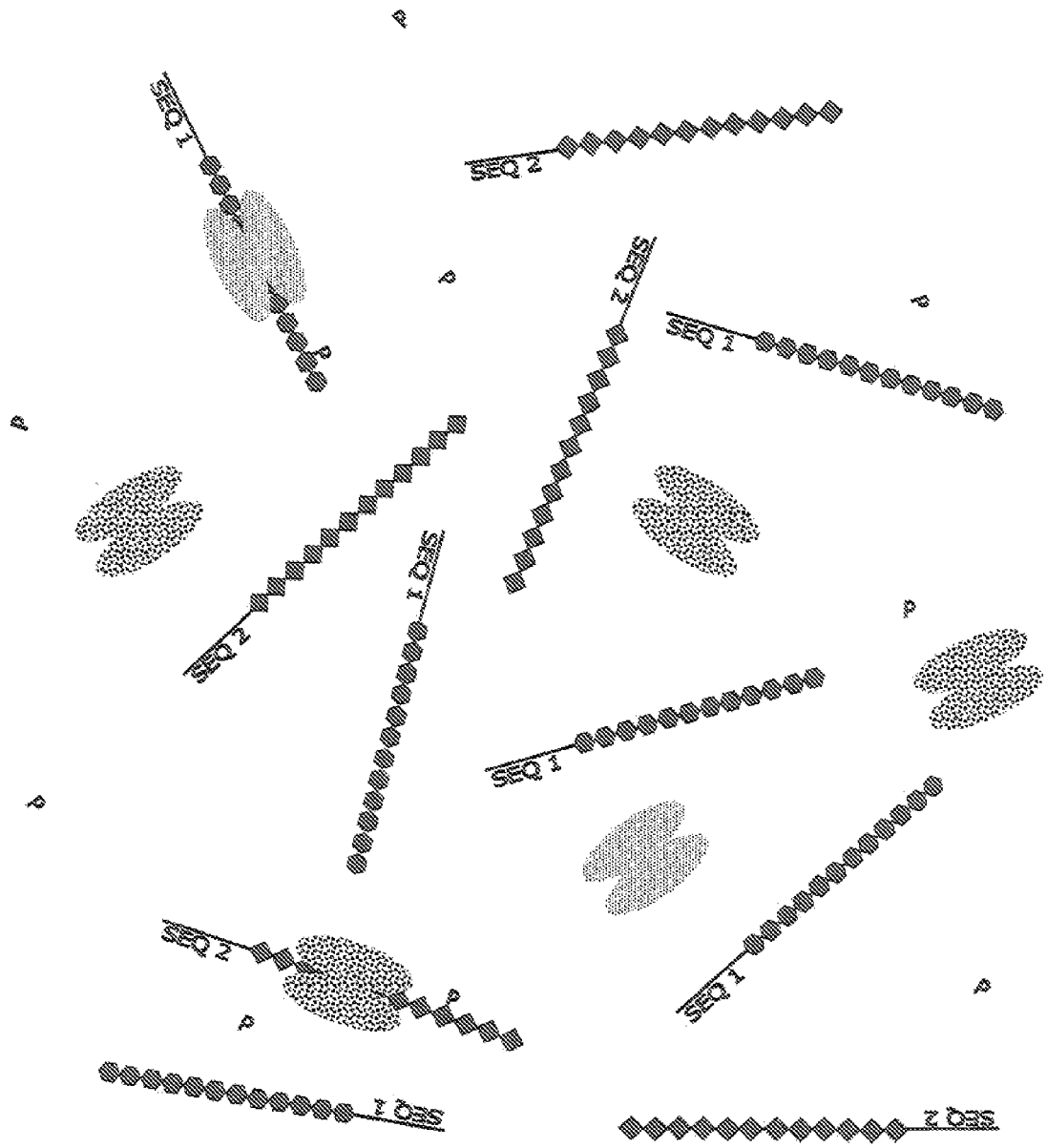
FIG. 6 is a schematic diagram showing a non-limiting embodiment of the disclosure in which two different peptide sequences are incubated in a phosphorylation reaction mixture simultaneously with two different protein kinases, each of which specifically recognizes its phospho-acceptor site on the respective peptides. (shown as differently patterned widened FIG. 8's). Note that the two peptide sequences are covalently attached to two different single stranded nucleic acid sequences, such that each molecule has the identical amino acid and nucleic acid sequence.

As mentioned above, the substrates can be contacted with a phospho-transfer activity prior to being immobilized on a solid phase. For example, instead of being immobilized on encoded particles before contact with the phospho-transfer activity, the substrates shown in FIG. 6 each have a sequence-specific tag on one end, such as a single-stranded oligonucleotide, such that substrates having the same amino acid sequence have the same tag attached to them. Thus, each molecule of each peptide substrate with the same sequence has the same tag sequence coupled to it, and that tag is different for each different peptide substrate (i.e., peptide substrates having different amino acid sequences also have different tags). The substrates, for example, in approximately known numbers, are then added to a biological sample in which the presence of some quantity of the phospho-transfer activity (e.g., a kinase activity) specific to the phosphoacceptor site in the substrates, in a phosphorylation reaction mixture. If a phospho-transfer activity (e.g., kinase activity) specific to the phosphoacceptor site present in the substrates are in the sample, some or all of the sequence-tagged peptides are phosphorylated. Under appropriate incubation conditions, the number of phosphorylated substrates will be approximately proportional to the specific activity of the phospho-transfer activities (e.g., kinase activities) in the sample.

Figure 7:
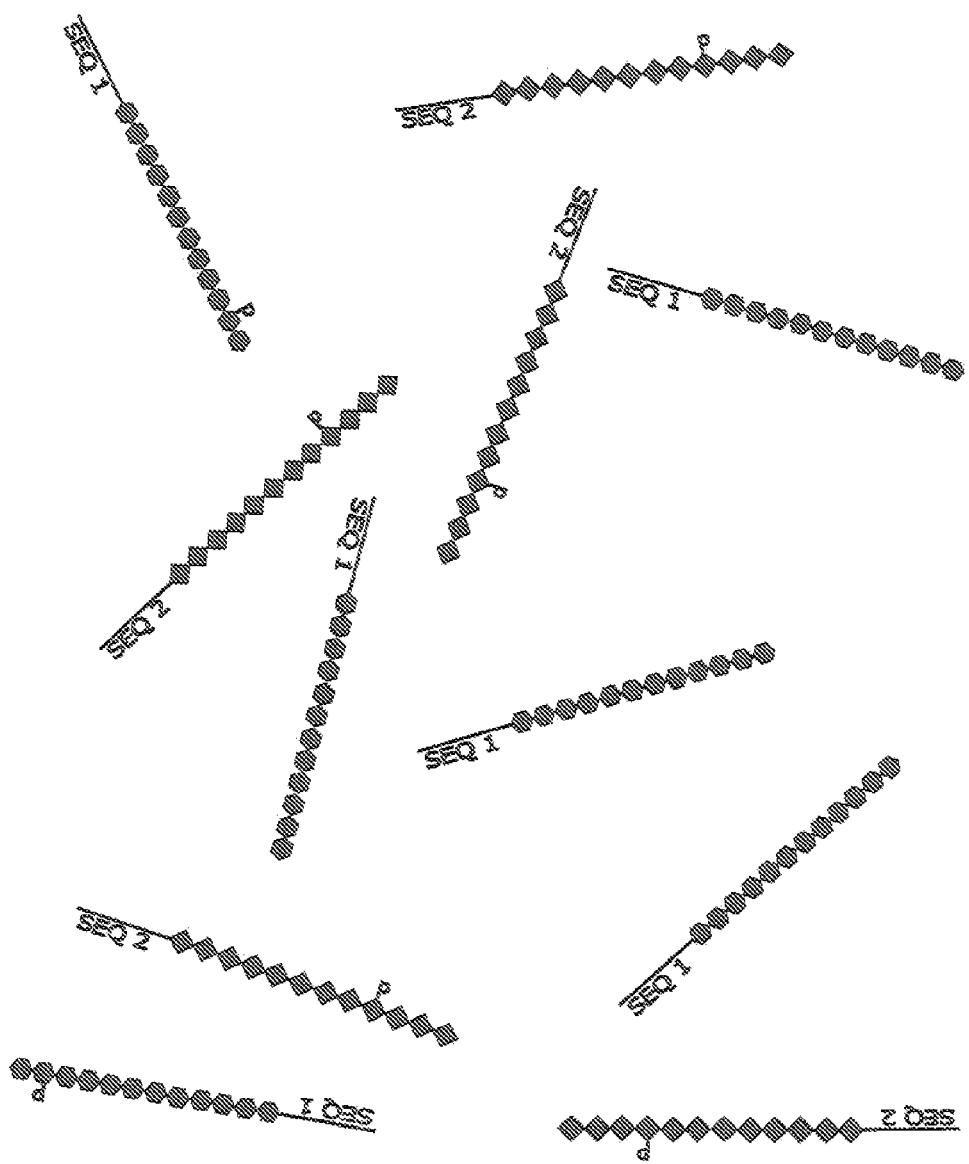
FIG. 7 is a schematic diagram showing the phosphorylation patterns of Peptide 2 (diamonds; attached to nucleic acid sequence 2) and Peptide 1 (hexagons; attached to nucleic acid sequence 1) following incubation with the protein kinases in a phosphorylation reaction mixture.
Figure 8:
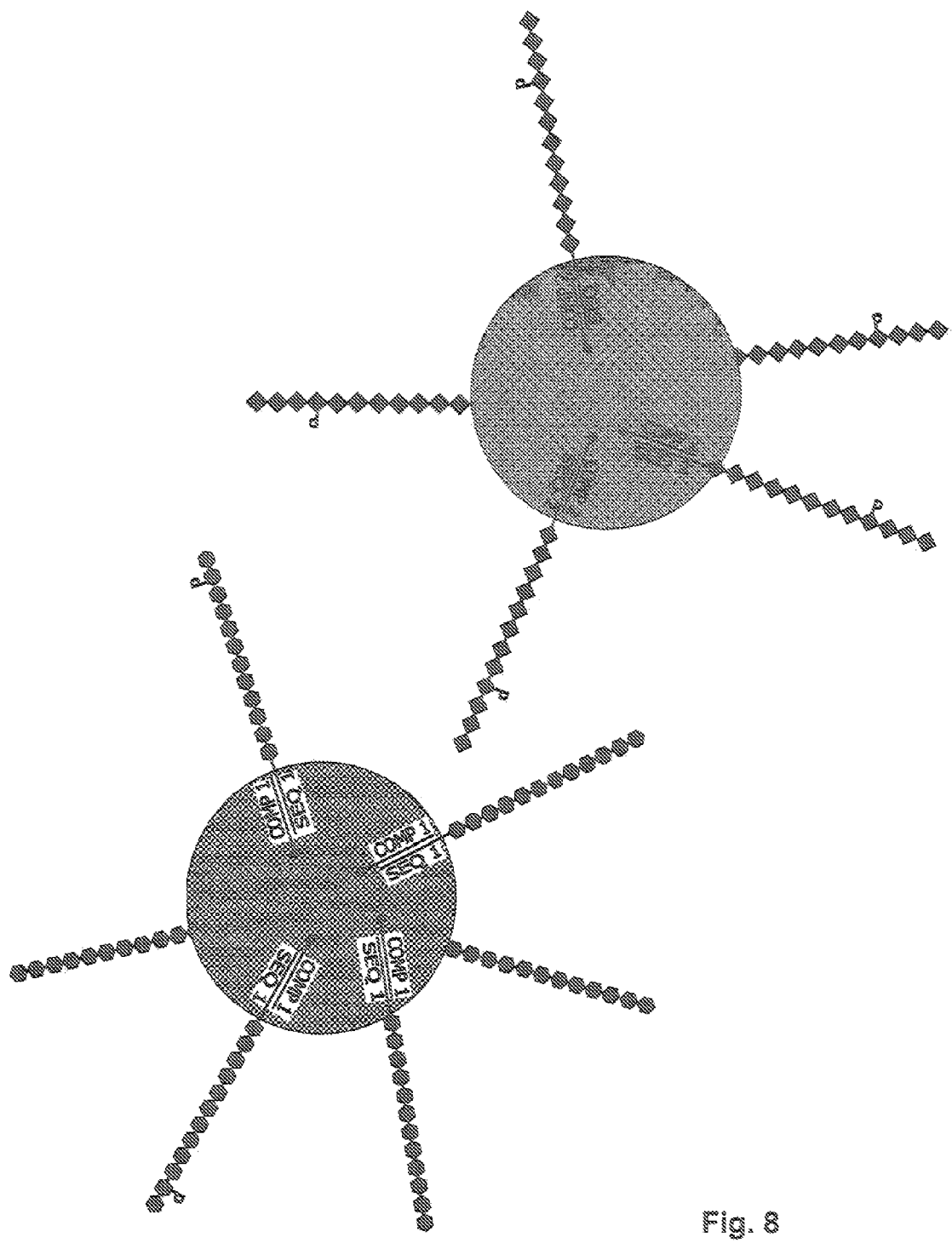
FIG. 8 is a schematic diagram showing the attachment of the peptides of FIG. 7 to one of two beads. Each bead contains multiple sequences that will hybridize to the single stranded nucleic acid sequence on one of the two peptides. Thus, all of the Peptide 1 sequences bind to one bead, while all of the Peptide 2 sequences bind to another bead.
Figure 9:
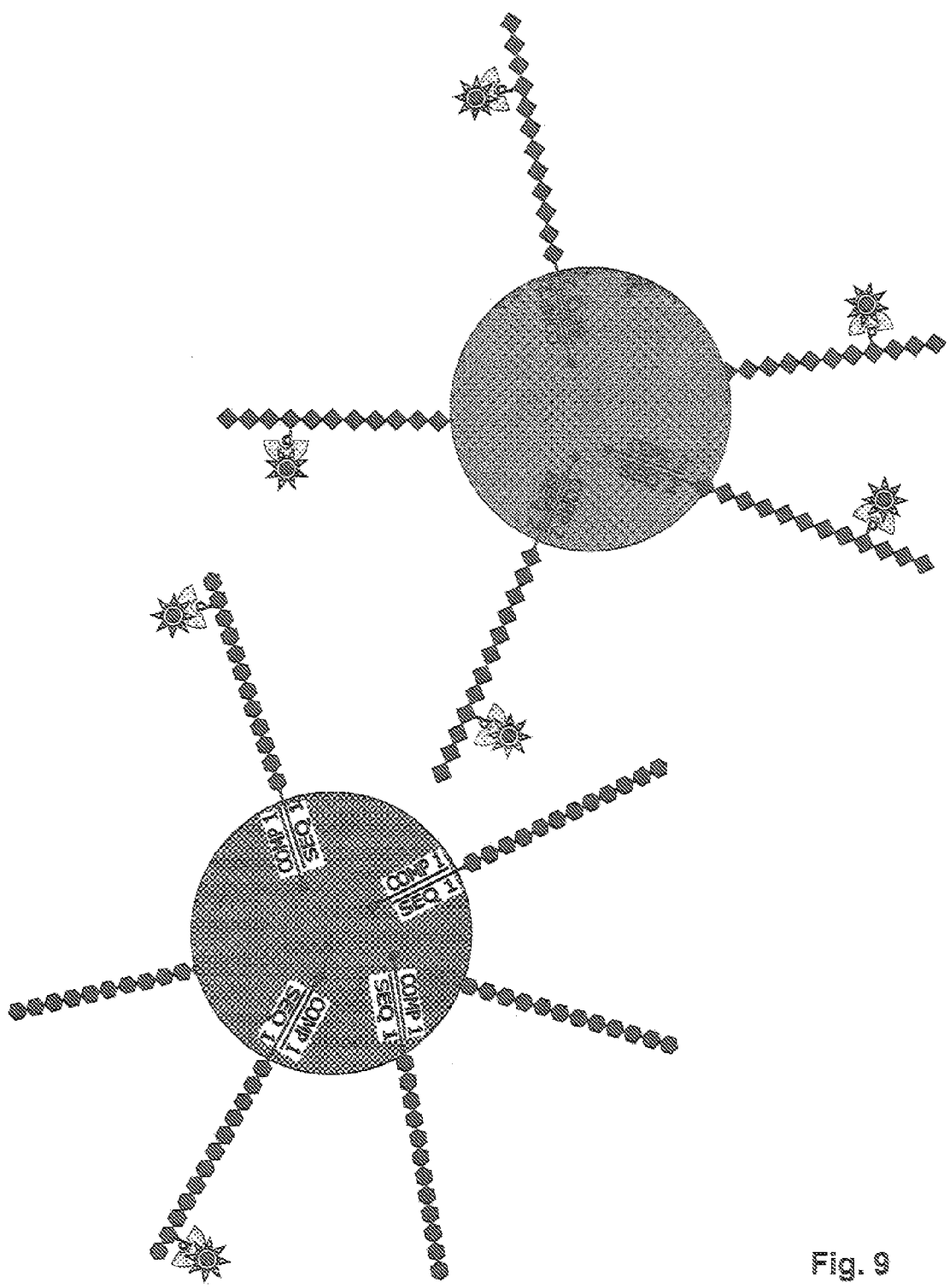
FIG. 9 shows the specific binding of the phosphorylated phosphoacceptor site on the peptides with the detectable phosphomonoester-selective binding agent of the disclosure. The beads, which can be distinguished from each other, can be analyzed to determine how much detectable phosphomonoester-selective binding agent is bound to each, indicating how much each respective peptide substrate is phosphorylated.

After incubation with the kinase-containing sample, the tagged substrates exhibit phosphorylation states in approximate proportion to the specific activity of the respective kinases in the sample (FIG. 7). Next, the tagged peptides are then incubated with a multiplex particle set comprising encoded particles. Each particle encoded with a particular ID has a particular complementary tag sequence immobilized on its surface. As FIG. 8 shows, the tag sequences on the peptides thus specifically hybridize to their complementary tags on the encoded particles. The encoded particles with the specifically hybridized peptides captured are then incubated with the detectable phosphomonoester-selective binding agent, resulting in the binding of the detectable binding agent to the encoded particles if the substrates bound to the particles contained a phosphoacceptor site recognized by a kinase in the sample (FIG. 9). Then the bead set is read on an appropriate instrument that can read the bead ID and quantify the reporter signal for each bead.

Thus, in some aspects, the invention provides a method for detecting the presence of one or more kinase activities in a sample. The method includes contacting the sample suspected of containing one or more kinases with a plurality of peptides in a phosphorylation reaction mixture under phosphorylation conditions, wherein at least one peptide in the plurality comprises a phosphoacceptor site specific to one or more kinase. The plurality of peptides is immobilized on a plurality of solid phases, wherein each peptide having a different amino acid sequence is immobilized on a separate and distinguishable solid phase. Note that by "separate and distinguishable" simply means that each solid phase can be separated and can be distinguished from one another, for example, by using encoded solid phases (e.g., solid phases encoded with different bar codes, different colored solid phases, or solid phases having different sizes). After the immobilized peptides are separated from the phosphorylation reaction mixture, the immobilized peptides are contacted with a detectable phosphomonoester-selective binding agent under conditions whereby the detectable phosphomonoester-selective binding agent will bind to the immobilized peptide if the immobilized peptide is phosphorylated. After the immobilized peptide is separated from the unbound detectable phosphomonoester-selective binding agent, the solid phase to which the detectable phosphomonoester-selective binding agent is bound is detected and distinguished. The binding of the detectable phosphomonoester-selective binding agent to a particular solid phase indicates the presence in the sample of a kinase that recognizes the phosphoacceptor site in the peptide immobilized on that solid phase.

As detailed in Example 3, also featured are methods useful in determining the substrate specificity of a phospho-transfer activity (e.g., a kinase activity or a phosphatase activity). For example, a mixture of encoded particles can be contacted with a sample containing a kinase activity of interest, wherein the mixture of encoded particles includes one or more pluralities of encoded particles, each plurality of particles having a different attached phospho-transfer substrate. Each different substrate is identifiable by a particle code. At least two pluralities of encoded particles include different phospho-transfer substrates, which substrates contain a variant recognition site (phosphoacceptor site) specific to one kinase activity. Methods of designing/generating such recognition site variants are described in the accompanying Examples and also in, e.g., Kim et al. (1999) J. Biol. Chem. 274(53):37538-37543 and Yang and Huang (1994) J. Biol. Chem. 269(47): 29855-29859.

Following the contacting, substrates immobilized on the solid phases are separated from the sample, and then contacted with a detectable phosphomonoester-selective binding agent. In some embodiments, the substrates are contacted with the detectable phosphomonoester-selective binding agent prior to immobilizing the on a solid phase. In some embodiments, the substrates are contacted with the detectable phosphomonoester-selective binding agent at the same time as the sample. The presence of the detectable phosphomonoester-selective binding agent bound to a particular solid phase indicates the presence in the sample of a kinase that recognizes a phosphoacceptor site present in the substrates immobilized on that particular solid phase. Such results would indicate that the preferentially phosphorylated substrate contains a preferred recognition site for that particular kinase activity.

In various embodiments, the detectable phosphomonoester-selective binding agent bound to the solid phase is detected using a flow cytometer. In particular embodiments, the flow cytometer is a Luminex system, such as a Luminex 200™ system.

Any of the methods for detection (or any screening methods described herein) can be performed in any format that allows for rapid preparation, processing, and analysis of multiple reactions. This can be, for example, in multi-well assay plates (e.g., 96 wells or 386 wells). Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting the detectable phosphomonoester-selective binding agent. Examples of such detectors include, but are not limited to, spectrophotometers, luminometers, fluorimeters, and devices that measure radioisotope decay.

Kits

Also provided are kits for detecting the presence of one or more phospho-transfer activities, which kits can include a mixture of encoded particles and a detectable phosphomonoester-selective binding agent. The mixture includes one or more pluralities of encoded particles, each plurality of particles having a different attached phospho-transfer substrate. The phospho-transfer substrate is identifiable by a particle code. At least some of the encoded particles can be magnetic. The kit can optionally contain more than one plurality of encoded particles. For example, the kit can at least two pluralities of encoded particles, which particles contain different nucleic acid particle codes.

The following examples illustrate the preferred modes of making and practicing the present invention, but are not meant to limit the scope of the invention since alternative methods may be utilized to obtain similar results.

EXAMPLES

Example 1

An experiment is performed to determine if amino acid residues outside of the consensus phosphoacceptor site affect a kinase's ability to phosphorylate the phosphoacceptor site. In this example, peptides are generated, where each peptide contains the consensus phosphoacceptor site (namely Nterm-S/TXXE-Cterm, where X is any amino acid) for the casein kinase II (CKII) (see, e.g., Hathaway and Traugh (1979) *J. Biol. Chem.*, 254, 762-768; Grankowski, et al. (1991) *Eur. J. Biochem.*, 198, 25-30; Chester and Marshak (1993) *Anal. Biochem.*, 209, 284-2900. Different groups of peptides are generated, where all the peptides in one group have a different amino acid sequence surrounding the consensus phosphoacceptor site (and/or a different amino acid at the X position within the consensus phosphoacceptor site). For example, Group I has the sequence Nterm-ARRSEDEGPPN-Cterm. Group II has the sequence Nterm-FRASEDEQARHL-Cterm. Group III has the sequence Nterm-L ARSEDECDGT H-Cterm. Group IV has the sequence Nterm-ED-SESEDEEED-Cterm. A Control Group of peptides is generated, where the control group peptides have the sequence Nterm-SSSSSSSSSSSS-Cterm.

The peptides are generated, such that there are 100 peptides in each of Group I, Group II, Group III, Group IV, and the Control Group where all the peptides in each group have the identical sequence.

The peptides in each group are attached to the same type of Carboxylated Luminex bead, according to manufacturer's instructions (Luminex Corp., Austin, Tex.). Luminex beads are internally labeled with different amounts of dye, and thus can be distinguished from one another following analysis with a Luminex system (e.g., a Luminex 100 System).

The beads of all Groups, each coated with a different peptide, are now mixed together (there are equal numbers of beads in each group) and exposed to the casein kinase II (Casein Kinase II commercially available from New England Biolabs, Ipswich, Mass.) in a phosphorylation reaction mixture. The phosphorylation reaction mixture provided by New England Biolabs comprises 20 mM Tris-HCl, 50 mM KCl. 10 mM $MgCl_2$, 200 μM ATP, pH 7.5, and recommends incubation for about two hours at 30° C.

Following incubation for an appropriate time (which may be as short as 30 minutes or longer than 24 hours), the beads are separated from the kinase and from the phosphorylation reaction mixture by centrifugation, and resuspended in saline. The beads are then contacted with a phosphomonoester-selective binding agent covalently linked to a cyanine 5 dye. After the unbound phosphomonoester-selective binding agent is removed by centrifuging the beads away from them, the beads are analyzed using a Luminex 100 System.

The results will show that one group of beads (which is coated with one Group of peptides) is more highly phosphorylated than the other groups. The peptides in this Group are found to contain the amino acid residues outside of the consensus phosphacceptor site which are most conducive in allowing phosphorylation of the serine residue in the consensus phosphacceptor site by casein kinase II. This peptide sequence is likely to be similar to that found in casein kinase II's actual biological target.

The outlined approach is superior to the "one-bead one-peptide" methods known in the art for defining protein kinase substrate specificity, which involve generating a peptide library on polymeric beads, where each bead has only one peptide sequence associated with it, incorporating [$\gamma$-$^{32}$P] ATP into the immobilized peptides using a protein kinase of interest, suspending the beads in 1% agarose, immobilizing the agarose on glass plates and exposing the plates to X-ray film for 20-30 hours for identification of beads containing labeled peptides. The labeled beads are then typically excised from the agarose gel and subjected to automated peptide sequencing for identification of the optimal sequence.

Example 2

Example I is essentially repeated, except that the Luminex beads are magnetic, and following incubation of the peptides with casein Kinase II (plus free ATP), the beads are separated from the phosphorylation reaction mixture by simply exposing the mixture to a magnet, allowing the beads to adhere, and rinsing away the components in the reaction mixture that are not bound to the magnet.

The magnetic beads are then exposed to a detectable phosphomonoester-selective binding agent, where the unbound binding agent is removed by allowing the beads to adhere to a magnet and rinsing. The beads are then analyzed using a Luminex 100 System.

Example 3

Peptides containing the phosphoacceptor site of the $Ca^{2+}$/ Calmodulin-Dependent Protein Kinase II (CaMKII) are generated. Groups of these peptides are created, where each group contains an identical number of peptides, each having the same sequence, where different groups have peptides having different sequences. The groups are:

Group I: Nterm-ATRRRLSWRN-Cterm

Group II: Nterm-PTWRFLSEAG-Cterm

Group III: Nterm-VDYRNLSPKL-Cterm

Control Group: Nterm-SSSSSSSSSSSS-Cterm.

All of the peptides in all of the groups are biotinylated on their N terminus. Biotinylation of a peptide can be accomplished using standard methods. For example, the biotin-PEG-NHS reagent is commercially available from Nektar Pharmaceuticals (San Carlos, Calif.). Mixing a peptide with the biotin-PEG-NHS reagent will allow a reaction to spontaneously occur whereby the NHS (the N-Hydroxysuccinimide ester group) on the biotin-PEG-NHS reagent reacts with the $NH_2$ of the Nterm (i.e., N-terminus) of the peptide. As a result, the biotin label is added to the N-terminus of the peptide.

The biotinylated peptides are next contacted with avidin-coated magnetic beads and allowed to bind to the beads (through the biotin on the peptide binding to the avidin on the bead), such that one group of peptide is bound with one group of beads. The beads used are similar to the LumAvidin beads available from Luminex Corp. (Austin, Tex.). LumAvidin beads are internally labeled with different amounts of dye, and thus can be distinguished from one another (and, the groups of peptides can thus be distinguished) on a Luminex system.

The bound peptides attached to the beads are exposed in a phosphorylation reaction mixture to $Ca^{2+}$/Calmodulin-Dependent Protein Kinase II (CaMKII), the active portion of which is commercially available from New England Biolabs (Ipswich, Mass.). The phosphorylation reaction mixture comprises 50 mM Tris-HCl, 10 mM $MgCl_2$, 2 mM dithiothreitol, 0.1 mM EGTA, pH 7.5, and 200 μM ATP, and incubated at 25° C. for two hours. Following the incubation, the kinase is inactivated by heating the phosphorylation reaction mixture (including the beads and kinase) for twenty minutes at 60° C.

The beads (and the peptides bound to them) are then separated from the rest of the components in the phosphorylation mixture by placing the mixture against a magnet, allowing the beads to adhere to the magnet, and removing the remaining components of the phosphorylation mixture. The beads are then contacted with a phosphomonoester-selective binding agent covalently linked to a FITC (fluorescein isothiocyanate) dye. Following exposure to a magnet to separate the beads away from the unbound FITC-labeled phosphomonoester-selective binding agent, the beads are analyzed using a Luminex 100 System.

The results will show that one group of beads (which is coated with one Group of peptides) is more highly phosphorylated than the other groups. The peptides in this Group are found to contain the amino acid residues outside of the consensus phosphacceptor site which are most conducive in allowing phosphorylation of the serine residue in the consensus phosphoacceptor site by CaMKII. This peptide sequence is likely to be similar to that found in CaMKII's actual biological target.

Example 4

Example I is essentially repeated; however, each peptide in each group is synthesized covalently linked to a specific nucleic acid tag covalently linked that is designed to be complementary to one of the tags present on the FlexMap beads commercially available from Luminex Corp., such that each group has a different nucleic acid tag. The groups are thus designed to have the following sequences:

Group I: Nucleic acid tag 1-Nterm-ARRSEDEGPPN-Cterm

Group II: Nucleic acid tag 2-Nterm-FRASEDEQARHL-Cterm

Group III: Nucleic acid tag 3-Nterm-L ARSEDECDGTH-Cterm

Group IV Nucleic acid tag 4-Nterm-EDSESEDEEDED-Cterm

Control Group: Nucleic acid tag 5-Nterm-SSSSSSSSSSSS-Cterm.

There are 100 peptide/nucleic acid molecules per group. The groups are pooled in incubated with casein kinase II (CKII) in a phosphorylation reaction mixture as described in Example I. Following incubation (and optionally following kinase inactivation by incubating the mixture at 60° C. for 20 minutes), the mixture is added to five different types of Flex-Map beads, where each of the five types of beads is complementary to the nucleic acid tags on the peptides in one of the Groups. After allowing the peptide/nucleic acid molecules to hybridize to the FlexMap beads, the FlexMap beads are next separated by centrifugation from the other components of the phosphorylation reaction mixture. The beads are next contacted with a detectable phosphomonoester-selective binding agent.

After the unbound detectable phosphomonoester-selective binding agent is removed by centrifuging the beads away from them, the beads are analyzed using a Luminex 100 System.

The results will show that one group of beads (which is now coated with one Group of peptides) is more highly phosphorylated than the other groups. If the results of this Example are the same as those seen in Example I, it will indicate that the availability of the phosphoacceptor site in the peptide substrate to the kinase is not compromised by the attachment of the peptide substrate to a solid phase during phosphorylation. If the results are different from those of Example I, it will indicate that the phosphoacceptor site in the peptide substrate is compromised by the attachment of the peptide substrate to the solid phase during phosphorylation. See, e.g., Hutti, J. E. et al., (2004) *Nature Methods* 1(1): 27-29.

Example 5

The sequence Nterm-YLRRRLSDSN-Cterm, is contained in synapsin site 1, the naturally occurring substrate for CaMKII (see, e.g., Pearson, R. B., and Kemp, B. E. (1991). In T. Hunter and B. M. Sefton (Eds.), *Methods in Enzymology* Vol. 200, (pp. 62-81). San Diego: Academic Press). An experiment is performed to determine the best conditions for phosphorylating the serine residue in this sequence.

Peptides having the sequence Nterm-YLRRRLSDSN-Cterm are generated and attached to different groups of magnetic Luminex beads. The groups differ based on the number of peptides attached to the beads. The groups are as follows:

Group I: 10 peptides per bead

Group II: 50 peptides per bead

Group III: 100 peptides per bead

Group IV: 200 peptides per bead.

Group V: 500 peptides per bead.

Group VI: 1000 peptides per bead.

One hundred beads per group are made. The beads are pooled (i.e., 600 beads are pooled) and all groups are incubated at the same time with CaMKII, and, following staining with a FITC-labeled phosphomonoester-selective binding agent of the invention as described in Example III, the beads are analyzed with a Luminex 100 system.

The group of peptides where the level of the fluorescence to peptide ratio is the highest indicates the best conditions for phosphorylation of the peptide by CaMKII.

Example 6

A biological sample is tested to determine if it contains $Ca^{2+}$/Calmodulin-Dependent Protein Kinase II (CaMKII) and/or Casein Kinase II (CKII, CK-2).

Peptides having the sequence Nterm-YLRRRLSDSN-Cterm (which is present in the naturally occurring substrate for CaMKII) are generated and attached to one group of magnetic Carboxylated Luminex beads. Peptides having the sequence Nterm-ADSESEDEED-Cterm (which is present in the naturally occurring substrate for CKII) are generated and attached to a second group of magnetic Carboxylated Luminex beads. Control peptides with the sequence Nterm-SSSSSSSSSS-Cterm are generated and attached to a third group of magnetic Carboxylated Luminex beads.

One hundred beads per group are generated. The beads are pooled (i.e., 300 beads are pooled) and all groups are incubated at the same time with the sample in a phosphorylation reaction mixture that allows the activity of both CaMKII and CKII. After incubating for an appropriate time to allow the kinases (if present) to phosphorylate their substrates, the beads are removed by adherence to a magnet, and contacted with a phycoerythrin-labeled phosphomonoester-selective binding agent. Free (i.e., non-binding) binding agent is removed, again by adhering the beads to a magnetic), and then the beads are analyzed with a Luminex 100 system.

The results of this experiment will allow the simultaneous determination of which, if any, of CaMKII or CKII is present in the sample. If the binding agent binds to the group of beads attached to the Nterm-YLRRRLSDSN-Cterm peptide, then CaMKII is present in the sample. If the binding agent binds to the group of beads attached to the Nterm-ADSESEDEED-Cterm peptide, then CKII is present in the sample.

Example 7

Protein phosphatase type 2A (PP2A) is a protein serine/threonine phosphatase that controls a number of cellular processes, including transcription, translation, metabolism, cell growth, and apoptosis (Janssens and Goris (2001) Biochem. J. 353: 417-439; Zabrocki et al. (2002) Mol. Microbiol. 43: 835-842; Milward et al. (1999) Trends Biochem. Sci. 24:186-191). The sequence Nterm-RRA(pT)VA-Cterm (where the indicated threonine residues is phosphorylated), is the consensus phosphatase recognition site for several serine/threonine phosphatases, including protein phosphatases 2A. An experiment is performed to determine the best conditions required for protein phosphatase type 2A to remove the phosphate group from the threonine residue in the Nterm-RRA (pT)VA-Cterm consensus phosphatase recognition sequence.

Different groups of peptides are generated, where all the peptides in one group have a different amino acid sequence surrounding the consensus phosphatase recognition site. The groups have the following sequences (where the pT symbol denotes a phosphorylated threonine residue):

Group I: Nterm-QRRRA(pT)VAWN-Cterm.

Group II: Nterm-TRRRA(pT)VAHS-Cterm.

Group III: Nterm-LYRRA(pT)VARH-Cterm.

Group IV: Nterm-EK RRA(pT)VAT N-Cterm.

Control Group; Nterm-SSSSSpTSSSS-Cterm.

The peptides are generated, such that there are 100 peptides in each of Group I, Group II, Group III, Group IV, and the Control Group where all the peptides in each group have the identical sequence. The peptides in each group are attached to the same type of Carboxylated Luminex bead, according to manufacturer's instructions (Luminex Corp., Austin, Tex.). Luminex beads are internally labeled with different amounts of dye, and thus can be distinguished from one another following analysis with a Luminex system (e.g., a Luminex 100 System).

Purified Protein Phosphatase 2A (PP2A) is purchased from Promega Corp. (Madison Wis.). The beads of all Groups (there are equal numbers of beads in each of the groups), each coated with a different peptide, are now mixed together and exposed to the PP2A in a phosphatase reaction mixture containing 50 mM Tris-HCl (pH 8.5), 20 mM MgCl2, and 1 mM DTT.

Following incubation at 30° C. for an appropriate time (which may be as short as 20 minutes or longer than 24 hours), the beads are separated from the PP2A and from the phosphatase reaction mixture by centrifugation, and resuspended in saline. The beads are then contacted with a phosphomonoester-selective binding agent covalently linked to a cyanine 5 dye. After the unbound phosphomonoester-selective binding agent is removed by centrifuging the beads away from them, the beads are analyzed using a Luminex 100 System.

The results will show that one group of beads (which is coated with one Group of peptides) is less phosphorylated than the other groups. The peptides in this Group are found to contain the amino acid residues outside of the consensus phosphatase recognition site which are most conducive in allowing dephosphorylation of the threonine residue in the consensus phosphatase recognition site by casein kinase II. This peptide sequence is likely to be similar to that found in PP2A's actual biological target.

Example 8

The phosphomonoester-selective binding agent can also be used to detect the presence of a phosphodiesterase. As mentioned above, a phosphodiesterase can cleave a cAMP into AMP. AMP, unlike cAMP, has a free phosphomonoester, which can be specifically bound by a phosphomonoester-selective binding agent of the invention.

Accordingly, different amounts of 3'5' cyclic AMP (cAMP) are coupled to different groups of Luminex beads according to standard methods. Different groups of beads are coupled to cAMP as follows:

Group I: 10 molecules of cAMP per bead

Group II: 50 molecules of cAMP per bead

Group III: 100 molecules of cAMP per bead

Group IV: 200 molecules of cAMP per bead.

Group V: 500 molecules of cAMP per bead.

Group VI: 1000 molecules of cAMP per bead.

There are equal numbers of beads in each group. All groups of beads are pooled and incubated with purified Phosphodiesterase I (from Crotalus adamanteus venom; commercially available from, e.g., GE Healthcare (Piscataway, N.J.) in a phosphodiesterase reaction mixture (e.g. 100 mM Tris-HCl (pH 8.9), 100 mM NaCl and 14 mM MgCl$_2$,) and at 25° C. for about two hours. Following incubation for an appropriate time (which may be as short as 20 minutes or longer than 24 hours), the beads are separated from the phosphodiesterase I and from the phosphatase reaction mixture by centrifugation, and resuspended in saline. The beads are then contacted with a phosphomonoester-selective binding agent covalently linked to a cyanine 5 dye. After the unbound phosphomonoester-selective binding agent is removed by centrifuging the beads away from them, the beads are analyzed using a Luminex 100 System.

The results will show that one group of beads (which is coated with one amount of cAMP) is more heavily labeled with cyanine 5 than the other groups (i.e., this group has the most cAMP converted to AMP, which can bind the phosphomonoester-selective binding agent). This concentration of cAMP is most conducive for allowing activity of Phosphodiesterase I.

Example 9

Figure 11:
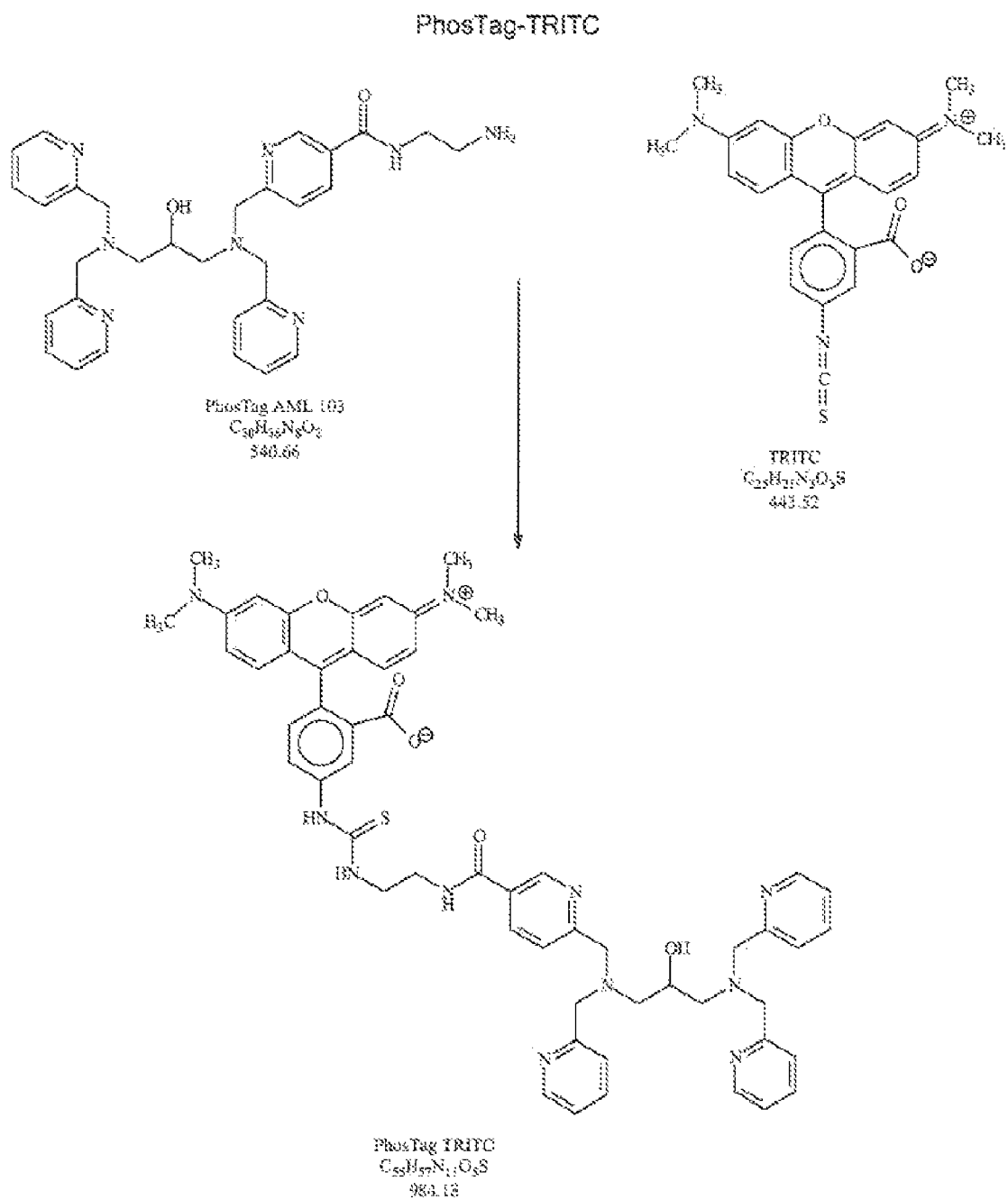
FIG. 11 is schematic diagram depicting the synthesis of a TRITC labeled phosphomonoester-selective binding agent.

A TRITC labeled phosphomonoester-binding molecule was synthesized as depicted in FIG. 11. For this synthesis, 34 mg (0.063 mmol) of N,N,N'-Tri(2-pyridylmethyl)-N'-[5-N"-

(2-aminoethyl)carbamoyl-2-pyridylmethyl]-1,3-diamino-propane-2-ol (34 mg, 0.063 mmol) was dissolved in 5 mL of dimethylformamide. To this solution was added 20 mg (0.045 mmol) tetratmethylrhodamine-5(6)-isothiocyanate (0.045 mmol, 20 mg). The resulting solution containing the reaction mixture was sonicated at room temperature for 20 minutes.

The reaction mixture was purified on a C18(2) preparative column using the following conditions:

| Column: | Phenomenex Luna 250 × 21 mm |
|---|---|
| Solvent A: | 1% TEAAc pH 4.2 |
| Solvent B: | Acetonitrile |
| Gradient: | 100% A → 80% B over 75 min |
| Flow Rate: | 10 mL/min |
| UV: | 254, 540 nm |

Fractions were collected between 45-50 minutes by following the UV absorption at 540 nm. The fractions were concentrated and analyzed by Mass Spectrometry.

Example 10

Figure 12:
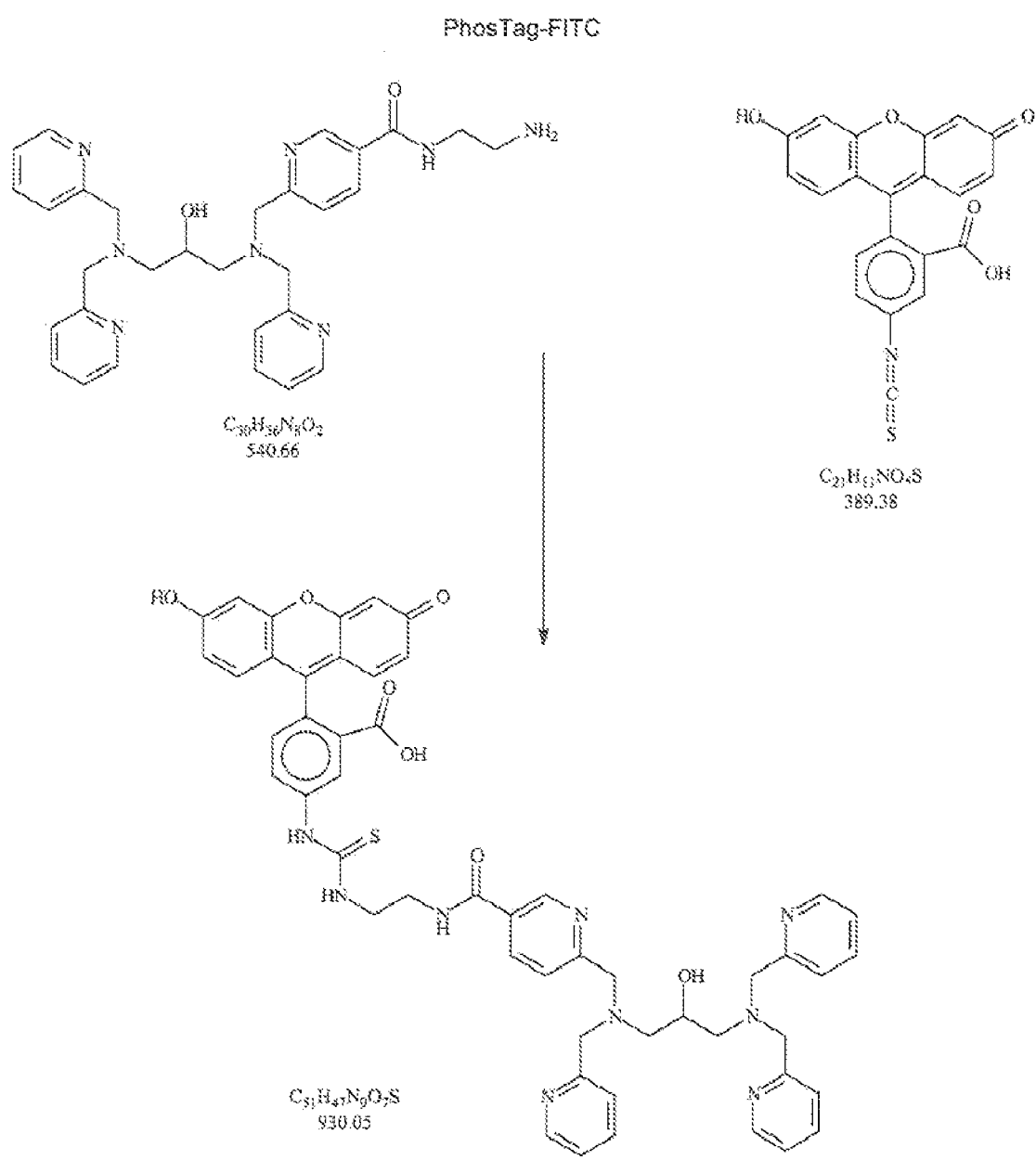
FIG. 12 is a schematic diagram depicting the synthesis of a FITC labeled phosphomonoester-selective binding agent.

A FITC labeled phosphomonoester-binding molecule was synthesized as depicted in FIG. 12. For this synthesis, 10 mg (0.018 mmol) of N,N,N'-Tri(2-pyridylmethyl)-N'-[5-N'''-(2-aminoethyl)carbamoyl-2-pyridylmethyl]-1,3-diaminopropane-2-ol was dissolved in 1 mL of methanol. 15 mg (0.038 mmol) fluorescein isothiocyanate (0.038 mmol, 15 mg) was dissolved in 0.5 mL dimethylformamide, and added to the solution containing the 10 mg (0.018 mmol) of N,N,N'-Tri(2-pyridylmethyl)-N'-[5-N'''-(2-aminoethyl)carbamoyl-2-pyridylmethyl]-1,3-diaminopropane-2-ol. The final solution containing the reaction mixture was next sonicated at room temperature for 20 minutes.

Following sonication, the reaction mixture was purified on a C18(2) preparative column using the following conditions:

| Column: | Phenomenex Luna 250 × 21 mm |
|---|---|
| Solvent A: | 1% TEAAc pH 4.2 |
| Solvent B: | Acetonitrile |
| Gradient: | 100% A → 5 min |
| | 100% A → 100% B over 50 min |
| Flow Rate: | 10 mL/min |
| UV: | 254, 490 nm |

Fractions were collected between 29-38 minutes by following the UV absorption at 490 nm. The fractions were concentrated and analyzed by Mass Spectrometry.

Example 11

Figure 13:
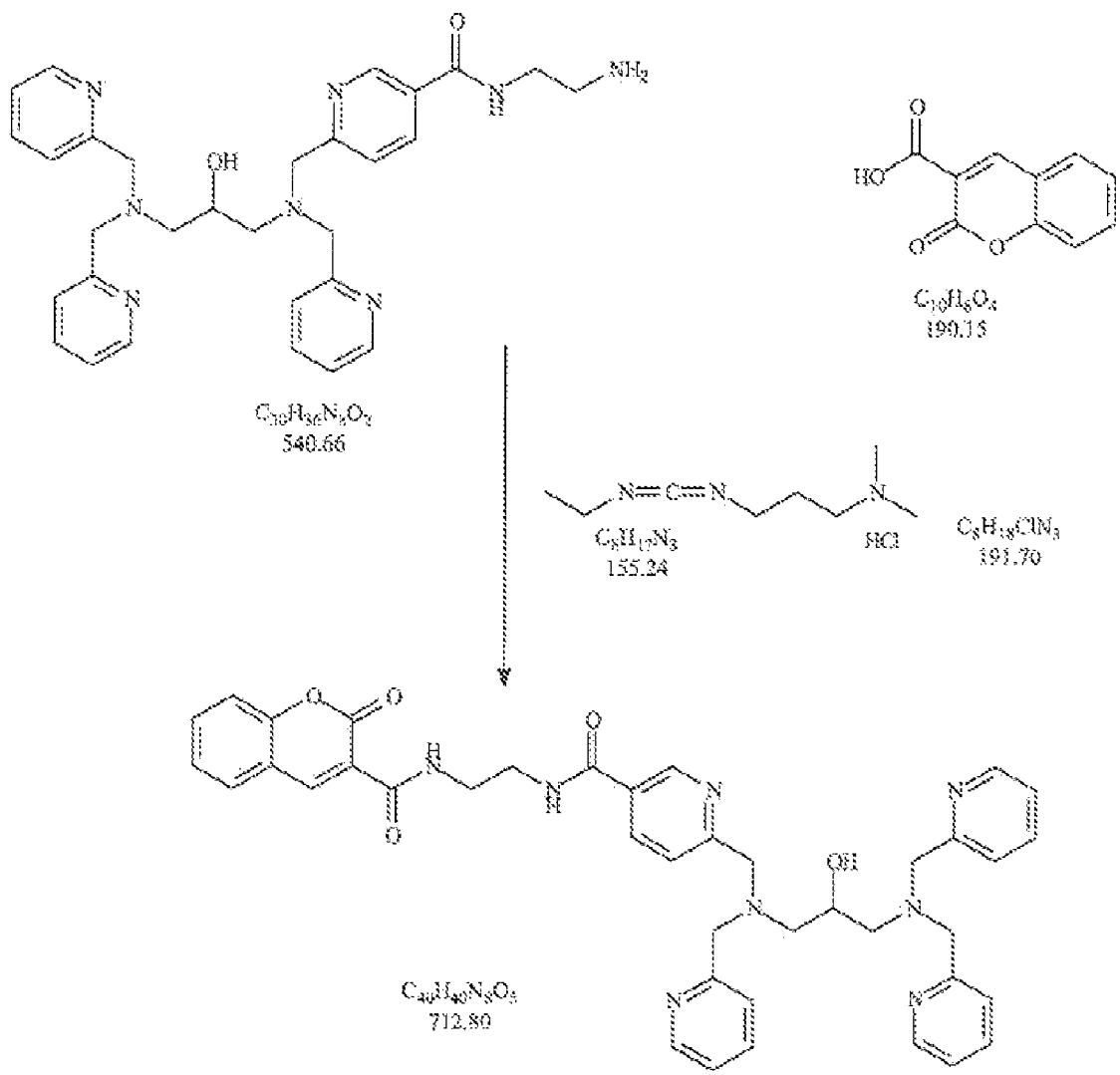
FIG. 13 is a schematic diagram depicting the synthesis of a coumarin labeled phosphomonoester-selective binding agent.

A coumarin labeled phosphomonoester-binding molecule was synthesized as depicted in FIG. 13. For this synthesis, 10 mg (0.018 mmol) of N,N,N'-Tri(2-pyridylmethyl)-N'-[5-N'''-(2-aminoethyl)carbamoyl-2-pyridylmethyl]-1,3-diaminopropane-2-ol and 16 mg (0.084 mmol) Coumarin-3-carboxylic acid (CAS#531-81-7) were dissolved in 5 mL of methanol. To this solution was added 0.1 mL of dimethylformamide and 45 mg (0.235 mmol) of 1-(3-(dimethylamino)propyl)-3-ethyl-carbodiimide hydrochloride (CAS#25952-53-8). The resulting mixture was stirred at room temperature for 4 hours.

The reaction mixture was purified on a C18(2) preparative column using the following conditions:

| Column: | Phenomenex Luna 250 × 21 mm |
|---|---|
| Solvent A: | 1% TEAAc pH 4.2 |
| Solvent B: | Acetonitrile |
| Gradient: | 100% A → 5 min |
| | 100% A → 100% B over 50 min |
| Flow Rate: | 10 mL/min |
| UV: | 300 nm |

Fractions were collected between 24-40 minutes by following the UV absorption at 300 nm. The fractions were concentrated and analyzed by Mass spectrometry.

Example 12

Figure 14:
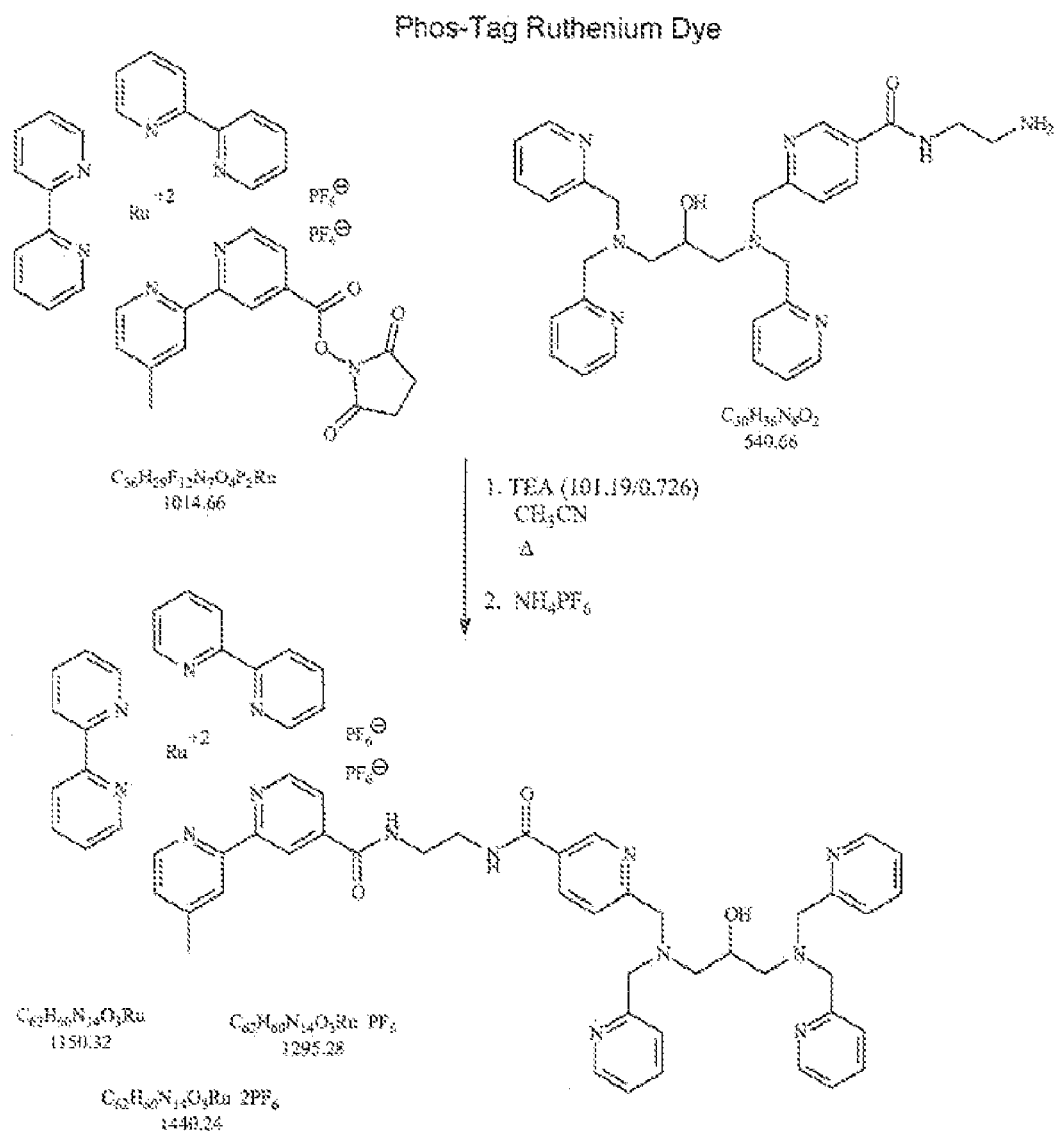
FIG. 14 is a schematic diagram depicting the synthesis of a ruthenium dye labeled phosphomonoester-selective binding agent.

A Ruthenium Dye labeled labeled phosphomonoester-binding molecule was synthesized as depicted in FIG. 14. For this synthesis, the following reagents were used:
N,N,N'-Tri(2-pyridylmethyl)-N'-[5-N'''-(2-aminoethyl)carbamoyl-2-pyridylmethyl]-1,3-diaminopropane-2-ol (Phostag AML 103)
Bis(2,2'-bipyridine)-4'-methyl-4-carboxybipyridine-ruthenium N-succinimidyl ester-bis(hexafluorophosphate) (MW—1014.66)—Fluka 96631
PhosTag AML 103 (MW 540.66)—Supplied by NARD
Ammonium Hexafluorophosphate ($NH_4PF_6$) (MW 163)—Aldrich 216593
Triethylamine (MW 101.19; Dens. 0.726)—Aldrich 471283
CM-Sephadex C-50 dry resin—Pharmacia 17-0220-01

For this synthesis, 10 mg (0.018 mmol) of N,N,N'-Tri(2-pyridylmethyl)-N'-[5-N'''-(2-aminoethyl)carbamoyl-2-pyridylmethyl]-1,3-diaminopropane-2-ol, 10 mg (0.010 mmol) of bis(2,2'-bipyridine)-4'-methyl-4-carboxybipyridine-ruthenium N-succinimidyl ester-bis(hexafluorophosphate), 10 μL (7.26 mg; 0.071 mmol) of triethylamine, and 4 mL of acetonitrile were combined in a 25 mL round bottom flask. The resulting orange-red solution was stirred at 40° C. for 2 hours. The solvents were removed under reduced pressure to leave a deep orange residue.

The reaction mixture was purified by ion exchange chromatography (CM-Sephadex C-50). Briefly, 0.8 g of resin was allowed to swell overnight in 40 mL of 0.6 mM phosphate buffer, pH 7.2. The resin was added to a 60 mL column and was allowed to settle for 1 hour. The column was then rinsed with approximately 200 mL of phosphate buffer. 3 mL of phosphate buffer was added to the product and methanol was added until the residue dissolved. The reaction mixture was added to the column and eluted with a 0.6 mM phosphate buffer→100 mM NaCl gradient. A yellowish band eluted at approximately 5-10 mM NaCl.

The Ruthenium Dye labeled labeled phosphomonoester-binding molecule (main red band) eluted with 40 mM NaCl. The product was collected and the solvents were reduced to about 20 mL under reduced pressure. To this red solution was added 12 mg (0.074 mmol) of Ammonium Hexafluorophosphate. The mixture was stirred for 10 minutes, and then extracted with methylene chloride (2×10 mL). The combined organic layers were washed with a 10 mM $NH_4PF_6$ solution (2×20 mL). The organic layer was dried over magnesium sulfate, filtered and concentrated to produce an orange-red solid.

Example 13

An experiment was performed to determine the sensitivity of the directly phosphomonoester-selective binding agents described above. Accordingly, 9 known proteins, namely myosin, β-galactosidase, phosphorylase b, bovine serum albumin, ovalbumin, carbonic anhydrase, trypsin inhibitor, lysozyme, and aprotinin, were loaded into three lanes of a polyacrylamide gel and resolved by electrophoresis using 12% SDS-polyacrylamide gels, according to standard methods (see, e.g., Ausubel et al., *Current Protocols in Molecular Biology*, John Wiley & Sons, Inc., New York, N.Y. 1987, including period updates through 2006). Only one of these proteins, namely ovalbumin, is phosphorylated. Three lanes of proteins were run on the gel, and then the gel cut apart and each lane stained separately.

The first lane of the gel was stained with the total protein stain, SYPRO® Ruby dye (commercially available from Molecular Probes Inc.). The second lane of the gel was stained with the TRITC labeled phosphomonoester-selective binding agent. The third lane of the gel was stained with the Ru-Dye labeled phosphomonoester-selective binding agent.

The staining protocol using the TRITC labeled phosphomonoester-selective binding agent was as follows. After electrophoresis, gels are fixed for one hour in 10% ethanol/7% acetic acid with gentle agitation. Typically the gels are placed in a volume of fixative that is equivalent to about ten times the volume of the gel. This step is repeated using fresh fixative for an additional 30 minutes to ensure complete removal of SDS. The gel is then washed three times for 10 minutes each in deionized water to remove the ethanol and acetic acid. The lyophilized TRITC labeled phosphomonoester-selective binding agent from Example 9 (0.1 μmol per vial) is diluted in 100 μl dimethyl formamide. Then 10 μl of 20 mM $ZnCl_2$ is added, followed by 0.89 mL 10 mM Bis-Tris/0.1 M Na2SO4, pH 6.5, to generate 1 ml of dye concentrate. Typically this dye concentrate is incubated for 30 minutes at room temperature to ensure binding of the zinc ions to the chelate. The staining solution is prepared by adding 250 μl concentrate to 25 mL of 10 mM Bis-Tris, 100 mM $Na_2SO_4$, 15% propylene glycol, pH 6.5 (0.025 μmol dye per gel). The gel is incubated in the staining solution with gentle agitation for 90 minutes without direct exposure to light. Then, the gel is destained three times for 30 minutes each in 25 ml 10 mM Bis-Tris, 100 mM $Na_2SO_4$, 15% propylene glycol, pH 6.5. Afterwards, the gel is washed twice for 5 minutes each with deionized water. The gel is imaged using a xenon-arc lamp-based CCD camera system (ProXPRESS 2D imager, PerkinElmer) with band pass filters optimized to allow excitation illumination at 541 nm and emission readings at:572 nm.

The staining protocol using the Ru-Dye labeled phosphomonoester-selective binding agent was as follows. After electrophoresis, gels are fixed for one hour in 10% ethanol/7% acetic acid with gentle agitation. Typically the gels are placed in a volume of fixative that is equivalent to about ten times the volume of the gel. This step is repeated using fresh fixative for an additional 30 minutes to ensure complete removal of SDS. The gel is then washed three times for 10 minutes each in deionized water to remove the ethanol and acetic acid. The lyophilized Ru-Dye labeled phosphomonoester-selective binding agent from Example 12 (0.15 μmol per vial) is diluted in 150 μl dimethyl formamide. Then 15 μl of 20 mM $ZnCl_2$ is added, followed by 1.334 mL 10 mM Tris-HCl/0.1 M $Na_2SO_4$, pH 8.0 to generate 1.5 ml of dye concentrate. Typically this dye concentrate is incubated for 30 minutes at room temperature to ensure binding of the zinc ions to the chelate. The staining solution is prepared by adding 750 μl concentrate to 25 mL of 10 mM Tris-HCl, 100 mM $Na_2SO_4$, 15% propylene glycol, pH 8.0 (0.075 μmol dye per gel). The gel is incubated in the staining solution with gentle agitation for 90 minutes without direct exposure to light. Then, the gel is destained three times for 30 minutes each in 25 ml 10 mM Bis-Tris, 100 mM $Na_2SO_4$, 15% propylene glycol, pH 6.5. Afterwards, the gel is washed twice for 5 minutes each with deionized water. The gel is imaged using a xenon-arc lamp-based CCD camera system (ProXPRESS™ 2D imager, PerkinElmer) with band pass filters optimized to allow excitation illumination at 456 nm and emission readings at 654 nm.

Figure 10:
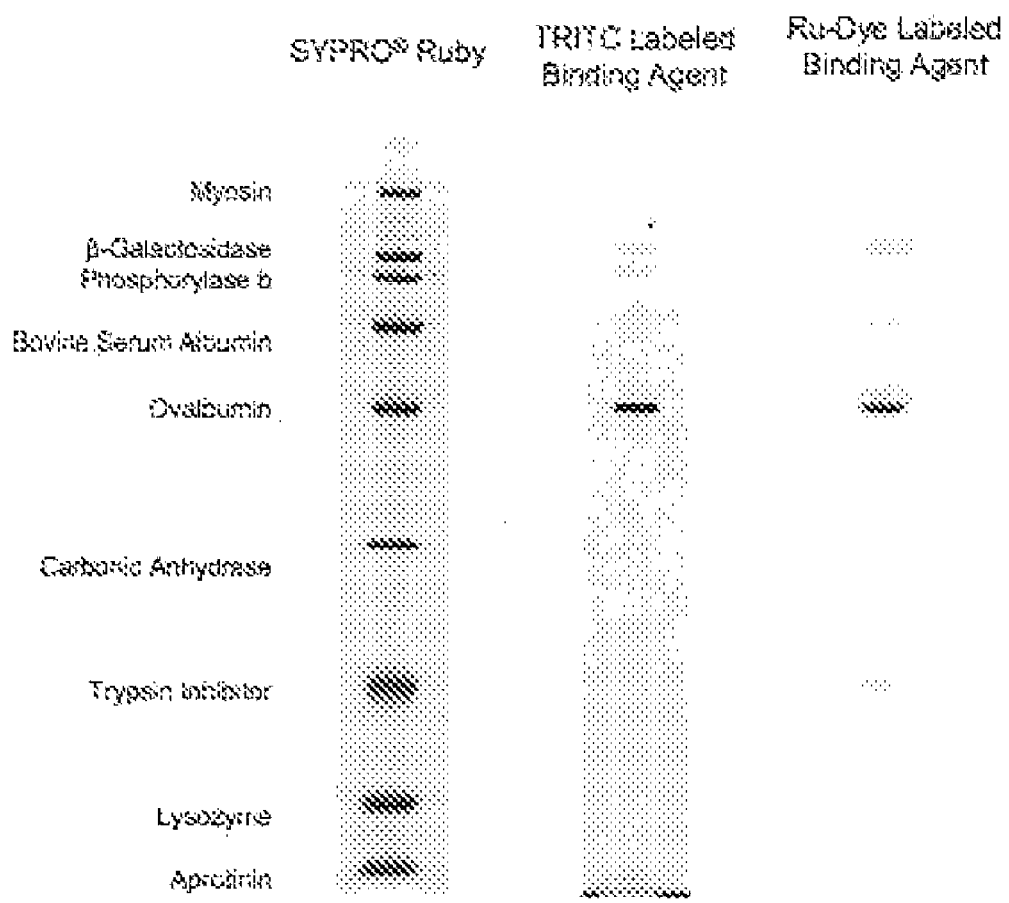
FIG. 10 is a series of photographs of transferred protein gels, wherein phosphoproteins are detected using counter anion-dinuclear transition metal cation-pair complexes.

As shown in FIG. 10 (left column), SYPRO® Ruby dye clearly stained all of the proteins in the gel. In contrast, the TRITC labeled phosphomonoester-selective binding agent and the Ru-Dye labeled phosphomonoester-selective binding agent stained only ovalbumin (FIG. 10, middle and right lanes respectively). Not surprisingly, the only protein to be stained by the TRITC labeled phosphomonoester-selective binding agent and the RU-Dye labeled phosphomonoester-selective binding agent was the phosphorylated ovalbumin protein.

FIG. 10 shows detection of phosphoproteins using counter anion-dinuclear transition metal cation-pair complexes. (a.) SYPRO® Ruby dye staining of broad-range molecular weight marker proteins in an SDS-polyacrylamide gel. (b.) Selective staining of the phosphoprotein ovalbumin using TRITC conjugated to a phosphomonoester-selective binding agent, as synthesized in Example 9 (c.) Selective staining of the phosphoprotein ovalbumin using a ruthenium complex conjugated to a phosphomonoester-selective binding agent as synthesized in Example 12. The counter-anion employed was sulfate, as explained in Example 13.

Thus, the labeled phosphomonoester-selective binding agent described above are able to specifically bind gel-immobilized phosphorylated proteins.

Example 14

In another example, the same proteins in Example 13 (i.e., myosin, β-galactosidase, phosphorylase b, bovine serum albumin, ovalbumin, carbonic anhydrase, trypsin inhibitor, lysozyme, and aprotinin) are loaded into six lanes of a gel and are resolved by SDS-polyacrylamide gel electrophoresis. The proteins are next transferred to a polyvinylidene difluoride (PVDF) membrane. Following transfer, the PVDF membrane is cut up between the lanes, and phosphoprotein blotting analysis is performed using, as reporter, TRITC labeled phosphomonoester-selective binding agent. As a positive control, the fifth lane is subjected to Western blotting analysis with an anti-ovalbumin antibody. As a negative control, the sixth and final lane is subjected to Western blotting analysis with an anti-bovine serum albumin antibody. Secondary, TRITC-labeled antibodies are used in the Western blots of the control lanes. The staining protocol using the TRITC labeled phosphomonoester-selective binding agent was as follows. After Western blotting, the blots are allowed to air dry completely, and are then pre-wetted with 100% ethanol. The membranes are washed once in deionized water and then are incubated for one hour in 10% ethanol/7% acetic acid with gentle agitation. Typically the gels are placed in a volume of fixative that is equivalent to about five to ten times the volume of the original gel used for Western blotting. The membrane is agitated in 25 mL of blocking solution (0.5% Tween-20/0.25% poly(vinylpyrrolidone)-40 (PVP-40) in 10 mM Bis-Tris, pH 6.5) for 30 minutes or over night. The membrane is then washed once with 25 mL 10 mM Bis-Tris, 100 mM $Na_2SO_4$, pH 6.5. The TRITC Blot staining buffer is made as follows. Sample lyophilized at 0.1 umol per vial per Example 9 is diluted in 100 μl dimethyl formamide. To this is added 10 μl of 20 mM $ZnCl_2$ and then 0.89 ml of 10 mM Bis-Tris/0.1 M $Na_2SO_4$, pH 6.5 for a total volume of 1 ml of dye concentrate. This is incubated for 30 minutes at room temperature. The TRITC Blot Staining Solution is then prepared by adding 250 μl dye concentrate to 25 ml of 10 mM Bis-Tris, 100 mM $Na_2SO_4$, pH 6.5 (0.025 umol dye per gel). The membrane is placed face down in 25 mL TRITC Blot Staining Solution (prepared in the last step) and incubated with gentle agitation for 30 minutes. The membrane is washed three times for five minutes each in a destain buffer of 10 mM Bis-Tris, 100 mM $Na_2SO_4$, 15% propylene glycol, pH 6.5.

The blots are imaged using a xenon-arc lamp-based CCD camera system (ProXPRESS 2D imager, PerkinElmer) with band pass filters optimized to allow excitation illumination at 541 nm and emission readings at:572 nm.

Review of all of the lanes will reveal that the only the ovalbumin band is stained in the lanes blotted with the TRITC labeled phosphomonoester-selective binding agent, and the anti-ovalbumin antibody. In contrast, only the bovine serum albumin band (and not the ovalbumin band) is stained in the lane blotted with the anti-bovine serum albumin antibody. Thus, the labeled phosphomonoester-selective binding agent described above are able to specifically bind PVDF-immobilized phosphorylated proteins.

Example 15

In another example, a standard set of proteins, as in Example 13 (i.e., myosin, β-galactosidase, phosphorylase b, bovine serum albumin, ovalbumin, carbonic anhydrase, trypsin inhibitor, lysozyme, and aprotinin) was separated by electrophoresis on a 12% SDS polyacrylamide gel. One of the proteins in the set of molecular weight markers was ovalbumin, a known phosphorylated protein. Each lane was loaded with approximately 1 μg of each standard protein. After separation, the gel was fixed in a solution of 10% ethanol and 7% acetic acid. The gel was then washed in distilled water to remove the fixing solution. The phosphoprotein was detected using the TRITC labeled phosphomonoester-selective binding agent as described in Example 13.

The ovalbumin bands were cut out of the gel. Two gel slices were placed in each tube in order to digest 2 μg ovalbumin per tube. The gel slices were incubated in 200 μL of 25 mM ammonium bicarbonate with 5% acetonitrile ambient temperature for 30 minutes. After aspirating the supernatant, the gel slices were incubated with 200 μL of 25 mM ammonium bicarbonate with 50% acetonitrile at ambient temperature for 30 minutes. This step is repeated and then the gel slices were washed twice with 100% acetonitrile. The supernatant was removed and the gel slices were dried at 60° C. for 10 minutes. Trypsin was solubilized in 1 mM HCl and diluted in 25 mM ammonium bicarbonate. Trypsin solution (0.5 μg trypsin per tube) was added to each sample and incubated at 37° C. overnight.

The phosphorylated peptides in the digest were isolated and enriched using $TiO_2$ thin-film coated magnetic beads (Per: Patton, W., Mikulskis, A., Golenko, E. (Jul. 6, 2005) Methods and compositions for detecting and isolating phosphorylated molecules using hydrated metal oxides. US Application Serial No. PCT/US 05/23810.). A suspension of $TiO_2$ coated magnetic beads in 70% ethanol was diluted 1:10 in water and dispensed into a low binding polypropylene 96-well plate. The beads are washed twice with 200 μL of 1% formic acid and 50% acetonitrile. Each trypsin digested sample was mixed with 50 μL of 1% formic acid and 50% acetonitrile. The supernatant containing the digested protein is added to the $TiO_2$ coated magnetic beads and incubated at ambient temperature for 30 minutes with agitation. The supernatant is aspirated from each tube and the beads are washed four times with 1% formic acid and 50% acetonitrile. This is followed by a wash of 50% acetonitrile. The beads are then incubated for 5 minutes in 20 μL of 5 mM ammonium phosphate (pH 9.5) with 75% acetonitrile. The supernatant containing the phosphorylated peptides is aspirated and placed in a clean well. The plate is incubated at 50° C. for 30 minutes to completely dry the sample.

The dried sample is then prepared for mass spectroscopy analysis. The matrix solution is prepared by dissolving 5 mgs of α-cyano-4-hydroxycinnamic acid (CHCA) in 1.25 mL of 1% formic acid and 50% acetonitrile. The dried peptides are completely dissolved in 8 μL of matrix solution. This mixture is then spotted on a sample plate suitable for matrix-assisted laser desorption ionization-time-of-flight mass spectrometry (MALDI-TOF MS) analysis. In this technique, protein of interest is cleaved into smaller fragments; the resultant peptide fragments are measured and used for database search (with database searching engine such as ProFound) to identify the protein. In the positive ion mode, the tendency for serine or threonine phosphopeptides to show a predominant neutral loss of 98 Da owing to $H_3PO_4$ loss; while tyrosine phosphopeptides show only a loss of 80 Da owing to $HPO_3$ loss.

Figure 15:
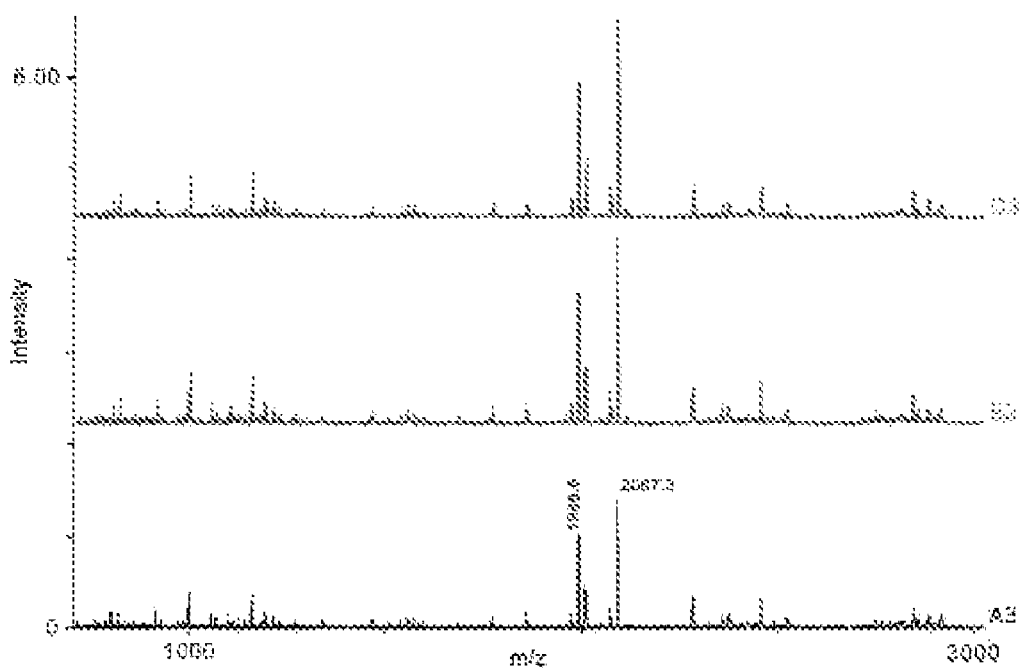
FIG. 15 is a mass spectrum of the phosphorylated peptide isolated from a tryptic digest of ovalbumin using $TiO_2$-coated magnetic beads.

FIG. 15 shows aMS spectrum of the phosphorylated peptide isolated from a tryptic digest of ovalbumin using $TiO_2$-coated magnetic beads. In addition to the phosphorylated peptide, there is a peak indicating the neutral loss of 98 Da owing to $H_3PO_4$ loss. The samples were analyzed on a PerkinElmer prOTOF™ 2000 MALDI O-TOF Mass Spectrometer. Phosphorylated protein and peptide identification with mass spectrometry-based techniques have been developed using MS an MS/MS.

Figure 16:
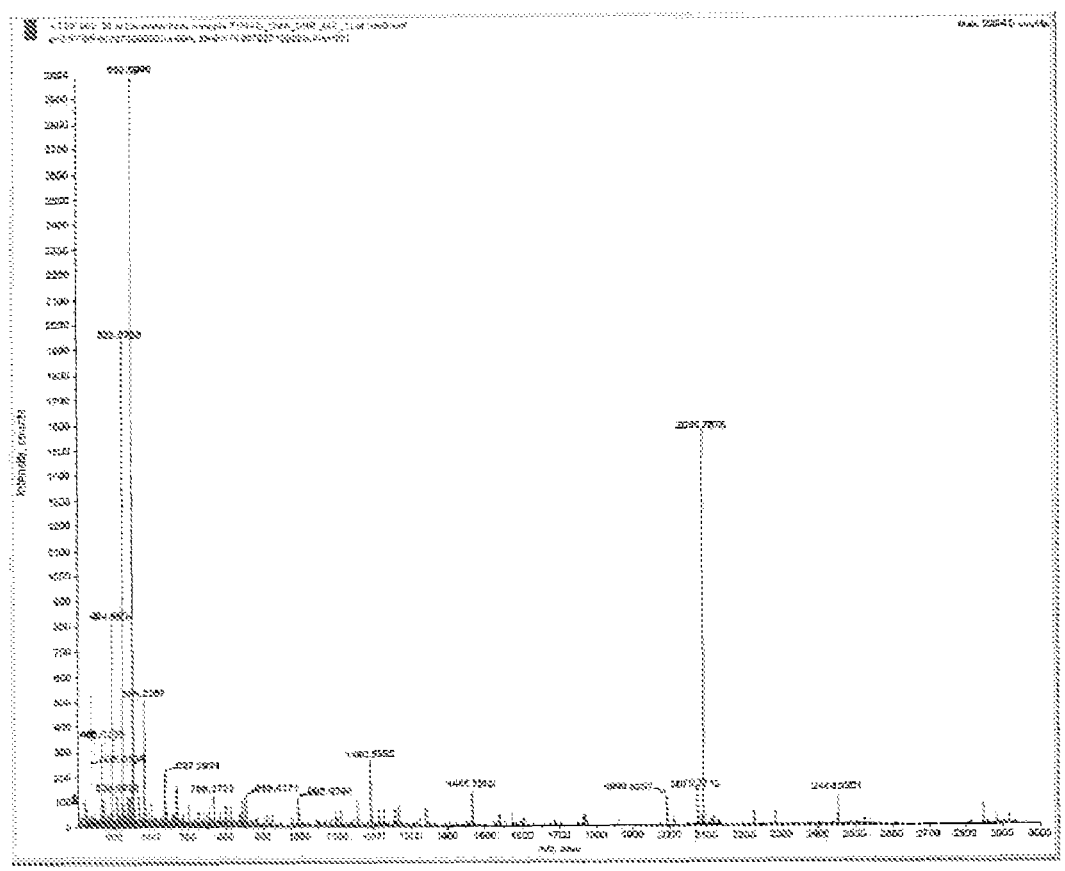
FIG. 16 is a mass spectrum of the phosphorylated peptide isolated from the trypsin digest of ovalbumin.
Figure 17:
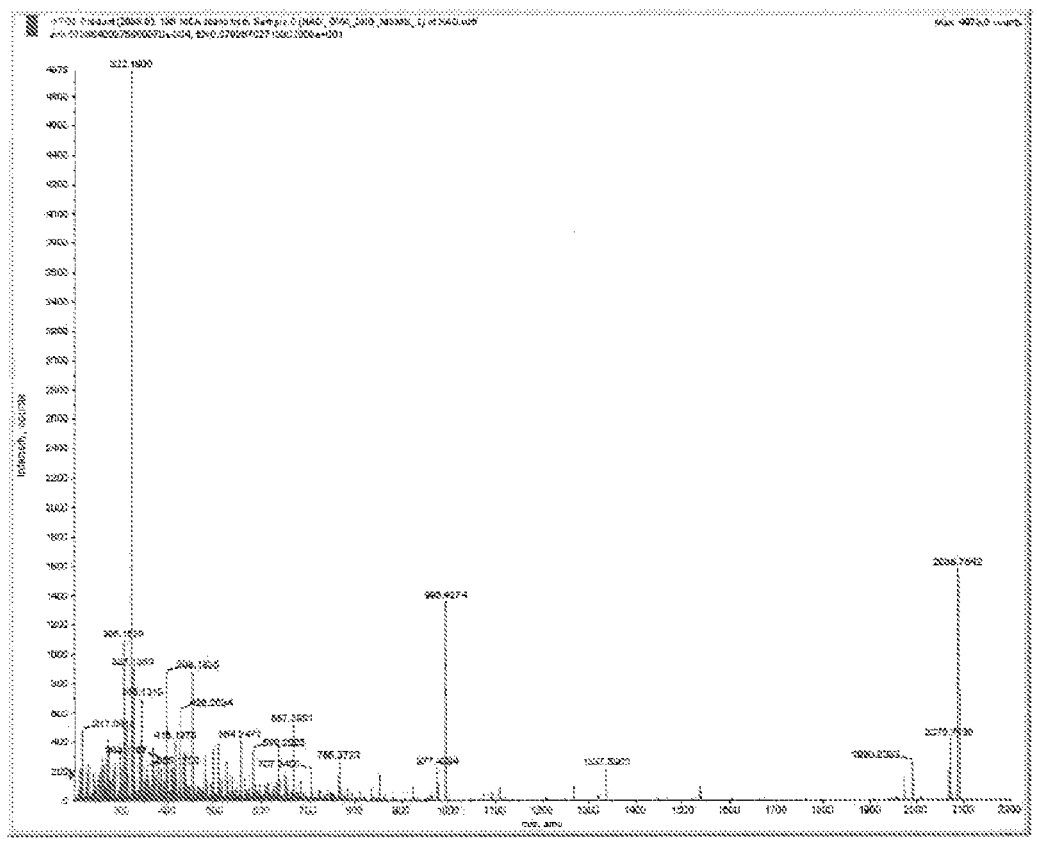
FIG. 17 is an MS/MS spectra of the fragment ion from parent mass ion 2088.9 Da. The peptide MW 1088.9 is EVVGSAEAGVDAASVSEEFR; phosphorylated at the first S (G-pS-A).

FIG. 16 shows spectra of the phosphorylated peptide isolated from the trypsin digest of ovalbumin. There is a mass peak at MW=2088.9 Da. The MASCOT database search result identified the protein as ovalbumin [validated]-chicken (OACH) with high score 100. FIG. 17 shows MS/MS spectra of the fragment ion from parent mass ion 2088.9 Da. The peptide MW 1088.9 is EVVGSAEAGVDAASVSEEFR; phosphorylated at the first S (G-pS-A).

The experiment confirms compatibility of phosphoprotein detection with the phosphomonoester-selective binding agent with enrichment of phosphorylated peptides, their mass spectrometry-based characterization and identification of phosphorylated residues within the phosphopeptides.

Example 16

Figure 18:
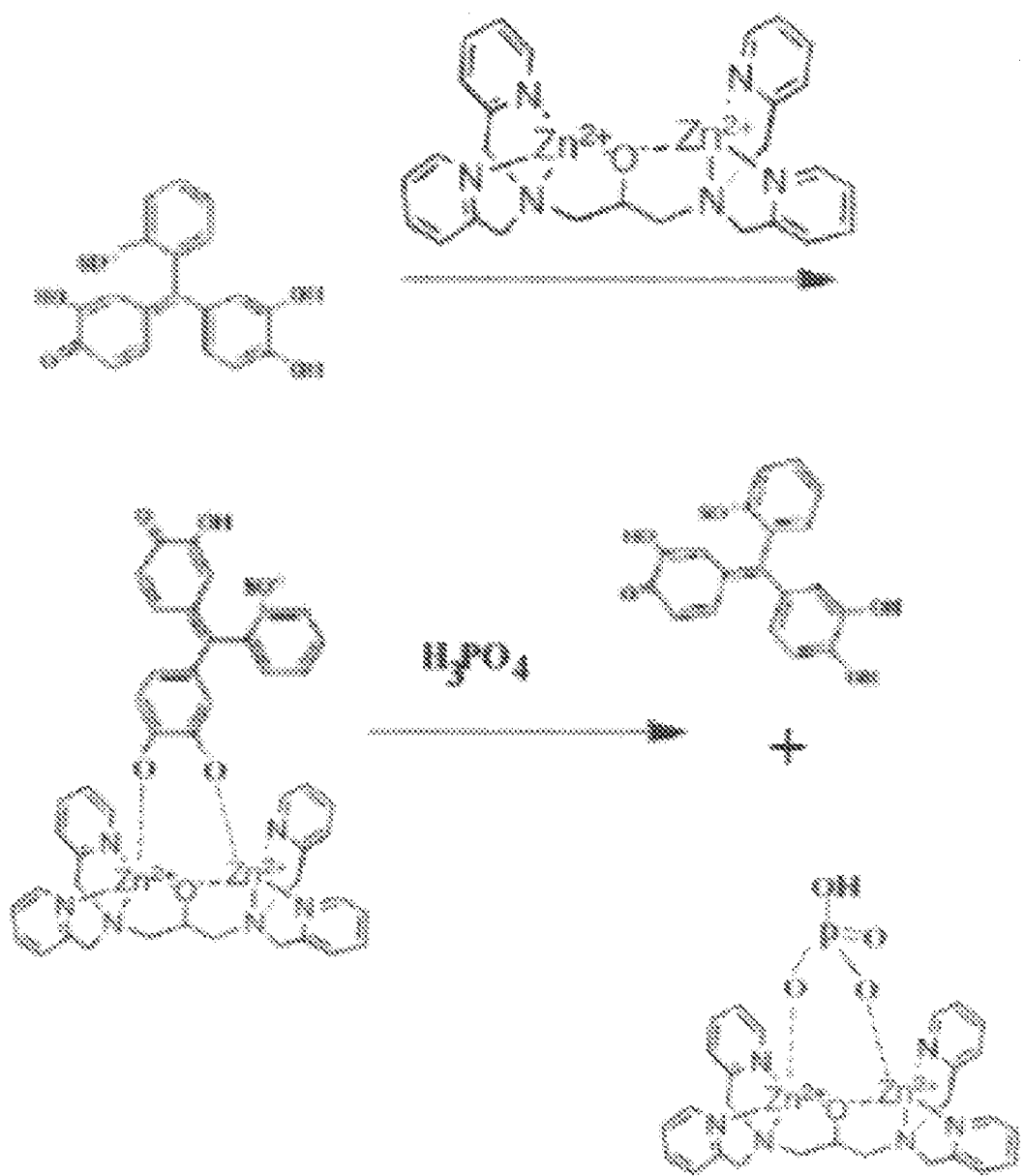
FIG. 18 is a schematic showing the non-covalent interaction of a Pyrocatechol Violet counter-anion (upper left) with a dinuclear zinc Phos-tag™, a non-limiting phosphomonoester-selective binding agent, (upper right, above arrow) for form a Pyrocatechol Violet/Phos-tag complex (lower left). The Pyrocatechol Violet counter-anion complex with the dinuclear zinc Phos-tag (i.e., two Zn2+ cations bound to Phos-tag) blocks interaction of the Phos-tag with carboxylate anions on proteins and quenches the innate fluorescence of Phos-tag itself. Phosphomonoester moieties ($H_3PO_4$ from, e.g., inorganic phosphate or phosphorylated residues on proteins, peptides, lipids, or carbohydrates) can displace the Pyrocatechol Violet counter-anion quencher (thus freeing it), and unmask the fluorescence of the dinuclear zinc Phos-tag complexed (non-covalently) to the phosphomonoester group (lower left).
Figure 19:
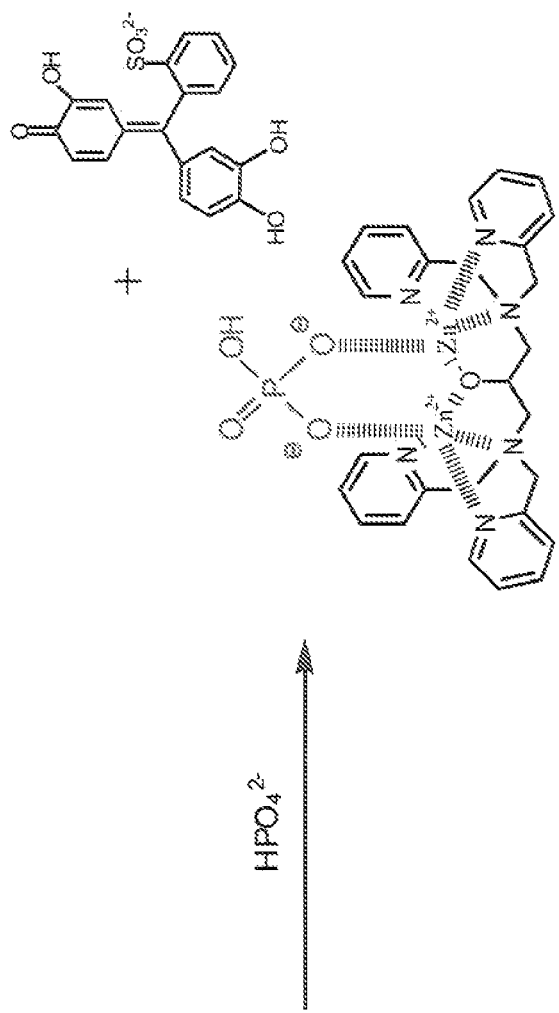
FIG. 19 is a schematic representation illustrating the displacement of Pyrocatechol violet from Zn Phos-tag by a phosphomonoester residue. The complex comprising a pyrocatechol violet molecule non-covalently bound to Zn Phostag interacts with HPO42— to result in the HPO4 non-covalently bound to the Zn Phostag and the pyrocatechol violet released as a free molecule.
Figure 19:
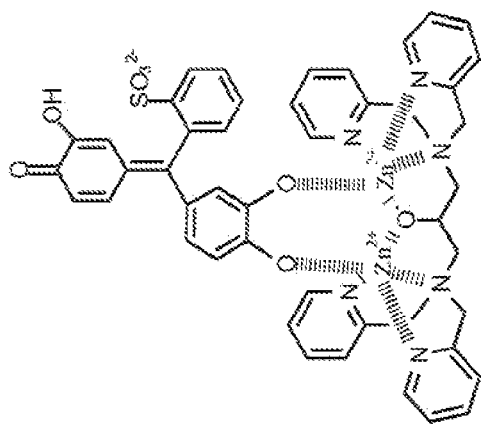
Figure 20:
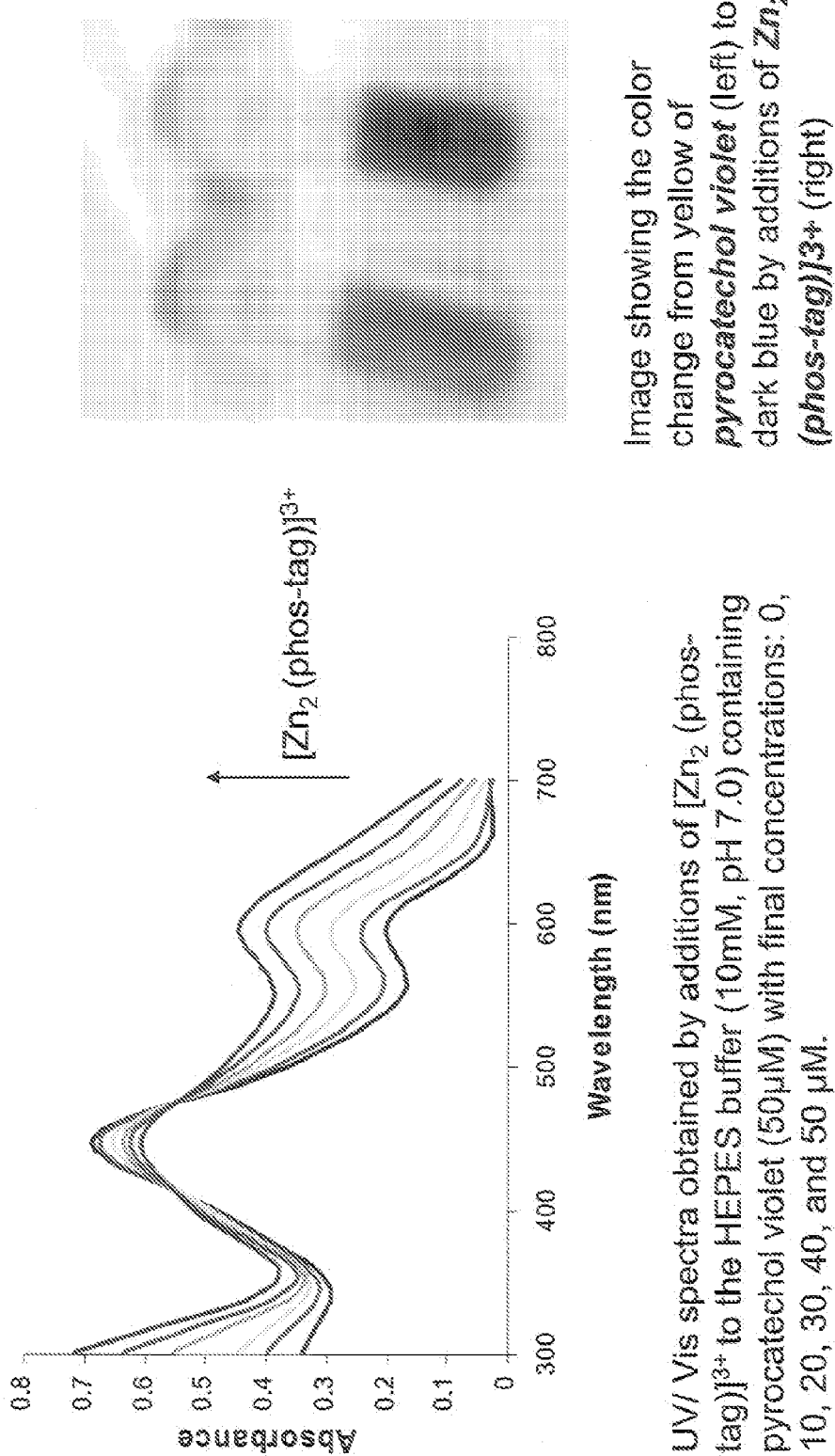
FIG. 20 is a representation of a graph showing the change in UV/Vis spectrum obtained by adding Zn Phos-tag to pyrocatechol violet. The right panel is a photograph showing the visible color change of pyrocatechol violet alone (left) and pyrocatechol violet in the presence of Zn Phos-tag (right).
Figure 21:
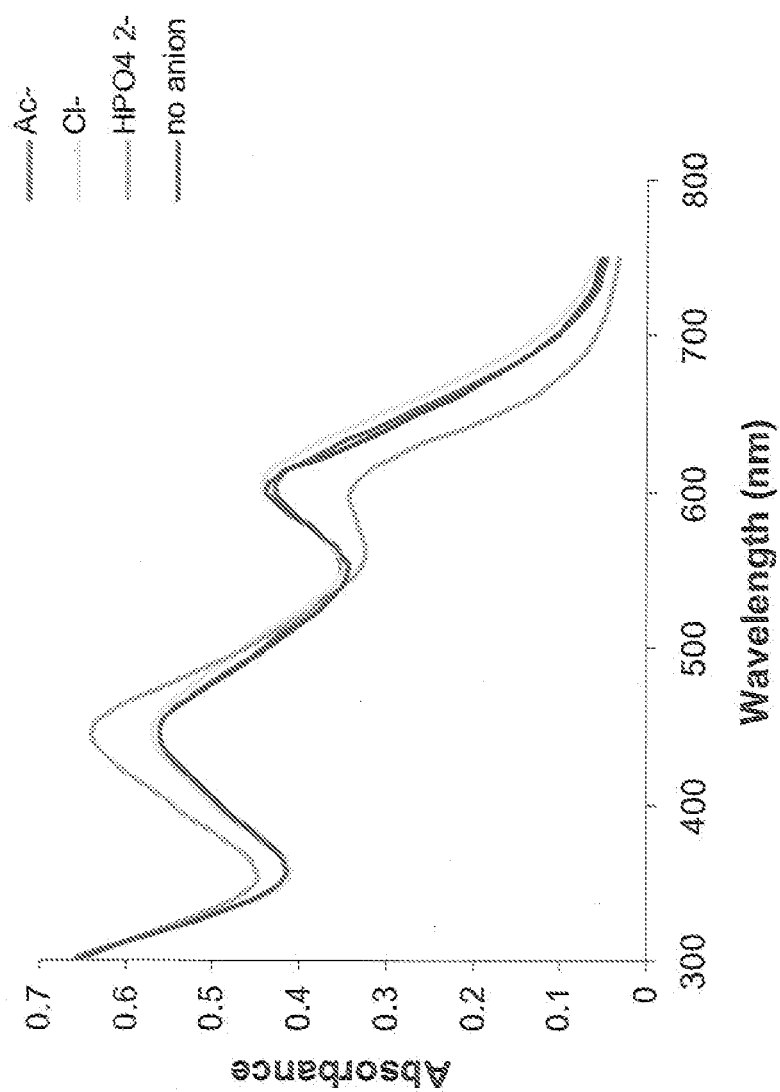
FIG. 21 is a representation of a UV/Visible spectrum of Phos-tag (a non-limiting phosphomonoester-selective binding agent) bound to Zn2+ (Zn Phos-tag), where the Zn Phos-tag is non-covalently complexed with pyrocatechol violet and exposed to 250 μM of acetate anions, chlorine anions, phosphate anions and no anion.
Figure 22:
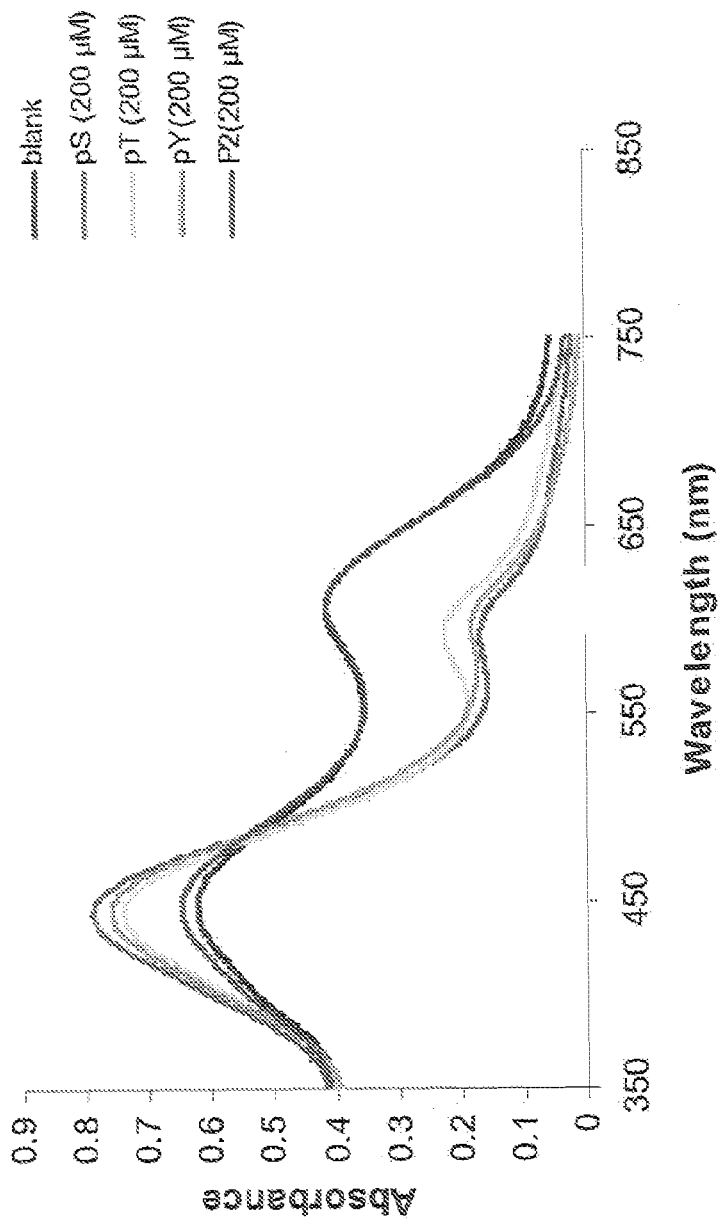
FIG. 22 is a representation of a UV/Visible spectrum of Phos-tag (a non-limiting phosphomonoester-selective binding agent) bound to Zn2+ (Zn Phos-tag), where the Zn Phos-tag is non-covalently complexed with pyrocatechol violet and exposed to 200 μM of phosphoserine peptide, phosphothreonine peptide, phsophotyrosine peptide and an unphosphorylated peptide.
Figure 23:
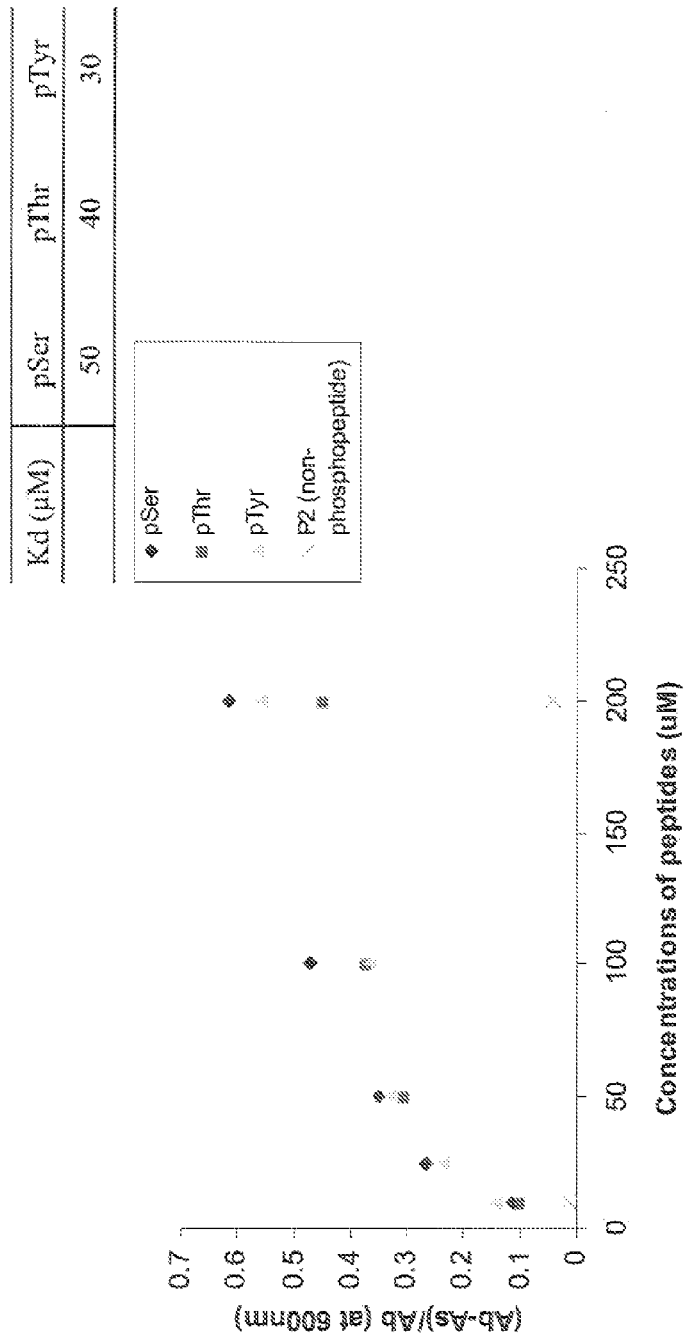
FIG. 23 is a graph showing the relative binding of Phos-tag (a non-limiting phosphomonoester-selective binding agent) bound to Zn2+ (Zn Phos-tag) to phosphoserine peptide (purple dots), phosphothreonine peptide (pink dots), phsophotyrosine peptide (yellow dots) and an unphosphorylated peptide (blue X).
Figure 24:
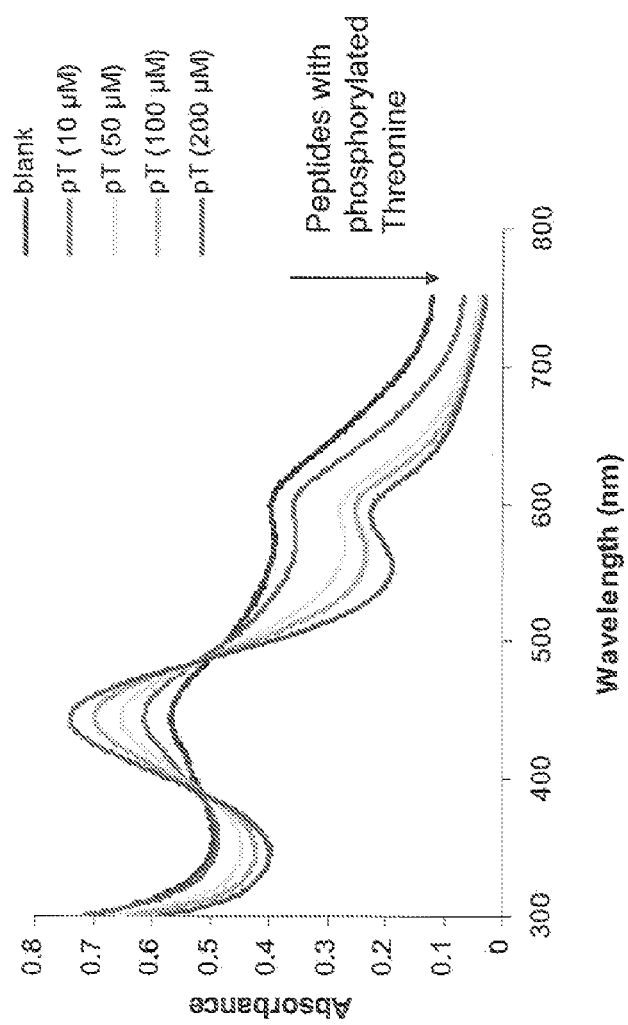
FIG. 24 is a representation of a UV/Visible spectrum of Phos-tag (a non-limiting phosphomonoester-selective binding agent) bound to Zn2+ (Zn Phos-tag), where the Zn Phos-tag is non-covalently complexed with pyrocatechol violet and exposed to a phos-phothreonine peptide having the sequence shown at the bottom of the figure at 10 μM, 50 μM, 100 μM, 200 μM, or in the presence of no peptide.
Figure 25:
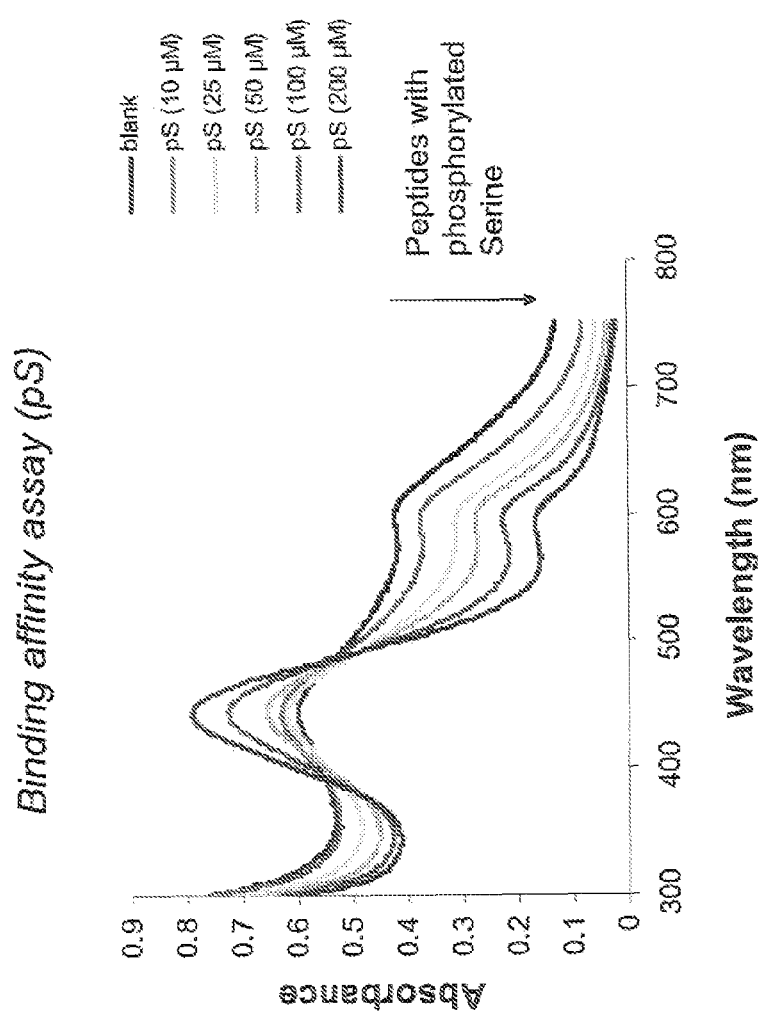
FIG. 25 is a representation of a UV/Visible spectrum of Phos-tag (a non-limiting phosphomonoester-selective binding agent) bound to Zn2+ (Zn Phos-tag), where the Zn Phos-tag is non-covalently complexed with pyrocatechol violet and exposed to a phosphoserine peptide having the sequence shown at the bottom of the figure at 10 μM, 25 μM, 50 μM, 100 μM, 200 μM or in the presence of no peptide.
Figure 26:
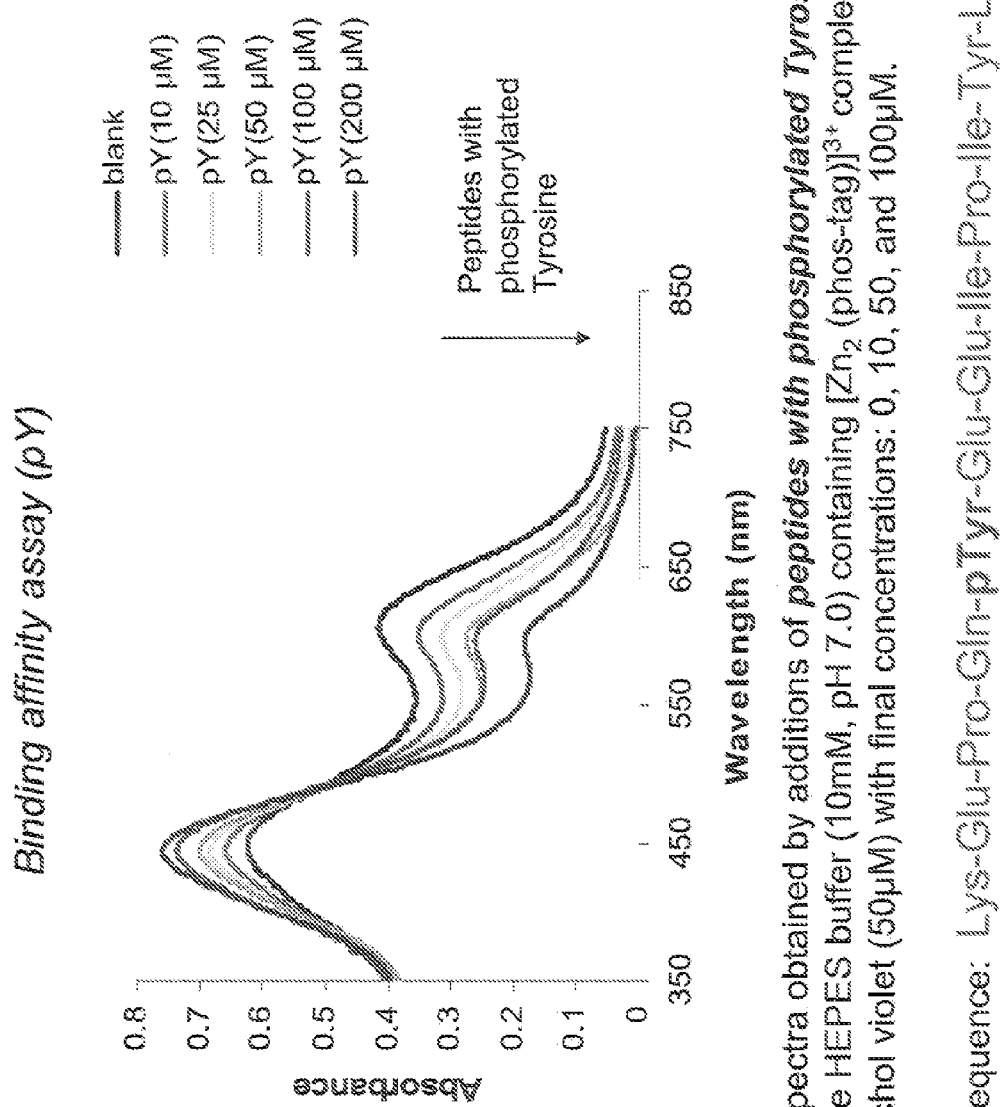
FIG. 26 is a representation of a UV/Visible spectrum of Phos-tag (a non-limiting phosphomonoester-selective binding agent) bound to Zn2+ (Zn Phos-tag), where the Zn Phos-tag is non-covalently complexed with pyrocatechol violet and exposed to a phosphotyrosine peptide having the sequence shown at the bottom of the figure at 10 μM, 25 μM, 50 μM, 100 μM, 200 μM or in the presence of no peptide.
Figure 27:
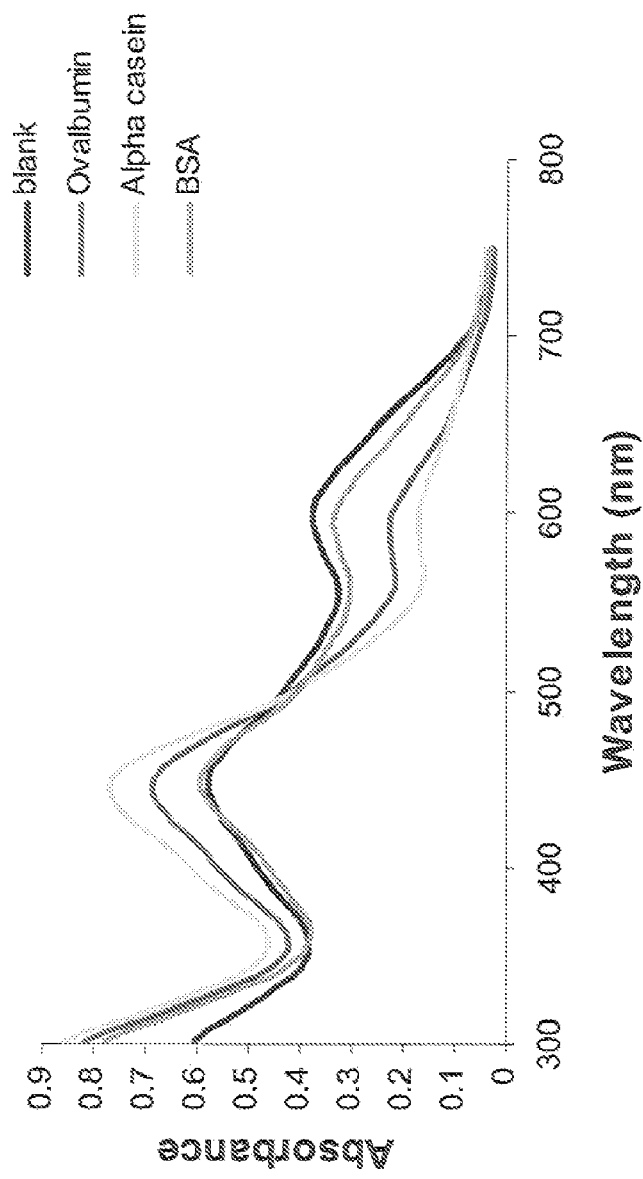
FIG. 27 is a representation of a UV/Visible spectrum of Phos-tag (a non-limiting phosphomonoester-selective binding agent) bound to Zn2+ (Zn Phos-tag), where the Zn Phos-tag is non-covalently complexed with pyrocatechol violet and exposed to 3 mg/ml of ovalbumin (purple line), alpha or beta casein (yellow line), bovine serum albumin (BSA) (blue line), and no protein (purple line).

In order to assess its binding selectivity, a non-limiting phosphomonoester-selective binding agent of the invention, (Phos-Tag™ molecule) complexed (non-covalently) to Zn2+ cations was incorporated into a colorimetric sensor capable of detecting phosphorylated species in aqueous media at neutral pH. Briefly, the assay is based upon the selective binding of pyrocatechol violet to the Phos-tag complex. As shown in FIG. 18, pyrocatechol violet (upper left) interacts with a Zn Phos-tag™ molecule to form a complex which can be disrupted upon the addition of a phosphomonoester (i.e., H3PO4), where the phosphomonoester displaces the pyrocatechol violent from the phosphomonoester (see also FIG. 19). Binding of pyrocatechol violet to the zinc complex (i.e., Phos-tag), produces a violet color, but displacement of the indicator dye from the complex by a higher affinity competing ligand, such as a phosphorylated molecule, generates a color change to yellow. The right panel of FIG. 20 shows the reverse, where the yellow color of free pyrocatechol violet (left) is changed to dark blue by addition of the zinc complex (i.e., Zn Phos-tag). This is readily monitored spectrophotometrically as an absorbance shift from 624 nm to 444 nm (see FIG. 20, left panel). This dramatic color change is specific to phosphate anions ($HPO_4^{2-}$), as acetate (Ac-), clorine (Cl—), and no anion does not cause the same shift (see FIG. 21). Experiments with the chemosensor established that Phos-tag reagent selectively binds to the phosphomonoester residues of phosphopeptides and phosphoproteins via a charge-based coordination of chelated Zn (II) cations. Interaction with phosphoserine-, phosphothreonine- and phosphotyrosine-containing peptides, but not unphosphorylated peptide was demonstrated using the assay (see FIG. 22). The binding affinities of the pyrocatechol violet:Phos-tag complex to phosphotyrosine, phosphoserine, phosphothreonine, and a non-phosphopeptide was also determined (see FIGS. 23, 24, 25, and 26). Selective interaction with the phosphoproteins ovalbumin and beta-casein, but not the unphosphorylated protein serum albumin was also demonstrated (see FIG. 27). Visually, the color change of the pyrocatechol violet:Phos-tag complex in the presence of various analytes is striking (see FIG. 28). Interaction with other anionic residues, including carboxylate residues, was determined to be insignificant using the same assay. Fluorophore-conjugated Phos-tag dyes were subsequently synthesized that permitted the direct high sensitivity detection of phosphoproteins in polyacrylamide gels or on electroblot membranes, without the requirement for secondary detection reagents or a comparison of the migration distances of protein bands between different gels. Limits of detection for the fluorophores was roughly 1 ng of phosphoprotein and linear dynamic range extended over three orders of magnitude of protein amount. Based upon the cited results, direct binding of dinuclear Zn (II) Phos-tag complex to the phosphomonoester group of phosphoproteins and phosphopeptides is expected to minimize sequence context differences in binding, often encountered using antibody-based detection approaches, making the reagent a universal chemosensor of protein phosphorylation status.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence or absence of a phospho-transfer activity in a sample, the method comprising the steps of:
    (a) contacting at least one particle encoded with a particle code with a sample,
        wherein the at least one encoded particle has an attached phospho-transfer substrate and the phospho-transfer substrate is identifiable by the particle code of the encoded particle;
    (b) contacting the at least one contacted encoded particle with a detectable phosphomonoester-selective binding agent; and
    (c) determining whether there is binding of the detectable phosphomonoester-selective binding agent to at least one encoded particle, wherein the binding of said detectable phosphomonoester-selective binding agent indicates the presence of phospho-transfer activity in said sample.

2. The method of claim 1, further comprising after contacting the at least one encoded particle and the sample, separating the at least one contacted encoded particle from the sample.

3. The method of claim 1, wherein the determining comprises detecting the presence, absence, or amount of the binding of the detectable phosphomonoester-selective binding agent to at least one encoded particle coded with a particle code contacted with the sample as compared to the presence, absence, or amount of binding of the detectable phosphomonoester-selective binding agent to the at least one encoded particle coded with a particle code not contacted to the sample.

4. The method of claim 1, wherein the phospho-transfer activity is a kinase activity.

5. The method of claim 4, wherein the kinase is a tyrosine kinase.

6. The method of claim 4, wherein the kinase is a threonine/serine kinase.

7. The method of claim 1, wherein the phospho-transfer activity is a phosphatase activity.

8. The method of claim 1, wherein the phospho-transfer activity is a phosphodiesterase activity.

9. The method of claim 1, wherein the phosphomonoester-selective binding agent comprises the structure of Formula I:

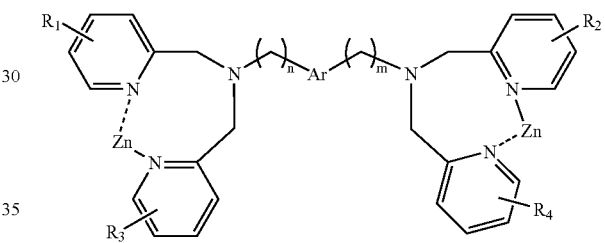

wherein
    each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group,
    each n and m are independently 0 or 1; and
    Ar is aryl.

(b) contacting the at least one contacted encoded particle with a detectable phosphomonoester-selective binding agent that comprises the structure of Formula I:

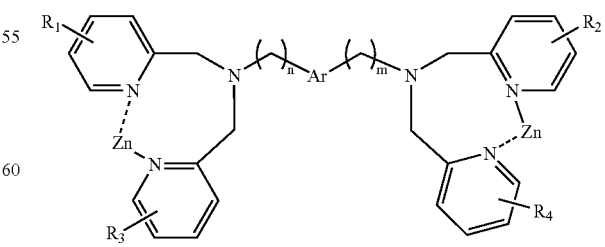

wherein
    each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group, each n and m are independently 0 or 1;

Ar is aryl; and (c) determining whether there is binding of the detectable phosphomonoester-selective binding agent to at least one encoded particle, wherein the binding of said detectable phosphomonoester-selective binding agent indicates the presence of phospho-transfer activity in said sample.

10. The method of claim 1, wherein the phosphomonoester-selective binding agent comprises the structure of Formula II:

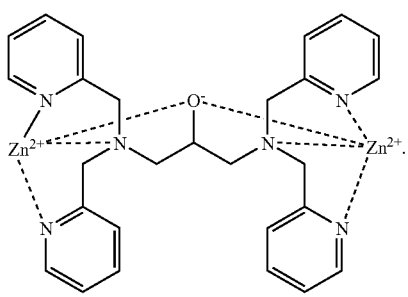

11. The method of claim 1, wherein said at least one encoded particle is one or more pluralities of encoded particles, wherein each plurality of encoded particles has a different attached phospho-transfer substrate.

12. The method of claim 1, wherein said determining step comprises flow cytometry.

13. The method of claim 1, wherein said determining step is performed at a pH of at least greater than 5.5.

14. The method of claim 1, wherein said particle code is a holographic bar code.

15. A method for detecting the presence or absence of a phospho-transfer activity in a sample, the method comprising the steps of:

(a) contacting at least one particle encoded with a particle code with a sample,
wherein the at least one encoded particle has an attached phospho-transfer substrate and the phospho-transfer substrate is identifiable by the particle code of the encoded particle.

16. The method of claim 15, wherein the detectable phosphomonoester-selective binding agent comprises the structure of Formula II:

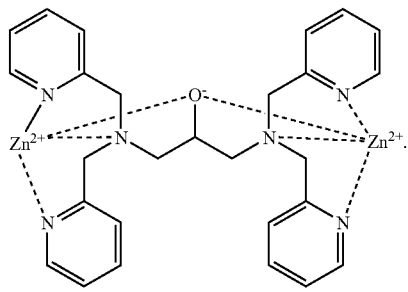

17. A method for detecting the presence or absence of a phospho-transfer activity in a sample, the method comprising the steps of:

(a) contacting at least one particle encoded with a particle code with a sample,
wherein the at least one encoded particle has an attached phospho-transfer substrate, the phospho-transfer substrate being identifiable by the particle code of the encoded particle;

(b) contacting the at least one contacted encoded particle with a detectable phosphomonoester-selective binding agent; and (c) determining whether there is binding of the detectable phosphomonoester-selective binding agent to at least one encoded particle, wherein the detection is performed at a pH of at least greater than 5.0, wherein the binding of said detectable phosphomonoester-selective binding agent indicates the presence of phospho-transfer activity in said sample.

18. A method for detecting the presence or absence of one or more phospho-transfer activities in a sample, the method comprising the steps of:

(a) contacting a mixture of particles encoded with a particle code with a sample,
wherein the mixture of encoded particles comprises one or more pluralities of particles encoded with a particle code, each plurality of particles having a different attached phospho-transfer substrate, the phospho-transfer substrate being identifiable by a the particle code of the encoded particle;

(b) contacting the mixture of contacted encoded particles with a detectable phosphomonoester-selective binding agent; and (c) determining whether there is binding of the detectable phosphomonoester-selective binding agent to at least one of the encoded particles, wherein the binding of said detectable phosphomonoester-selective binding agent indicates the presence of phospho-transfer activity in said sample.

19. The method of claim 18, wherein the mixture of particles includes particles for different phospho-transfer substrates, each substrate comprising a recognition site specific to a phospho-transfer activity.

20. The method of claim 18, wherein at least two pluralities comprise different phospho-transfer substrates, each substrate comprising a peptide containing a recognition site for a different phospho-transfer activity.

* * * * *

UNITED STATES PATENT AND TRADEMARK OFFICE
CERTIFICATE OF CORRECTION

PATENT NO. : 7,550,271 B2
APPLICATION NO. : 11/742443
DATED : June 23, 2009
INVENTOR(S) : Wayne F. Patton Page 1 of 2

It is certified that error appears in the above-identified patent and that said Letters Patent is hereby corrected as shown below:

Column 44, line 50 through Column 45, line 16 (Claim 9), below "aryl." please delete "(b) contacting the at least one contacted encoded particle with a detectable phosphomonoester-selective binding agent that comprises the structure of Formula I:

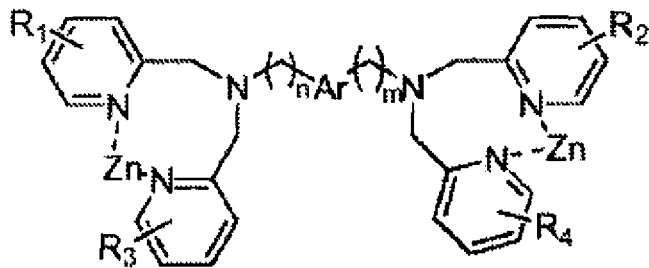

wherein each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group, each n and m are independently 0 or 1; Ar is aryl; and
(c) determining whether there is binding of the detectable phosphomonoester-selective binding agent to at least one encoded particle, wherein the binding of said detectable phosphomonoester-selective binding agent indicates the presence of phospho-transfer activity in said sample."

Column 45, line 60 (Claim 15), please delete "encoded particle." and insert

--encoded particle;
(b) contacting the at least one contacted encoded particle with a detectable phosphomonoester-selective binding agent that comprises the structure of Formula I:

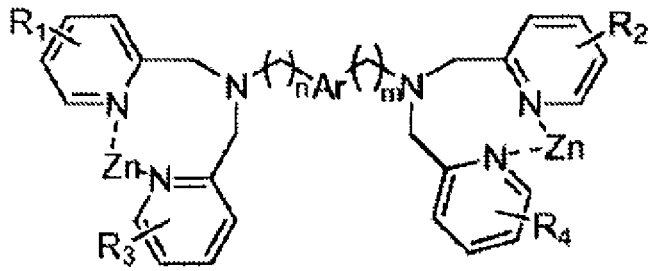

UNITED STATES PATENT AND TRADEMARK OFFICE
CERTIFICATE OF CORRECTION

PATENT NO. : 7,550,271 B2
APPLICATION NO. : 11/742443
DATED : June 23, 2009
INVENTOR(S) : Wayne F. Patton It is certified that error appears in the above-identified patent and that said Letters Patent is hereby corrected as shown below:

wherein
each $R_1$, $R_2$, $R_3$, and $R_4$ are, independently, an H; an alkyl group having 1 to 16 carbon atoms; an acyl group; a carboxyalkyl group; an acylalkyl group; a carbamoylalkyl group; a cyanoalkyl group; a hydroxyalkyl group; an aminoalkyl group; or a haloalkyl group having 1 to 16 carbon atoms and 1 to 5 halogens; a carboxyl group; a carbamoyl group; a hydroxyl group; a cyano group; an amino group; or a halogen group, each n and m are independently 0 or 1; Ar is aryl; and
(c) determining whether there is binding of the detectable phosphomonoester-selective binding agent to at least one encoded particle, wherein the binding of said detectable phosphomonoester-selective binding agent indicates the presence of phospho-transfer activity in said sample.-- therefor.

Column 46, line 43 (Claim 18), after "by" please delete "a."

Signed and Sealed this

Twenty-fifth Day of August, 2009

David J. Kappos
*Director of the United States Patent and Trademark Office*